United States Patent
Sharma et al.

(10) Patent No.: US 11,457,835 B2
(45) Date of Patent: Oct. 4, 2022

(54) ELECTROMAGNET GRADIENT COIL APPARATUS FOR MICRO-DEVICE LOCALIZATION

(71) Applicant: California Institute of Technology, Pasadena, CA (US)

(72) Inventors: Saransh Sharma, Pasadena, CA (US); Mikhail Shapiro, Los Angeles, CA (US); Azita Emami, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 61 days.

(21) Appl. No.: 17/097,349

(22) Filed: Nov. 13, 2020

(65) Prior Publication Data
US 2021/0141034 A1    May 13, 2021

Related U.S. Application Data

(60) Provisional application No. 62/934,763, filed on Nov. 13, 2019, provisional application No. 62/934,767, filed on Nov. 13, 2019.

(51) Int. Cl.
*G01R 33/00* (2006.01)
*A61B 5/07* (2006.01)
(Continued)

(52) U.S. Cl.
CPC ............... *A61B 5/073* (2013.01); *A61B 5/05* (2013.01); *A61B 5/076* (2013.01); *A61B 5/6861* (2013.01);
(Continued)

(58) Field of Classification Search
CPC ............... G01R 33/00; G01R 33/0035; G01R 33/0023; G01R 33/0017; G01R 31/3191;
(Continued)

(56) References Cited

U.S. PATENT DOCUMENTS 9,915,641 B2    3/2018 Shapiro et al.
10,466,277 B1   11/2019 Brooks
(Continued)

FOREIGN PATENT DOCUMENTS

| JP | 10199724 A | 7/1998 | |
|---|---|---|---|
| JP | 2014166306 A | 9/2014 | |
| JP | 2014166306 A * | 9/2014 | ............... A61B 1/00 |

OTHER PUBLICATIONS

W. M. Ricci et al., "Intramedullary Nailing of Femoral Shaft Fractures: Current Concepts," JAAOS, 2009, pp. 296-305, vol. 17, No. 5.

(Continued)

*Primary Examiner* — Jermele M Hollington
*Assistant Examiner* — Taqi R Nasir
(74) *Attorney, Agent, or Firm* — Intrinsic Law Corp.

(57) ABSTRACT

An apparatus for producing magnetic field gradients includes (a) a first planar electromagnet coil set configured to produce a first magnetic field gradient with respect to a first axis, (b) a second planar electromagnet coil set configured to produce a second magnetic field gradient with respect to a second axis that is orthogonal to the first axis, (c) a third planar electromagnet coil set configured to produce a third magnetic field gradient with respect to a third axis that is orthogonal to the first and second axes, and (d) a controller configured to selectively provide power to the first, second, and/or third electromagnet coil sets to sequentially produce a localization magnetic field gradient with respect to each of the first, second, and third axes, at least a portion of each localization magnetic field gradient having a monotonically-varying magnetic field magnitude along a respective axis.

41 Claims, 32 Drawing Sheets

(51) Int. Cl.
    A61B 5/00      (2006.01)
    A61B 5/05      (2021.01)
    G01B 7/31      (2006.01)
    G01R 33/022    (2006.01)
    G01R 33/385    (2006.01)

(52) U.S. Cl.
    CPC .............. *G01B 7/31* (2013.01); *G01R 33/022*
                (2013.01); *G01R 33/385* (2013.01); *A61B*
                                    *2562/0223* (2013.01)

(58) Field of Classification Search
    CPC .... G01R 33/022; G01R 33/385; G01B 7/004;
                G01B 7/31; G01C 17/38; G06F 3/017;
                G06F 3/0346; G06F 3/012; A61B
                2562/0223; A61B 5/073; A61B 5/05;
                A61B 5/076; A61B 5/6861
    See application file for complete search history.

(56)                References Cited

U.S. PATENT DOCUMENTS

| | | | |
|---|---|---|---|
| 2011/0009697 A1* | 1/2011 | Kawano | A61B 1/041 600/117 |
| 2013/0303878 A1 | 11/2013 | Nevo et al. | |
| 2014/0167762 A1* | 6/2014 | Sugiyama | G01R 33/3858 324/322 |
| 2015/0297065 A1* | 10/2015 | Park | A61B 1/041 600/109 |
| 2016/0022123 A1 | 1/2016 | Katznelson et al. | |
| 2019/0388105 A1 | 12/2019 | Sharma et al. | |

OTHER PUBLICATIONS

A. Wang et al., "Wireless Capsule Endoscopy," Technology Status Evalutation Reports, 2013, pp. 805-815, vol. 78, No. 6, Elsevier.
U. Mezger et al., "Navigation in surgery," Langenbeck's Archives of Surgery, 2013, pp. 501-514, vol. 398, No. 4, Springer.
H. M. Kremers et al., "Prevalence of Total Hip and Knee Replacement in the United States," The Journal of bone and joint surgery. American volume, 2015, pp. 1386-1397, vol. 97, No. 17, The Journal of Bone and Joint Surgery, Incorporated.
D. Vasisht et al., "In-body backscatter communication and localization," Proceedings of the 2018 Conference of the ACM Special Interest Group on Data Communication (SIGCOMM '18). Association for Computing Machinery, Aug. 2018, pp. 132-146, New York, NY, USA.
A. L. Simpson et al., "Comparison Study of Intraoperative Surface Acquisition Methods for Surgical Navigation," IEEE Transactions on Biomedical Engineering, 2013, pp. 1090-1099, vol. 60, No. 4, IEEE.
D. Formica et al., "Biological effects of exposure to magnetic resonance imaging: an overview," BioMedical Eng. OnLine, 2004, pp. 1-12, vol. 3, No. 11, BioMed Central Ltd.
V. Grover et al., "Magnetic Resonance Imaging: Principles and Techniques: Lessons for Clinicians," Journal of Clinical and Experimental Hepatology, 2015, pp. 246-255, vol. 5, No. 3, Elsevier Inc.
M. Monge et al., "Localization of microscale devices in vivo using addressable transmitters operated as magnetic spins," Nature Biomedical Engineering, 2017, vol. 6, pp. 736-744, Springer Nature Limited.
J. Marques et al., "Low-Field MRI: An MR Physics Perspective," Journal of Magnetic Resonance Imaging, 2019, pp. 1528-1542, vol. 49, No. 6, Wiley Online Library.
D. Son et al., "A 5-D Localization Method for a Magnetically Manipulated Untethered Robot using a 2-D Array of Hall-effect Sensors," IEEE/ASME Transactions on Mechatronics, 2016, pp. 708-716, vol. 21, No. 2, IEEE.
A. Emami et al., "MRI-Inspired High-Resolution Localization for Biomedical Applications: Artificial Nuclear Spins on a Chip," IEEE Solid-State Circuits Magazine, 2018, pp. 34-42, vol. 10, No. 4, IEEE.
Rao et al., "Evaluation of gastrointestinal transit in clinical practice: position paper of the American and European Neurogastroenterology and Motility Societies", Neurogastroenterology & Motility, 2011, vol. 23, 8-23, Blackwell Publishing Ltd.
Hoffman et al., "Gastrointestinal Motility Monitor (GIMM)," Journal of Visualized Experiments, 2010, pp. 1-3, vol. 1, No. 46, JOVE.
Keller et al., "Advances in the diagnosis and classification of gastric and intestinal motility disorders," Nature Reviews, Gastroenterology & Hepatology, 2018, pp. 291-308, vol. 15, Springer Nature Limited.
Medtronic, "SmartPill Motility Testing System", Motility Testing, https://www.medtronic.com/covidien/en-us/products/motility-testing/smartpill-motility-testing-systemhtml#smartpill-motility-capsule.
Lo et al., "A Wireless Implant for Gastrointestinal Motility Disorders," Micromachines, 2018, pp. 1-13, vol. 9, No. 17, MDPI.
ISA, "International Search Report", PCT/US20/60433, dated Mar. 9, 2021.
ISA, "International Search Report", PCT/US20/60420, dated Mar. 9, 2021.
T. Leloup et al., "A Novel Technique for Distal Locking of Intramedullary Nail Based on Two Non-constrained Fluoroscopic Images and Navigation," IEEE Trans. Med. Imaging, 2008, pp. 1202-1212, vol. 27, No. 9, IEEE.
A. M. Franz et al., "Electromagnetic Tracking in Medicine—A Review of Technology, Validation, and Applications," IEEE Trans. Med. Imaging, Aug. 2014, pp. 1702-1725, vol. 33, No. 8, IEEE.
F. Chen et al., "3D Catheter Shape Determination for Endovascular Navigation Using a Two-Step Particle Filter and Ultrasound Scanning," IEEE Trans. Med. Imaging, 2017, pp. 685-695, vol. 36, No. 3, IEEE.
F. Parent et al., "Intra-Arterial Image Guidance With Optical Frequency Domain Reflectometry Shape Sensing," IEEE Trans. Med. Imaging, 2019, pp. 482-492, vol. 38, No. 2, IEEE.
M. M. Ahmadi et al., "A Wireless-Implantable Microsystem for Continuous Blood Glucose Monitoring," IEEE Transactions on Biomedical Circuits and Systems, 2009, pp. 169-180, vol. 3, No. 3, IEEE.

* cited by examiner

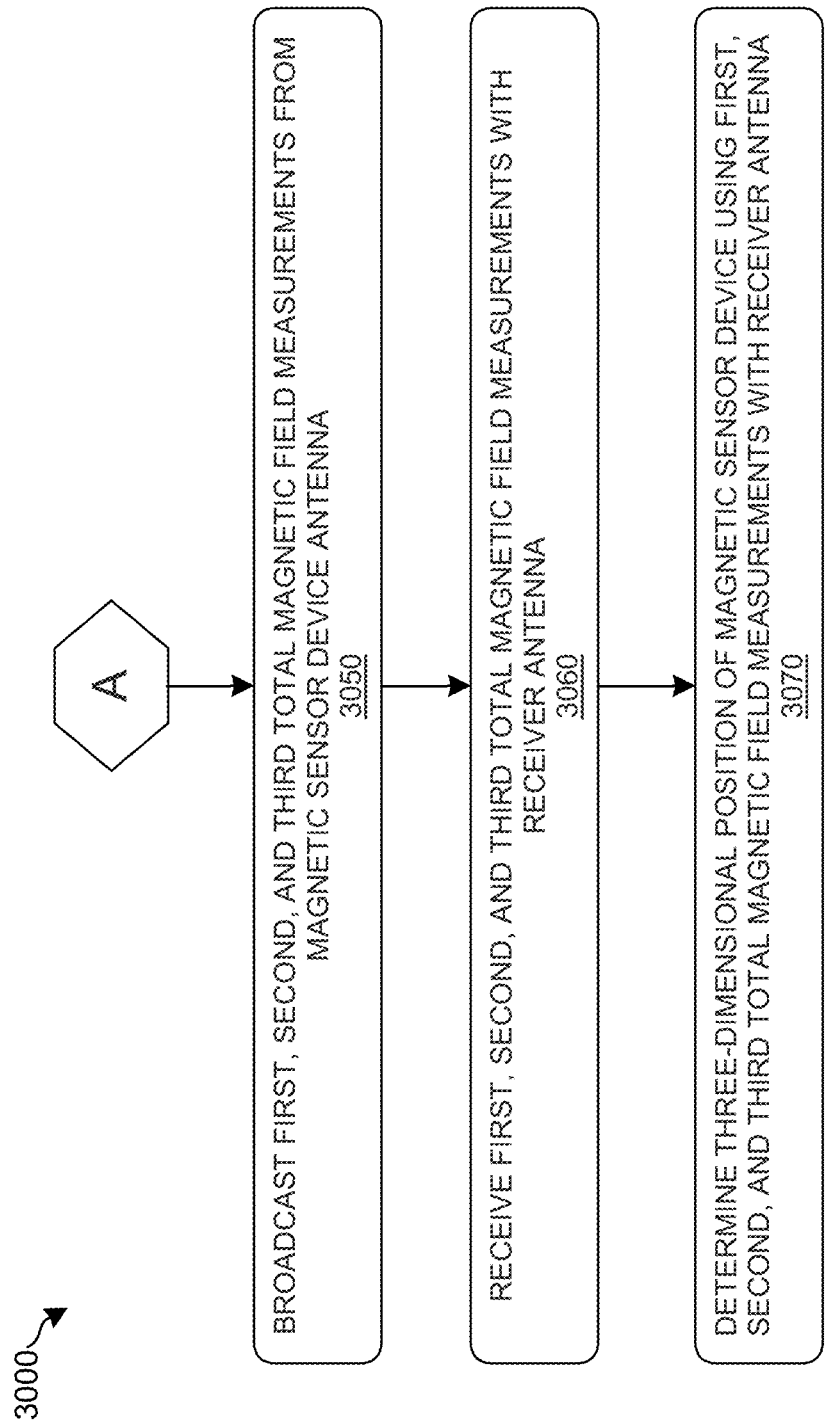

ELECTROMAGNET GRADIENT COIL APPARATUS FOR MICRO-DEVICE LOCALIZATION

CROSS-REFERENCE TO RELATED APPLICATIONS

This application claims priority to U.S. Provisional Application No. 62/934,763, titled "Real-Time GI Tract Monitoring with High Precision in 3D Using ATOMS Microchips," filed on Nov. 13, 2019 and to U.S. Provisional Application No. 62/934,767, titled "Magnetic Gradient Coil Design For Micro-Device Localization," filed on Nov. 13, 2019, which are hereby incorporated by reference.

STATEMENT REGARDING FEDERALLY-SPONSORED RESEARCH

This invention was made with government support under Grant No. CBET1823036 awarded by the National Science Foundation. The government has certain rights in the invention.

TECHNICAL FIELD

This application relates generally to an apparatus for producing magnetic field gradients along mutually-orthogonal axes.

BACKGROUND

An important line of research in contemporary science envisions introducing miniature devices into the human body to diagnose and treat localized disease. Major advances have been made towards this vision, but the practical implementation of microscale biological sensors and actuators is still largely missing from in vivo biology and medicine. Meanwhile, the need for such devices is increasing due to a greater appreciation that many prevalent diseases involve local pathology (for example, neurodegeneration, cancer, psychiatric disease, and atherosclerosis) requiring local diagnosis and treatment. Notably, the recently launched national BRAIN initiative to map the function of the mammalian brain has created demand for distributed microscale sensors enabling large-scale recording of neural activity.

Microscale sensors may require the means to (a) convert local (in the body) physiological information into electrical signals, (b) transmit these signals to external receivers (outside the body), and (c) be localized to specific parts of the body and distinguished from each other. Substantial progress has been made on the first two requirements. For example, miniaturized devices have been developed to measure action potentials and neurotransmitters, the release of tumor antigens, and the presence of viral pathogens. In addition, advances in integrated circuits and antennae have led to the development of devices that are smaller, more energy-efficient and capable of high-bandwidth data transfer. The requirement that transmitters be effectively localized and distinguished from each other, however, is currently poorly addressed because existing localization schemes based on receiver proximity have limited precision and poor scaling. This is a significant limitation for scenarios ranging from individual localization of implantable biosensors and intravascular guidewire to distributed implantable sensors of neural activity and immune cell-internalized reporters homing to diseased tissues. In fact, in these and other applications, it may be necessary to distinguish between different sensors, for example to determine what region of the organ within the body their reading values are coming from.

In particular, there are currently no effective means to precisely determine the location of microscale devices deep inside the body and communicate with them in a location-specific manner. Existing methods based on near-field radio-frequency (RF) electromagnet interactions have only a limited ability to localize and communicate with individual implants because the strong dependence of RF signals on tissue properties (specifically, body composition) drastically reduces their spatial resolution, and makes it difficult to interface with multiple devices at once. Meanwhile, localization using imaging procedures, such as x-ray computed tomography, exposes patients to ionizing radiation and can only visualize and not transmit information to and from devices at specific locations in the body.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to an apparatus for producing magnetic field gradients comprising: a first planar electromagnet coil set configured to produce a first magnetic field gradient with respect to a first axis; a second planar electromagnet coil set configured to produce a second magnetic field gradient with respect to a second axis that is orthogonal to the first axis; a third planar electromagnet coil set configured to produce a third magnetic field gradient with respect to a third axis that is orthogonal to the first and second axes, the first, second, and third planar electromagnet coil sets vertically arranged with respect to the third axis; and a controller configured to selectively provide power to the first planar electromagnet coil set, the second planar electromagnet coil set, and/or the third planar electromagnet coil set to sequentially produce a localization magnetic field gradient with respect to each of the first, second, and third axes, at least a portion of each localization magnetic field gradient having a monotonically-varying magnetic field magnitude along a respective axis.

In one or more embodiments, the first planar electromagnet coil set, the second planar electromagnet coil set, and the third planar electromagnet coil set are stacked. In one or more embodiments, the first planar electromagnet coil set includes a clockwise spiral winding and a counterclockwise spiral winding that are disposed adjacent to each other. In one or more embodiments, the clockwise spiral winding and the counterclockwise spiral winding are each formed by a respective wire. In one or more embodiments, the clockwise spiral winding and the counterclockwise spiral winding are each elongated in a direction parallel to the second axis, the clockwise spiral winding and the counterclockwise spiral winding each have an axis of symmetry that is parallel to the first axis, and the axis of symmetry of the clockwise spiral winding is aligned with the axis of symmetry of the counterclockwise spiral winding. In one or more embodiments, the first planar electromagnet coil set has a width that is parallel to the first axis, and a ratio of (a) the at least a portion of the localization magnetic field gradient that has the monotonically-varying magnetic field magnitude along the first axis to (b) the width of the first planar electromagnet coil set is within a range of about 1:2 to about 3:4. In one or more embodiments, the ratio is about 2:3.

In one or more embodiments, the clockwise spiral winding is a first clockwise spiral winding, the counterclockwise spiral winding is a first counterclockwise spiral winding, and the second planar electromagnet coil set includes a second clockwise spiral winding and a second counterclockwise spiral winding that are disposed adjacent to each other. In one or more embodiments, the first clockwise spiral winding, the second clockwise spiral winding, the first counterclockwise spiral winding, and the second counterclockwise spiral winding are each formed by a respective wire. In one or more embodiments, the first clockwise spiral winding and the first counterclockwise spiral winding are each elongated in a direction parallel to the second axis, the first clockwise spiral winding and the first counterclockwise spiral winding each have an axis of symmetry that is parallel to the first axis, the axis of symmetry of the first clockwise spiral winding is aligned with the axis of symmetry of the first counterclockwise spiral winding, the second clockwise spiral winding and the second counterclockwise spiral winding are each elongated in a direction parallel to the first axis, the second clockwise spiral winding and the second counterclockwise spiral winding each have an axis of symmetry that is parallel to the second axis, and the axis of symmetry of the second clockwise spiral winding is aligned with the axis of symmetry of the second counterclockwise spiral winding.

In one or more embodiments, the first planar electromagnet coil set has a width that is parallel to the first axis, the second planar electromagnet coil set has a length that is parallel to the second axis, a ratio of (a) the at least a portion of the localization magnetic field gradient that has the monotonically-varying magnetic field magnitude along the first axis to (b) the width of the first planar electromagnet coil set is within a range of about 1:2 to about 3:4, and a ratio of (c) the at least a portion of the localization magnetic field gradient that has the monotonically-varying magnetic field magnitude along the second axis to (d) the length of the second planar electromagnet coil set is within a range of about 1:2 to about 3:4. In one or more embodiments, the ratio (a) the at least a portion of the localization magnetic field gradient that has the monotonically-varying magnetic field magnitude along the first axis to (b) the width of the first planar electromagnet coil set is about 2:3, and the ratio of (c) the at least a portion of the localization magnetic field gradient that has the monotonically-varying magnetic field magnitude along the second axis to (d) the length of the second planar electromagnet coil set is about 2:3.

In one or more embodiments, the third planar electromagnet coil set includes a spiral winding having a form of an annulus. In one or more embodiments, the annulus has an outer diameter measured parallel to the first axis, and a ratio of (e) the at least a portion of the localization magnetic field gradient that has the monotonically-varying magnetic field magnitude along the third axis to (f) the outer diameter of the annulus is within a range of about 1:4 to about 2:5. In one or more embodiments, the ratio of (e) the at least a portion of the localization magnetic field gradient that has the monotonically-varying magnetic field magnitude along the third axis to (f) the outer diameter of the annulus is about 1:3.

In one or more embodiments, the controller is configured to provide power simultaneously to only the first and third planar electromagnet coil sets to thereby produce a first localization magnetic field gradient with respect to the first axis. In one or more embodiments, the first localization magnetic field gradient comprises a total magnetic field produced by the first and third planar electromagnet coil sets. In one or more embodiments, the controller is configured to provide power simultaneously to only the second and third planar electromagnet coil sets to thereby produce a second localization magnetic field gradient with respect to the second axis. In one or more embodiments, the second localization magnetic field gradient comprises a total magnetic field produced by the second and third planar electromagnet coil sets. In one or more embodiments, the controller is configured to provide power to only the third planar electromagnet coil set to thereby produce a third localization magnetic field gradient with respect to the third axis. In one or more embodiments, the controller is configured to selectively provide the power according to a predetermined time sequence to encode each localization magnetic field gradient.

Another aspect of the invention is directed to a method for manufacturing comprising: forming a first planar electromagnet coil set configured to produce a first magnetic field gradient with respect to a first axis; forming a second planar electromagnet coil set configured to produce a second magnetic field gradient with respect to a second axis that is orthogonal to the first axis; forming a third planar electromagnet coil set configured to produce a third magnetic field gradient with respect to a third axis that is orthogonal to the first and second axes; vertically arranging the first, second, and third planar electromagnet coil sets along the third axis; and electrically connecting a controller to the first planar electromagnet coil set, the second planar electromagnet coil set, and the third planar electromagnet coil set, the controller configured to selectively provide power to the first planar electromagnet coil set, the second planar electromagnet coil set, and/or the third planar electromagnet coil set to produce a localization magnetic field gradient with respect to each of the first, second, and third axes, at least a portion of each localization magnetic field gradient having a monotonically-varying magnetic field magnitude along a respective axis.

In one or more embodiments, forming the first planar electromagnet coil set comprises: forming a first clockwise spiral winding with a first wire, the first clockwise spiral winding having an axis of symmetry that is parallel to the first axis; forming a first counterclockwise spiral winding with a second wire, the first counterclockwise spiral winding having an axis of symmetry that is parallel to the first axis; placing the first clockwise spiral winding adjacent to the first counterclockwise spiral winding; and aligning the axis of symmetry of the first clockwise spiral winding with the axis of symmetry of the first counterclockwise spiral winding.

In one or more embodiments, forming the second planar electromagnet coil set comprises: forming a second clockwise spiral winding with a third wire, the second clockwise spiral winding having an axis of symmetry that is parallel to a second axis that is orthogonal to the first axis; forming a second counterclockwise spiral winding with a fourth wire, the second counterclockwise spiral winding having an axis of symmetry that is parallel to the second axis; placing the second clockwise spiral winding adjacent to the second counterclockwise spiral winding; and aligning the axis of symmetry of the second clockwise spiral winding with the axis of symmetry of the second counterclockwise spiral winding.

In one or more embodiments, forming the third planar electromagnet coil set comprises forming a spiral winding with a fifth wire in a shape of an annulus, the spiral winding having an axis of symmetry that is parallel to a third axis that is orthogonal to the first and second axes.

In one or more embodiments, the method further comprises elongating the first clockwise spiral winding and the first counterclockwise spiral winding in a direction parallel to the second axis. In one or more embodiments, the method further comprises elongating the second clockwise spiral winding and the second counterclockwise spiral winding in a direction parallel to the first axis. In one or more embodiments, the method further comprises vertically stacking the first planar electromagnet coil set, the second planar electromagnet coil set, and the third planar electromagnet coil set.

In one or more embodiments, the method further comprises configuring the controller with a first setting that provides power to only the first planar electromagnet coil set and the third planar electromagnet coil set to produce a first localization magnetic field gradient with respect to the first axis, at least a portion of the first localization magnetic field gradient having a monotonically-varying magnetic field magnitude along the first axis. In one or more embodiments, the method further comprises configuring the controller with a second setting that provides power to only the second planar electromagnet coil set and the third planar electromagnet coil set to produce a second localization magnetic field gradient with respect to the second axis, at least a portion of the second localization magnetic field gradient having a monotonically-varying magnetic field magnitude along the second axis. In one or more embodiments, the method further comprises configuring the controller with a third setting that provides power to only the third planar electromagnet coil set to produce a third localization magnetic field gradient with respect to the third axis, at least a portion of the third localization magnetic field gradient having a monotonically-varying magnetic field magnitude along the third axis. In one or more embodiments, the method further comprises configuring the controller to provide power according to the first, second, and third settings in a predetermined time sequence to encode the respective first, second, and third localization magnetic field gradients.

Another aspect of the invention is directed to a method of producing magnetic field gradients, comprising: electrically connecting a controller to (a) a first planar electromagnet coil set configured to produce a first magnetic field gradient with respect to a first axis, (b) a second planar electromagnet coil set configured to produce a second magnetic field gradient with respect to a second axis, and (c) a third planar electromagnet coil set configured to produce a third magnetic field gradient with respect to a third axis, wherein the first, second, and third axes are orthogonal to one another, wherein the first, second, and third planar electromagnet coil sets are vertically arranged with respect to the third axis; with the controller, providing electrical power simultaneously only to (a) and (c) at a first time; with the controller, providing electrical power simultaneously only to (b) and (c) at a second time that is different than the first time; and with the controller, providing electrical power only to (c) at a third time that is different than the first and second times.

In one or more embodiments, providing electrical power simultaneously only to (a) and (c) comprises producing a first combined magnetic field gradient with respect to the first axis, at least a portion of the first combined magnetic field gradient having a monotonically-varying magnetic field magnitude along the first axis. In one or more embodiments, the first planar electromagnet coil set has a width that is parallel to the first axis, and a ratio of (a) the at least a portion of the first combined magnetic field gradient that has the monotonically-varying magnetic field magnitude along the first axis to (b) the width of the first electromagnet coil set is within a range of about 1:2 to about 3:4.

In one or more embodiments, providing electrical power simultaneously only to (b) and (c) comprises producing a second combined magnetic field gradient with respect to the second axis, the second combined magnetic field gradient having a monotonically-varying magnitude over at least a portion of the second electromagnet coil set. In one or more embodiments, the second planar electromagnet coil set has a length that is parallel to the second axis, and a ratio of (a) the at least a portion of the second combined magnetic field gradient that has the monotonically-varying magnetic field magnitude along the first axis to (b) the length of the second electromagnet coil set is within a range of about 1:2 to about 3:4.

In one or more embodiments, providing electrical power only to (c) comprises producing the third magnetic field gradient, at least a portion of the third magnetic field gradient having a monotonically-varying magnetic field magnitude along the third axis. In one or more embodiments, the annulus has an outer diameter measured parallel to the first axis, and a ratio of (e) the at least a portion of the third magnetic field gradient that has the monotonically-varying magnetic field magnitude along the third axis to (f) the outer diameter of the annulus is within a range of about 1:4 to about 2:5.

In one or more embodiments, the method further comprises repeating the following steps according to a predetermined time sequence: providing electrical power simultaneously only to (a) and (c) at the first time, providing electrical power simultaneously only to (b) and (c) at the second time, and providing electrical power only to (c) at the third time.

Another aspect of the invention is directed to a system comprising: a three-dimensional magnetic field generator configured to sequentially produce: a first magnetic field gradient along a first axis, at least a portion of the first magnetic field gradient having a monotonically-varying magnetic field magnitude along the first axis, a second magnetic field gradient along a second axis that is orthogonal to the first axis, at least a portion of the second magnetic field gradient having a monotonically-varying magnetic field magnitude along the second axis, and a third magnetic field gradient along a third axis that is orthogonal to the first and second axes, at least a portion of the third magnetic field gradient having a monotonically-varying magnetic field magnitude along the third axis; a magnetic sensor device comprising: a three-dimensional magnetic sensor that outputs a measurement of a first, a second, and a third magnetic field corresponding to the first, second, and third magnetic field gradients, respectively; a controller electrically coupled to the three-dimensional magnetic sensor, the controller generating a magnetic sensor output signal that encodes the measurement of the first, second, and third magnetic fields; a device antenna electrically coupled to the controller, the antenna broadcasting the magnetic sensor output signal; and a power source electrically coupled to the three-dimensional magnetic sensor and the controller; and a receiver comprising: a microprocessor; a receiver antenna that receives the magnetic sensor output signal from the device antenna; and non-volatile memory accessible to the microprocessor, the non-volatile memory including computer-readable instructions that, when executed by the processor, cause the microprocessor to determine a three-dimensional position of the magnetic sensor device using the measurement of the first, second, and third magnetic fields.

In one or more embodiments, the non-volatile memory includes a look-up table that includes a plurality of measurements of the first, second, and third magnetic field gradients at known three-dimensional positions.

Another aspect of the invention is directed to a method for determining a relative position of an object using magnetic field gradients, comprising: with a three-dimensional magnetic field generator, sequentially producing: a first magnetic field gradient along a first axis, at least a portion of the first magnetic field gradient having a monotonically-varying magnetic field magnitude along the first axis, the first magnetic field gradient produced at a first time, a second magnetic field gradient along a second axis that is orthogonal to the first axis, at least a portion of the second magnetic field gradient having a monotonically-varying magnetic field magnitude along the second axis, the second magnetic field gradient produced at a second time that is different than the first time, and a third magnetic field gradient along a third axis that is orthogonal to the first and second axes, at least a portion of the third magnetic field gradient having a monotonically-varying magnetic field magnitude along the third axis, the third magnetic field gradient produced at a third time that is different than the first and second times; with a magnetic sensor device comprising a three-dimensional magnetic sensor and a device antenna, measuring a first total magnetic field, at a three-dimensional position of the magnetic sensor device, at the first time; measuring a second total magnetic field, at the three-dimensional position of the magnetic sensor device, at the second time; measuring a third total magnetic field, at the three-dimensional position of the magnetic sensor device, at the third time; and broadcasting a measurement of the first, second, and third total magnetic fields with the device antenna; and with a receiver comprising a microprocessor and a receiver antenna, receiving the measurement of the first, second, and third total magnetic fields with the receiver antenna; and determining the three-dimensional position of the magnetic sensor device using the measurement of the first, second, and third total magnetic fields with the receiver antenna.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

Three-dimensional magnetic field gradients with respect to mutually-orthogonal axes are produced using an apparatus that includes first, second, and third electromagnet coil sets. The first electromagnetic coil set is configured to produce a first magnetic field gradient with respect to a first axis. The second electromagnetic coil set is configured to produce a second magnetic field gradient with respect to a second axis that is orthogonal to the first axis. The third electromagnetic coil set is configured to produce a third magnetic field gradient with respect to a third axis that is orthogonal to the first and second axes.

A controller selectively provides power to the first, second, and/or third electromagnet coil sets to produce a localization magnetic field gradient, with respect to each axis, where at least a portion of each localization magnetic field gradient has a monotonically-varying magnetic field magnitude along the respective axis. The controller can produce the localization magnetic field gradients in a predetermined time sequence to encode the localization magnetic field gradients. The portion of the localization magnetic field gradient that has a monotonically-varying magnitude can represent a field of view (FOV) of the apparatus. In the FOV, the monotonically-varying magnitude of each magnetic field gradient can correspond a relative position or coordinate with respect to the apparatus. A relative position of a magnetic sensor device can be determined based on the measured magnetic field, by the magnetic sensor device, corresponding to each localization magnetic field gradient.

Micro-scale device localization for high precision surgery holds the potential to replace X-Ray fluoroscopy, which is the current imaging standard during many of these surgeries, a typical example being orthopedic surgery.

Figure 1:
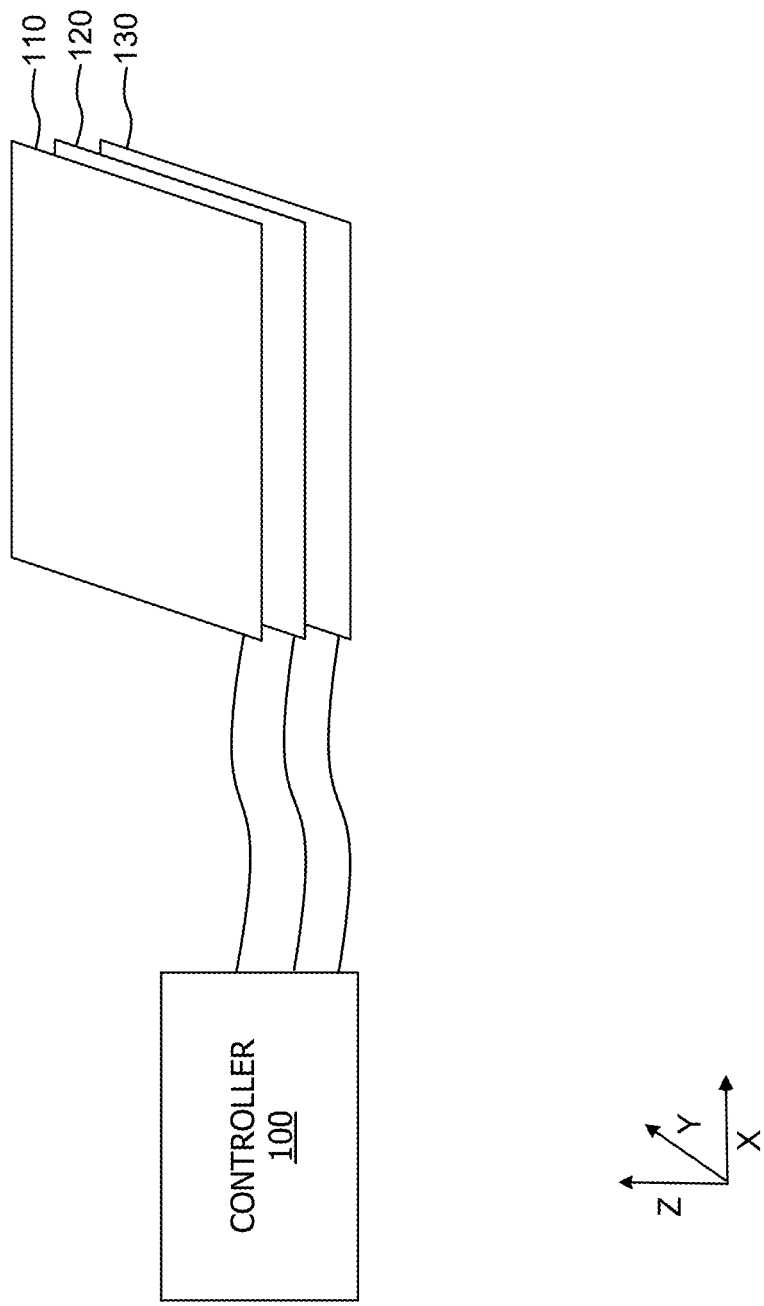
FIG. 1 is a block diagram of an apparatus for producing magnetic field gradients according to an embodiment.

FIG. 1 is a block diagram of an apparatus 10 for producing magnetic field gradients according to an embodiment. The apparatus 10 includes a controller 100, a first electromagnet coil set 110, a second electromagnet coil set 120, and a third electromagnet coil set 130. The first electromagnet coil set 110 is configured to produce a first magnetic field gradient with respect to a first axis (e.g., the X axis in the Cartesian coordinate system). The second electromagnet coil set 120 is configured to produce a second magnetic field gradient with respect to a second axis (e.g., the Y axis in the Cartesian coordinate system) that is orthogonal to the first axis. The third electromagnet coil set 130 is configured to produce a third magnetic field gradient with respect to a third axis (e.g., the Z axis in the Cartesian coordinate system) that is orthogonal to the first and second axes.

The electromagnet coil sets 110, 120, 130 can be stacked together (e.g., in a vertical arrangement with respect to an underlying surface). The electromagnet coil sets 110, 120, 130 are preferably centered (e.g., concentrically centered) and/or aligned, with respect to the first and second axes, with respect to each other. In addition, the electromagnet coil sets 110, 120, 130 each have upper and lower planar surfaces (e.g., orthogonal to the Z axis), which allows them to be stacked and integrated or embedded into a flat device, such as a board, a wall, the back of a chair, a conformable wearable belt, or other location to minimize patient discomfort.

The controller 100 is electrically coupled to the first electromagnet coil set 110, the second electromagnet coil set 120, and the third electromagnet coil set 130. The controller 100 is configured to selectively provide power to the first electromagnet coil set 110, the second electromagnet coil set 120, and/or the third electromagnet coil set 130. Selectively powering the electromagnet coil sets 110, 120, and/or 130 can sequentially produce a total magnetic field gradient, with respect to each axis, that has a monotonically-varying magnitude along some or all of the respective localization magnetic field gradient. For example, the electromagnet coil sets 110, 120, and/or 130 can be selectively powered such that at least a portion of the total magnetic field gradient with respect to the first axis has a monotonically-varying magnitude. In another example, the electromagnet coil sets 110, 120, and/or 130 can be selectively powered such that at least a portion of the total magnetic field gradient with respect to the second axis has a monotonically-varying magnitude. In yet another example, the electromagnet coil sets 110, 120, and/or 130 can be selectively powered such that at least a portion of the total magnetic field gradient with respect to the third axis has a monotonically-varying magnitude. The relative position of a magnetic sensor device, with respect to the electromagnet coil sets 110, 120, and/or 130, can be determined by measuring the total magnetic field while each localization magnetic field gradients is produced. The portion of the total magnetic field gradient with respect to a given axis can be referred to as a field of view (FOV).

Figure 2B:
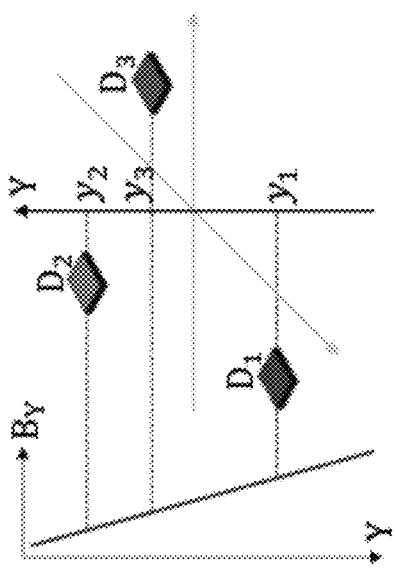
FIGS. 2A, 2B, and 2C are simplified views of the total magnetic field gradients used for encoding the device location.
Figure 2C:
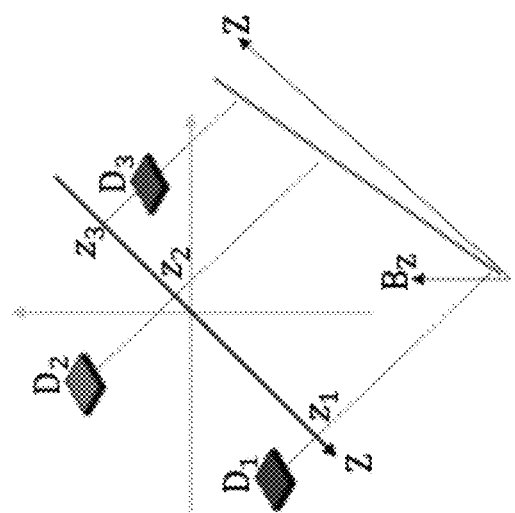
Figure 2A:
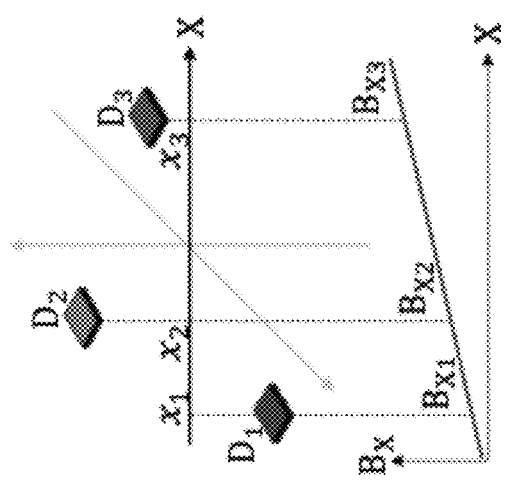

FIGS. 2A-C are simplified views of the total magnetic field gradients used for encoding the device location. Three example magnetic sensor devices $D_1$, $D_2$, and $D_3$ are located in the FOV. To localize the devices $D_1$, $D_2$, and $D_3$ along the X-axis (e.g., the first axis), a magnetic field $B_X$ having a monotonically-varying magnitude is generated with respect to the X-axis, as illustrated in FIG. 2A. The monotonically-varying magnitude has a gradient in the absolute value of the total magnetic field along the X-axis. The gradient ensures that no two points along the X-axis within the FOV have the same absolute total magnetic field value. For example, the magnitude of the total magnetic field $B_X$ measured by devices $D_1$, $D_2$, and $D_3$ can be described according to Equation 1:

$$\|B_{X1}\| < \|B_{X2}\| < \|B_{X3}\| \tag{1}$$

The total magnetic field $B_X$ at each device's X location can be described with respect to the X magnetic field contribution from each orthogonal magnetic field at the corresponding X location, as described in Equation 2. The magnetic field gradient with respect to the X axis can be described according to Equation 3.

$$\|B_{Xi, i=1,2,3}\| = \sqrt{B_{Xi\text{-}x}^2 + B_{Xi\text{-}y}^2 + B_{Xi\text{-}z}^2} \tag{2}$$

$$X \text{ Gradient} = G_X = \partial B_X / \partial X \tag{3}$$

Similarly, to localize the devices $D_1$, $D_2$, and $D_3$ along the Y-axis (e.g., the second axis), a magnetic field By having a monotonically-varying magnitude is generated with respect to the Y-axis, as illustrated in FIG. 2B. The monotonically-varying magnitude has a gradient in the absolute value of the total magnetic field along the Y-axis. The gradient ensures that no two points along the Y-axis within the FOV have the same absolute total magnetic field value. For example, the magnitude of the total magnetic field By measured by devices $D_1$, $D_2$, and $D_3$ can be described according to Equation 4:

$$\|B_{Y2}\| < \|B_{Y3}\| < \|B_{Y1}\| \tag{4}$$

The total magnetic field $B_Y$ at each device's Y location can be described with respect to the Y magnetic field contribution from each orthogonal magnetic field at the corresponding Y location, as described in Equation 5. The magnetic field gradient with respect to the Y axis can be described according to Equation 6.

$$\|B_{Yi, i=1,2,3}\| = \sqrt{B_{Yi\text{-}x}^2 + B_{Yi\text{-}y}^2 + B_{Yi\text{-}z}^2} \tag{5}$$

$$Y \text{ Gradient} = G_Y = \partial B_Y / \partial Y \tag{6}$$

Likewise, to localize the devices $D_1$, $D_2$, and $D_3$ along the Z-axis (e.g., the third axis), a magnetic field $B_Z$ having a monotonically-varying magnitude is generated with respect to the Z-axis, as illustrated in FIG. 2C. The monotonically-varying magnitude has a gradient in the absolute value of the total magnetic field along the Z-axis. The gradient ensures that no two points along the Z-axis within the FOV have the same absolute total magnetic field value. For example, the magnitude of the total magnetic field $B_Z$ measured by devices $D_1$, $D_2$, and $D_3$ can be described according to Equation 7:

$$\|B_{Z1}\| < \|B_{Z2}\| < \|B_{Z3}\| \tag{7}$$

The total magnetic field $B_Z$ at each device's Z location can be described with respect to the Z magnetic field contribution from each orthogonal magnetic field at the corresponding Z location, as described in Equation 8. The magnetic field gradient with respect to the Y axis can be described according to Equation 9.

$$\|B_{Zi, i=1,2,3}\| = \sqrt{B_{Zi,x}^2 + B_{Zi,y}^2 + B_{Zi,z}^2} \tag{8}$$

$$Z\ Gradient = G_Z = \partial B_Z / \partial Z \tag{9}$$

Using these magnetic field measurements along three orthogonal axes, the complete 3D position of each device $D_1$, $D_2$, and $D_3$ can be decoded unambiguously. Since the gradient manifests in the total and absolute magnetic field values along any axis, this localization technique is immune to potential inaccuracies caused by device mis-alignment and orientation mis-match relative to any specific coordinate. As the device orientation changes, the individual field components in Equations 2, 5, and 8 may change but the overall magnitude remains the same.

In order to generate the required spatial gradients in the magnetic field along the three axes, electromagnetic coils (e.g., electromagnet coil sets 110, 120, and/or 130) can be designed with one or more of the following design goals: (i) high gradient strength G to achieve high resolution; (ii) planar or substantially planar coils that can be placed close to the patient, such as beneath or in the patient's bed; (iii) enhanced FOV to allow sufficient room for medical procedure navigation, observation, and/or alignment; (iv) high current efficiency to make the maximum use of current drawn by the gradient coils; and/or (v) low coil-length to have less inductance (for fast switching) and less resistance (for lower heating). The gradient coil efficiency η is defined as the ratio of the magnetic field gradient (G) produced by the coil to the current drawn (I). The geometrical design of the coils and static magnetic field simulations can be carried out in a magneto-static software such as Radia, available from the European Synchrotron Radiation Facility. The FOV can be 15 cm×15 cm×10 cm (X×Y×Z) though other FOVs can be provided.

The spatial localization resolution (αx) obtained by the system is given by Equation 10:

$$\Delta x = \Delta B_{eff}/G \tag{10}$$

where $\Delta B_{eff}$ is the effective resolution that the magnetic sensor can achieve while performing a magnetic field measurement. It is dictated by the noise of the sensing and processing units, most dominant being the quantization noise. G is the applied magnetic field gradient, which is determined by the current in electromagnets and their geometrical structure. There are two predominant noise sources that can cause G to vary from the required ideal value: (a) the offset due to variations in supply current, denoted by $\delta G_s$ and (b) the interpolation error caused during gradient characterization, denoted by $\delta G_i$. To get $\Delta x < 100$ μm with G=30 mT/m, it is required to have $\Delta B_{eff} < 3$ μT. To keep G consistently at 30 mT/m, $\delta G_s + \delta G_i$ are targeted to be <1%. In other embodiments, a lower resolution can be provided (e.g., $\Delta x < 500$ μm).

Figure 3:
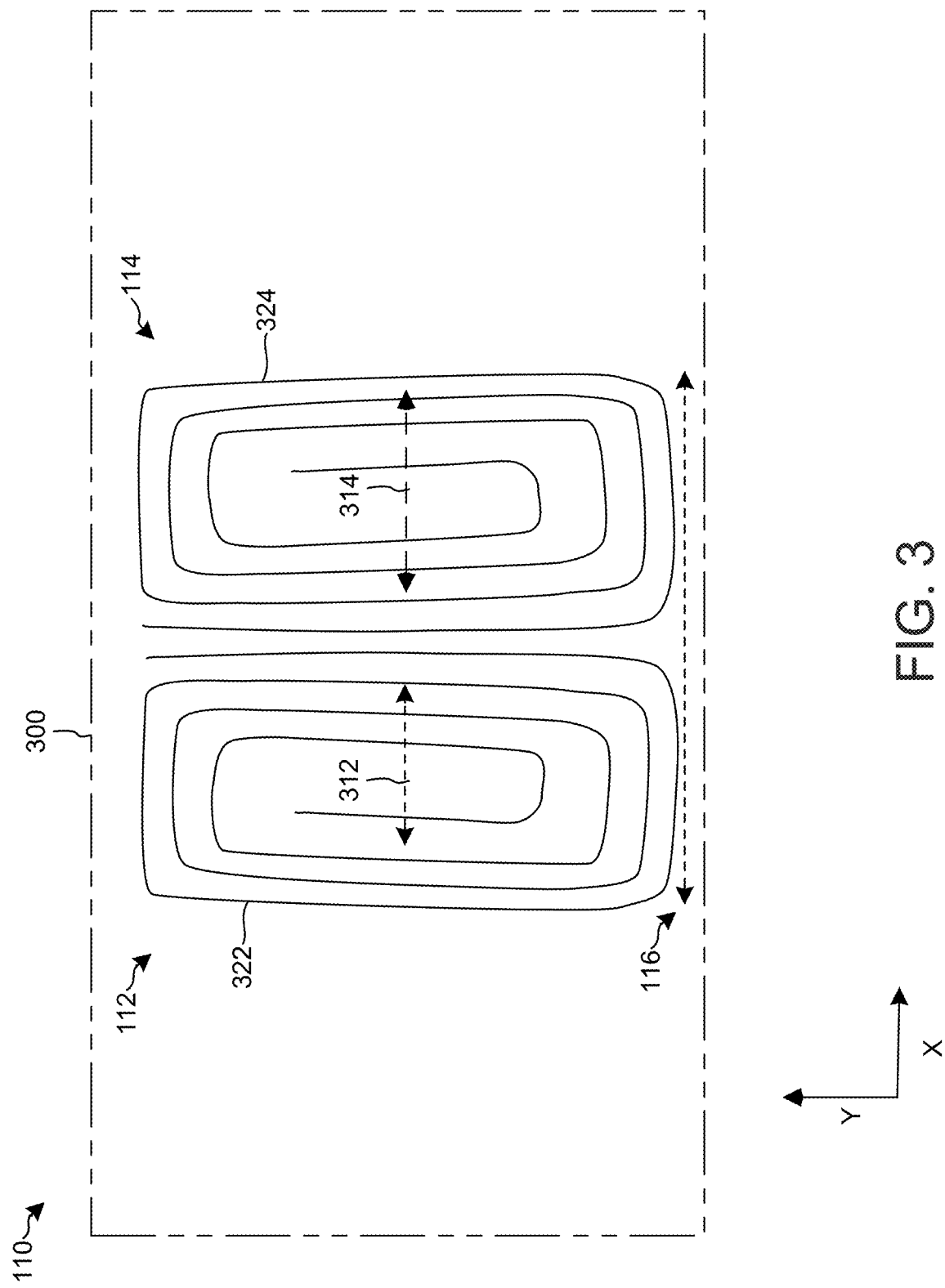
FIG. 3 is a schematic top view of the first electromagnet coil set according to an embodiment.

FIG. 3 is a schematic top view of the first electromagnet coil set 110 according to an embodiment. The first electromagnet coil set 110 includes a clockwise spiral winding 112 and a counterclockwise spiral winding 114 that are disposed adjacent to or next to each other. The spiral windings 112, 114 can be mirror images of each other. Each spiral winding 112, 114 has an axis of symmetry 312, 314 that is parallel to the first axis (e.g., the X axis). The axes of symmetry 312, 314 are aligned in the spiral windings 112, 114 to produce a uniform or substantially uniform magnetic field gradient (e.g., a first magnetic field gradient) with respect to the first axis. The spiral windings 112, 114 are elongated along the second axis (e.g., the Y axis), such as to form ovals, racetracks (e.g., stadium shapes), rectangles, rounded rectangles, or other elongated shapes. The spiral windings 112, 114 can have an elongated length of about 15 cm along the second Y axis which can keep the X-gradient substantially homogenous across the Y FOV. The width 116 of the first electromagnet coil set 110 is measured along or parallel to the first axis (e.g., the X axis). As used herein, "about" means plus or minus 10% of the relevant value.

The spiral windings 112, 114 are formed by respective wires 322, 324 (e.g., first and second wires). Alternatively, more than one wire can be connected together to form a spiral winding. The spiral windings 112, 114 have a thickness (e.g., a profile) defined by the thickness of the respective wires 322, 324. The wires 322, 324 can be identical and thus have the same thickness. Thus, the spiral windings 112, 114 have top and bottom planar surfaces (or substantially planar surfaces (e.g., at least 95% planar)) that are parallel to X-Y plane 300. The top and bottom planar surfaces of the spiral windings 112, 114 are defined by the respective top and bottom surfaces of wires 322, 324. The thickness of the spiral windings 112, 114 with respect to the third axis (e.g., the Z axis) is equal to the thickness of the wires 322, 324. The wires 322, 324 can have an appropriate number of windings or turns to produce the first magnetic field gradient.

The wires 322, 324 can be configured to receive a DC current in the range of about 10 A to about 50 A, including about 20 A, about 30 A, and about 40 A, or another current. For example, the wires 322, 324 can be copper wires such as Litz 50/32 AWG wires, which denotes 50 strands of 32 AWG wires bundled together. The wires 322, 324 have an insulated covering to prevent electrical shorting therebetween.

Figure 4:
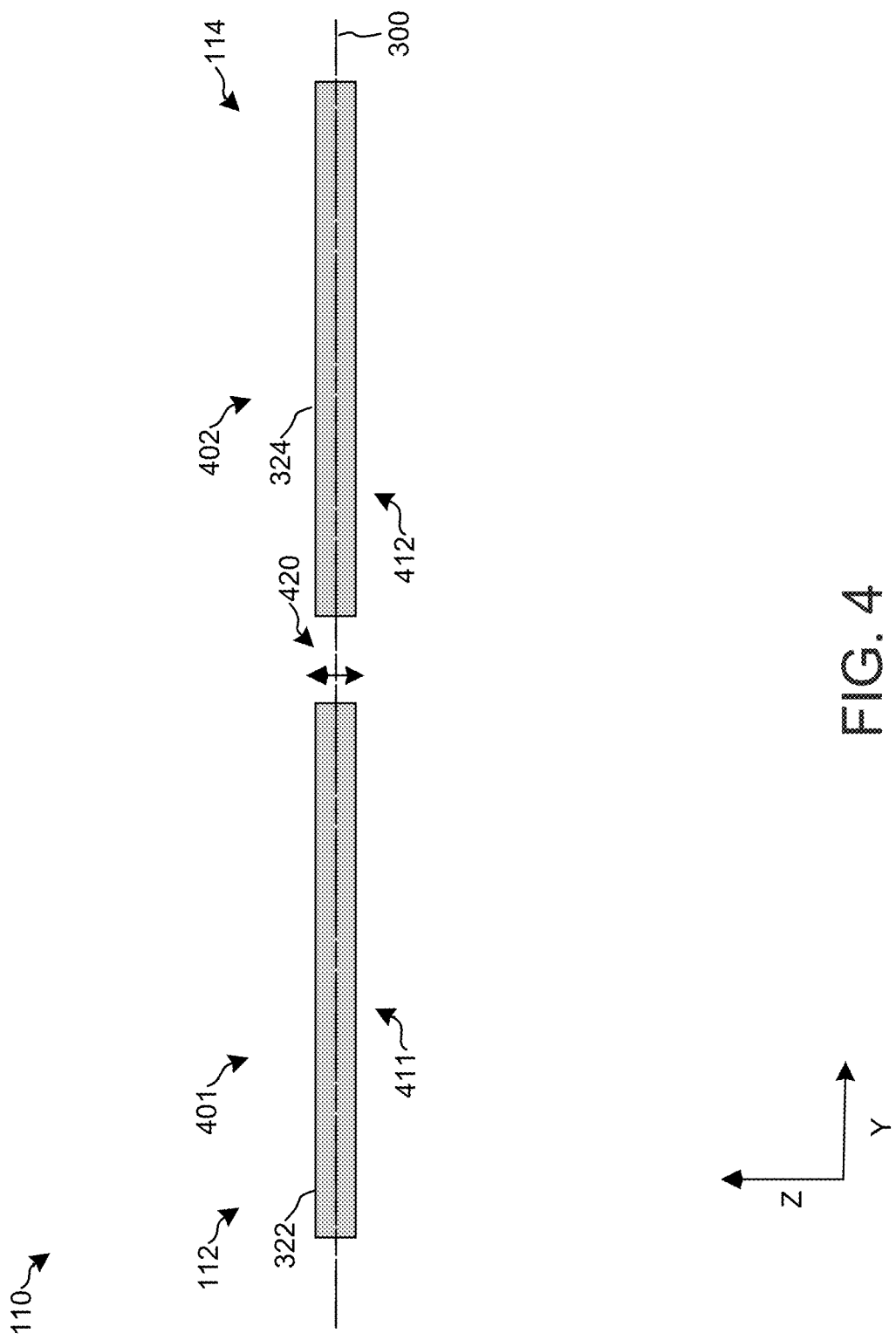
FIG. 4 is a side view of the first electromagnet coil set illustrated in FIG. 3.

FIG. 4 is a side view of the first electromagnet coil set 110 along the second axis. The side view further illustrates that the spiral windings 112, 114 have planar top surfaces 401, 402 and planar bottom surfaces 411, 412, respectively, which are parallel to the X-Y plane 300. The thickness 420 of the spiral windings 112, 114, measured with respect to the third axis (e.g., the Z axis), is equal to the thickness of wires 322, 324. The thickness 420 can be about 0.5 mm to about 1.5 mm in some embodiments.

Figure 5:
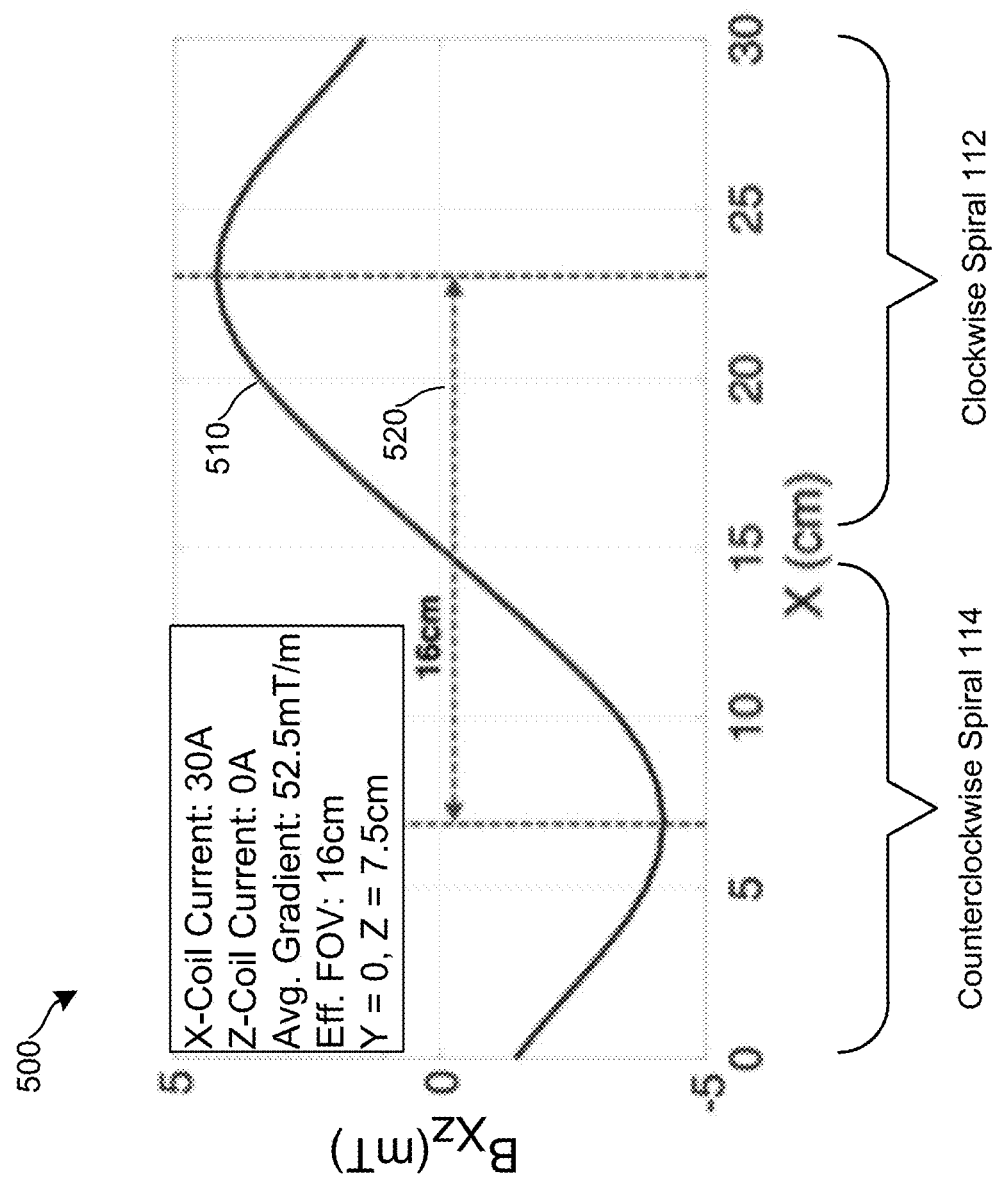
FIG. 5 is a graph that illustrates an example of the Z-component of the magnetic field produced by the first electromagnet coil set.

FIG. 5 is a graph 500 that illustrates an example of the Z-component of the magnetic field 510 produced by the first electromagnet coil set 110. The magnetic field 510 produced by the clockwise spiral winding 112 is negative (e.g., between about −4.5 mT and 0) and the magnetic field 510 produced by the counterclockwise spiral winding 114 is positive (e.g., between 0 and about 4.5 mT). The magnetic field 510 is 0 between the clockwise spiral winding 112 and the counterclockwise spiral winding 114.

In other words, the clockwise current-carrying half (left side of graph 500), produced by the clockwise spiral winding 112, produces a magnetic field $B_X$ that has a Z-component ($B_{Xz}$) pointing into the plane (e.g., plane 300), denoted by negative values. The counter-clockwise current-carrying half (right side of graph 500), produced by the counterclockwise spiral winding 114, produces $B_{Xz}$ pointing out of the plane (e.g., plane 300), denoted by positive values. This creates a monotonically-varying Z-component of the magnetic field 510 (along X-axis) between the centers of the two coils 112, 114, in region 520 of graph 500. The average gradient of magnetic field 510 ($B_{Xz}$) is about 52.5 mT/m.

Figure 6:
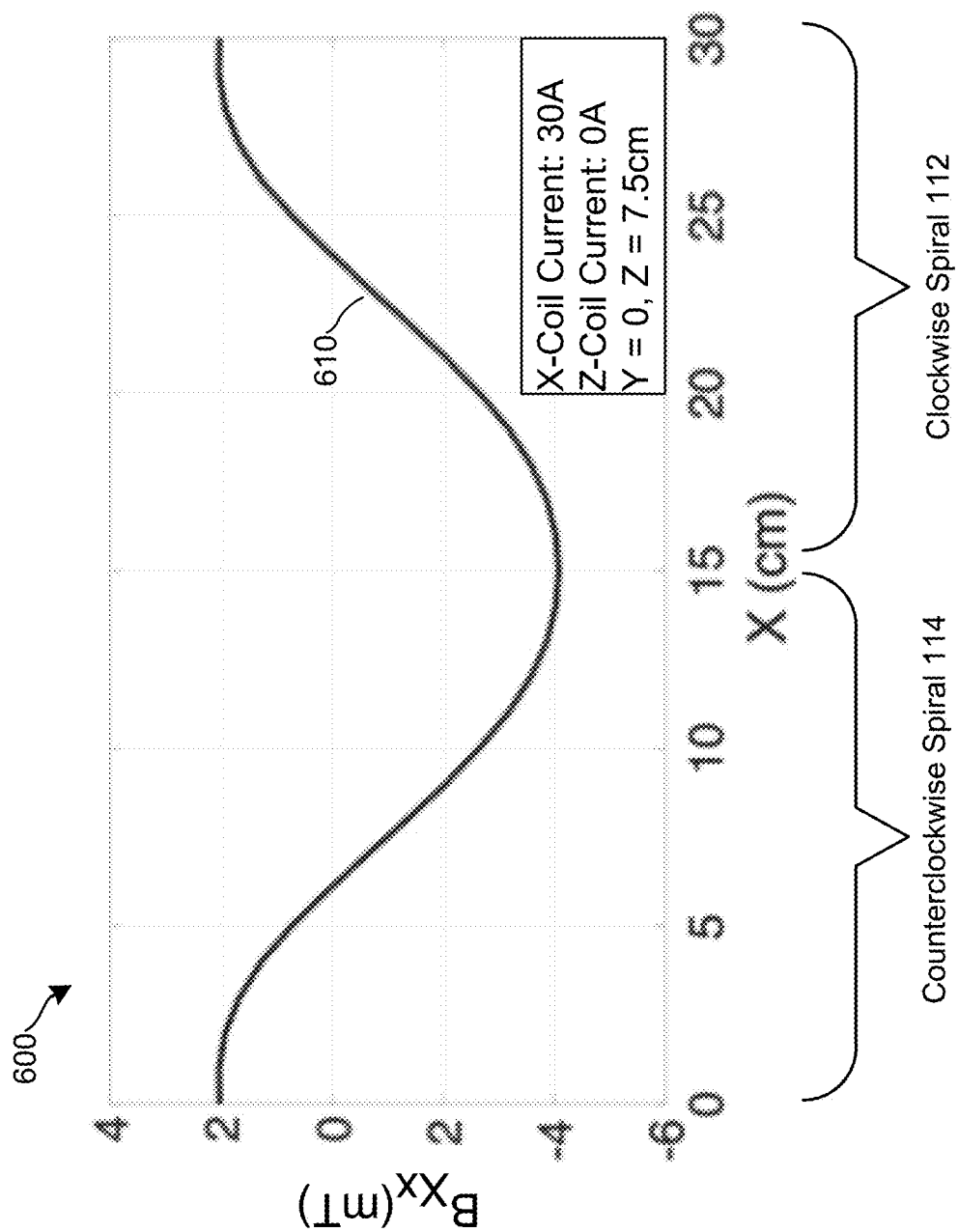
FIG. 6 is a graph that illustrates an example of the X-component of the magnetic field ($B_{Xx}$) produced by the first electromagnet coil set.

FIG. 6 is a graph 600 that illustrates an example of the X-component of the magnetic field 610 ($B_{Xx}$) produced by the first electromagnet coil set 110. The Y-component of the magnetic field ($B_{Xy}$) produced by the first electromagnet coil set 110 at Y=0 cm and Z=7.5 cm iso.

Figure 7:
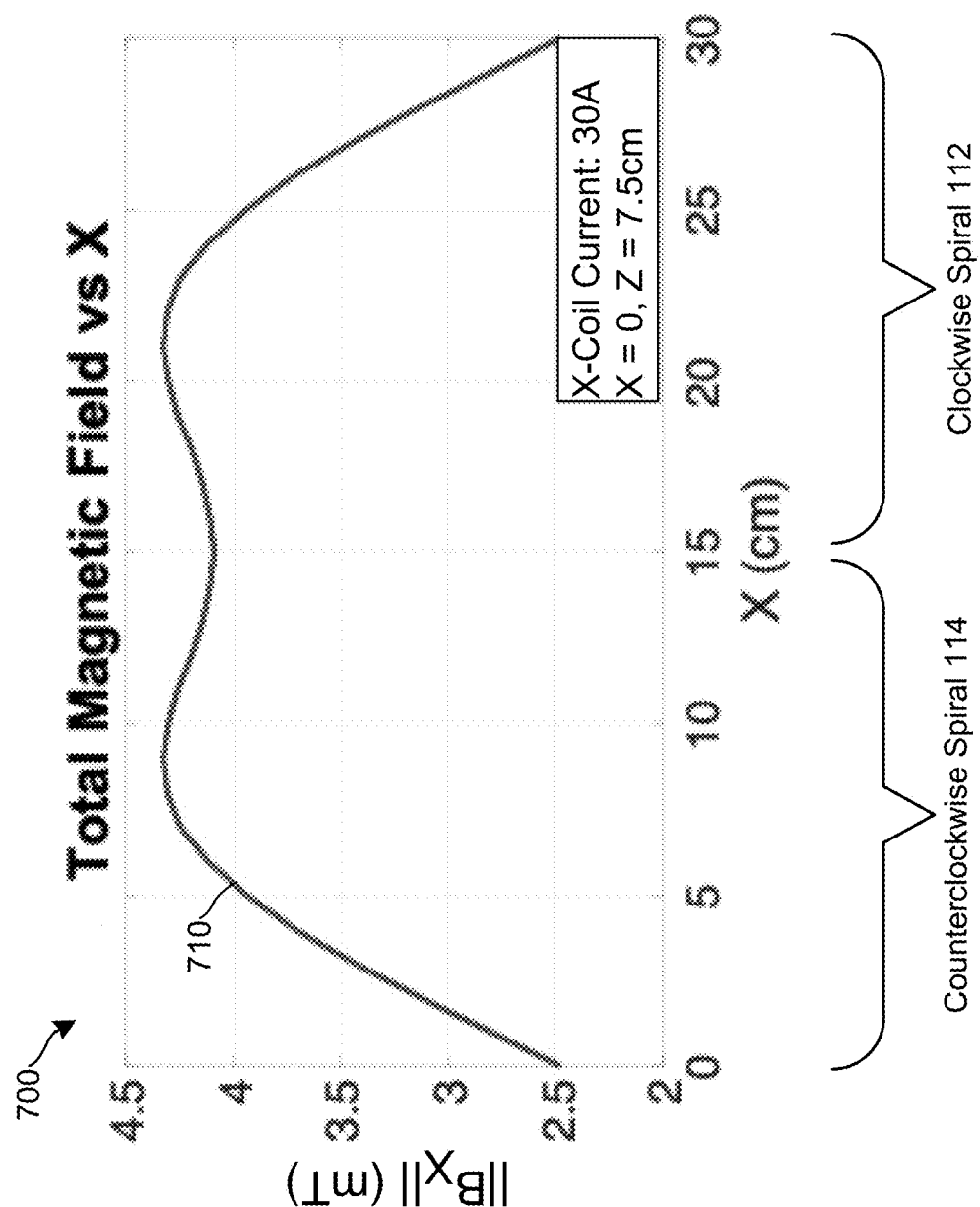
FIG. 7 is a graph that illustrates an example of the total magnetic field ($\|B_X\|$) produced by the first electromagnet coil set.

FIG. 7 is a graph 700 that illustrates an example of the total magnetic field 710 ($\|B_X\|$) produced by the first electromagnet coil set 110. As can be seen, the total magnetic field 710 is highly non-linear.

FIG. 5 shows that the Z-component ($B_{Xz}$) of the magnetic field produced by the first electromagnet coil set 110 is highly monotonic and linear in the central region (e.g., region 520). FIG. 6 region 520 that the X-component ($B_{Xx}$) of the magnetic field produced by the first electromagnet coil set 110 is non-monotonic and non-linear in the central region. As a result, when the magnitude of the total field ($\sqrt{B_{Xx}^2+B_{Xy}^2+B_{Xz}^2}$) is plotted in FIG. 7, a highly non-monotonic and non-linear magnetic field profile is obtained. The non-linearity of total magnetic field 710 can be attributed to: (a) the addition of non-zero and non-linear X and Y components to the Z-component of the magnetic field and (b) non-linearity of the magnitude function which flips the negative half of the total field to result in an even-function centered at X=15 cm (between the coils 112, 114).

In each graph 500, 600, 700, the respective magnetic fields 510, 610, 710 were produced with a DC current of 30 A passing through the spiral windings 112, 114 in the same direction. The respective magnetic fields 510, 610, 710 were measured at a relative Y position of 0 cm, a relative Z position of 7.5 cm, and at varying relative X positions.

Figure 8:
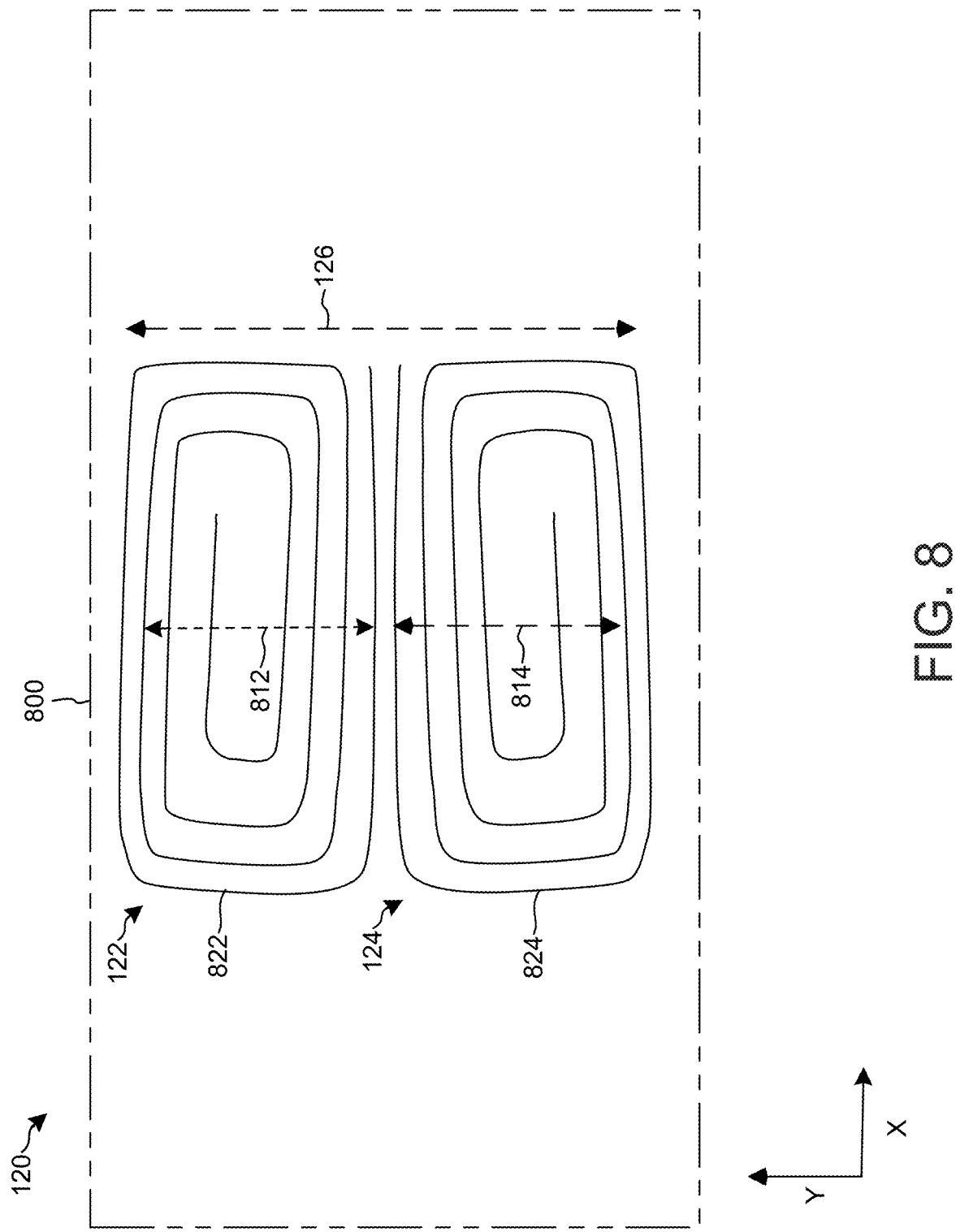
FIG. 8 is a schematic top view of the second electromagnet coil set according to an embodiment.

FIG. 8 is a schematic top view of the second electromagnet coil set 120 according to an embodiment. The second electromagnet coil set 120 includes a clockwise spiral winding 122 and a counterclockwise spiral winding 124 that are disposed adjacent to or next to each other. The spiral windings 122, 124 can be mirror images of each other. Each spiral winding 122, 124 has an axis of symmetry 812, 814 that is parallel to the second axis (e.g., the Y axis). The axes of symmetry 812, 814 are aligned in the spiral windings 122, 124 to produce a uniform or substantially uniform magnetic field gradient (e.g., a second magnetic field gradient) with respect to the second axis. The second electromagnet coil set 120 is the same as the first electromagnet coil set 110 except that the second electromagnet coil set 120 is rotated by 90 degrees compared to the first electromagnet coil set 110. In other embodiments, the second electromagnet coil set 120 can have other configuration differences compared to the first electromagnetic coil set 110.

The spiral windings 122, 124 are formed by respective wires 822, 824 (e.g., third and fourth wires). Alternatively, more than one wire can be connected together to form a spiral winding. The spiral windings 122, 124 have a thickness (e.g., a profile) defined by the thickness of the respective wires 822, 824. The wires 822, 824 can be identical and thus have the same thickness. Thus, the spiral windings 122, 124 have top and bottom planar surfaces (or substantially planar surfaces (e.g., at least 95% planar)) that are parallel to X-Y plane 800. The top and bottom planar surfaces of the spiral windings 122, 124 are defined by the respective top and bottom surfaces of wires 822, 824. The thickness of the spiral windings 122, 124 with respect to the third axis (e.g., the Z axis) is equal to the thickness of the wires 822, 824. The wires 822, 824 can have an appropriate number of windings or turns to produce the second magnetic field gradient. The length 126 of the second electromagnet coil set 120 is measured along or parallel to the second axis (e.g., the Y axis).

The wires 822, 824 can be configured to receive a DC current in the range of about 10 A to about 50 A, including about 20 A, about 30 A, and about 40 A, or another current. For example, the wires 822, 824 can be Litz 50/32 AWG wires. The wires 822, 824 can be the same as or different than the respective wires 322, 324.

Figure 9:
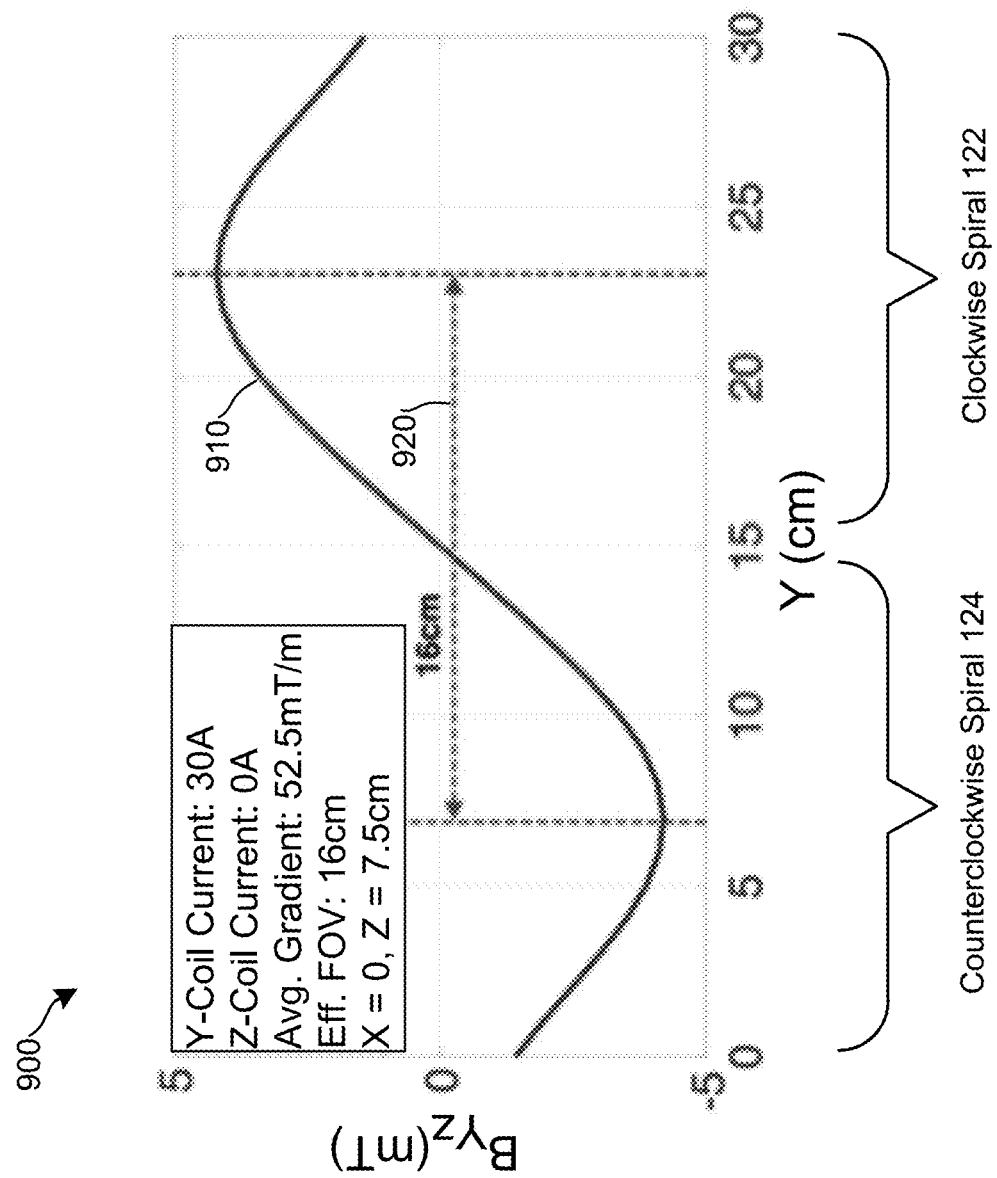
FIG. 9 is a graph that illustrates an example of the Z-component of the magnetic field ($B_{Yz}$) produced by the second electromagnet coil set.

FIG. 9 is a graph 900 that illustrates an example of the Z-component of the magnetic field 910 produced by the second electromagnet coil set 120. The magnetic field 910 produced by the clockwise spiral winding 122 is negative (e.g., between about −4.5 mT and 0) and the magnetic field 910 produced by the counterclockwise spiral winding 124 is positive (e.g., between 0 and about 4.5 mT). The magnetic afield 910 is 0 between the clockwise spiral winding 122 and the counterclockwise spiral winding 124. Graphs 500, 900 are identical for the respective X and Y axes since the first and second coil sets 110, 120 are identical (except a relative rotation of 90°) in this embodiment.

In other words, the clockwise current-carrying half (left side of graph 900), produced by the clockwise spiral winding 122, produces a magnetic field By that has a Z-component ($B_{Yz}$) pointing into the plane (e.g., plane 800), denoted by negative values. The counter-clockwise current-carrying half (right side of graph 900), produced by the counterclockwise spiral winding 124, produces $B_{Yz}$ pointing out of the plane (e.g., plane 800), denoted by positive values. This creates a monotonically-varying Z-component of the magnetic field 910 (along Y-axis) between the centers of the two coils 122, 124, in region 920 of graph 900. The average gradient of magnetic field 910 ($B_{Yz}$) is about 52.5 mT/m.

Figure 10:
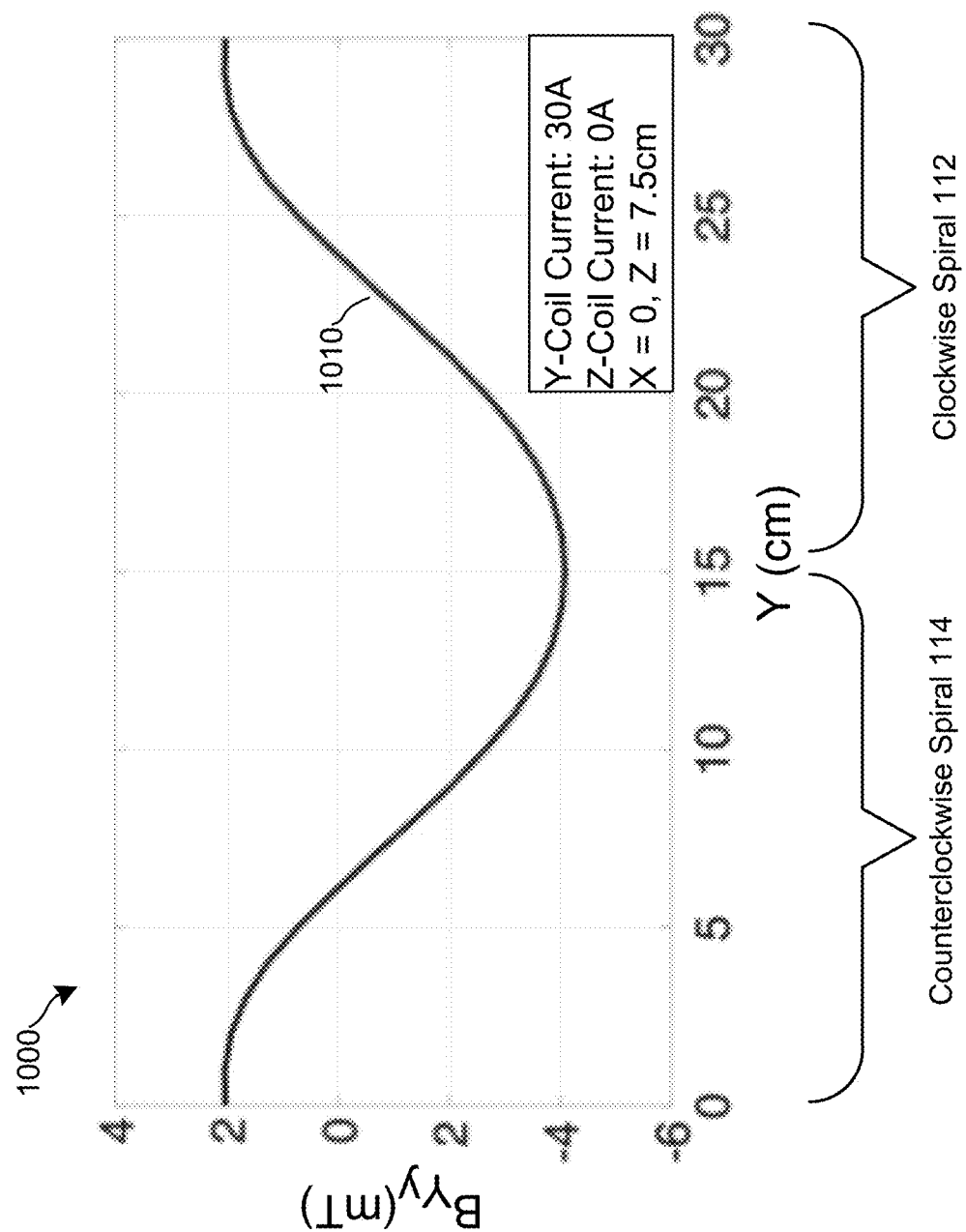
FIG. 10 is a graph that illustrates an example of the Y-component of the magnetic field ($B_{Yy}$) produced by the second electromagnet coil set.

FIG. 10 is a graph 1000 that illustrates an example of the Y-component of the magnetic field 610 ($B_{Yy}$) produced by the second electromagnet coil set 120. The X-component of the magnetic field ($B_{Xy}$) produced by the second electromagnet coil set 120 at X=0 cm and Z=7.5 cm is 0.

Figure 11:
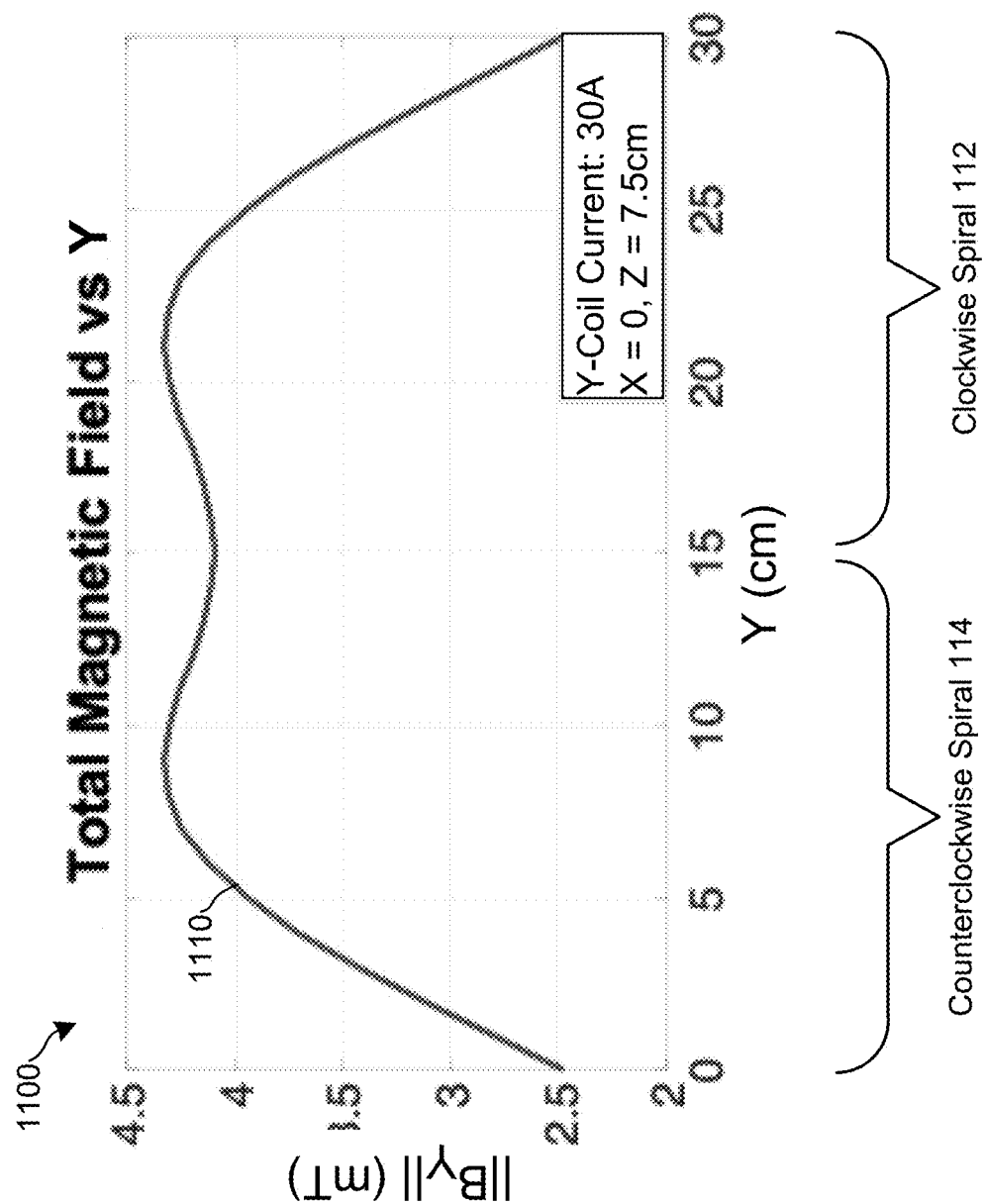
FIG. 11 is a graph that illustrates an example of the total magnetic field ($\|B_Y\|$) produced by the second electromagnet coil set.

FIG. 11 is a graph 1100 that illustrates an example of the total magnetic field 1110 ($\|B_Y\|$) produced by the second electromagnet coil set 120. As can be seen, the total magnetic field 1110 is highly non-linear.

FIG. 9 illustrates that the Z-component ($B_{Yz}$) of the magnetic field produced by the second electromagnet coil set 120 is highly monotonic and linear in the central region (e.g., region 920). FIG. 10 illustrates that the X-component ($B_{Yy}$) of the magnetic field produced by the second electromagnet coil set 120 is non-monotonic and non-linear in the central region. As a result, when the magnitude of the total field ($\sqrt{B_{Yx}^2+B_{Yy}^2+B_{Yz}^2}$) is plotted in FIG. 11, a highly non-monotonic and non-linear magnetic field profile is obtained. The non-linearity of total magnetic field 1110 can be attributed to: (a) the addition of non-zero and non-linear X and Y components to the Z-component of the magnetic field and (b) non-linearity of the modulus function which flips the negative half of the total field to result in an even-function centered at Y=15 cm (between the coils 122, 124).

In each graph 900, 1000, 1100, the respective magnetic fields 910, 1010, 1110 were produced with a DC current of 30 A passing through the spiral windings 122, 124 in the same direction. The respective magnetic fields 910, 1010, 1110 were measured at a relative X position of 0 cm, a relative Z position of 7.5 cm, and at varying relative Y positions.

Figure 12:
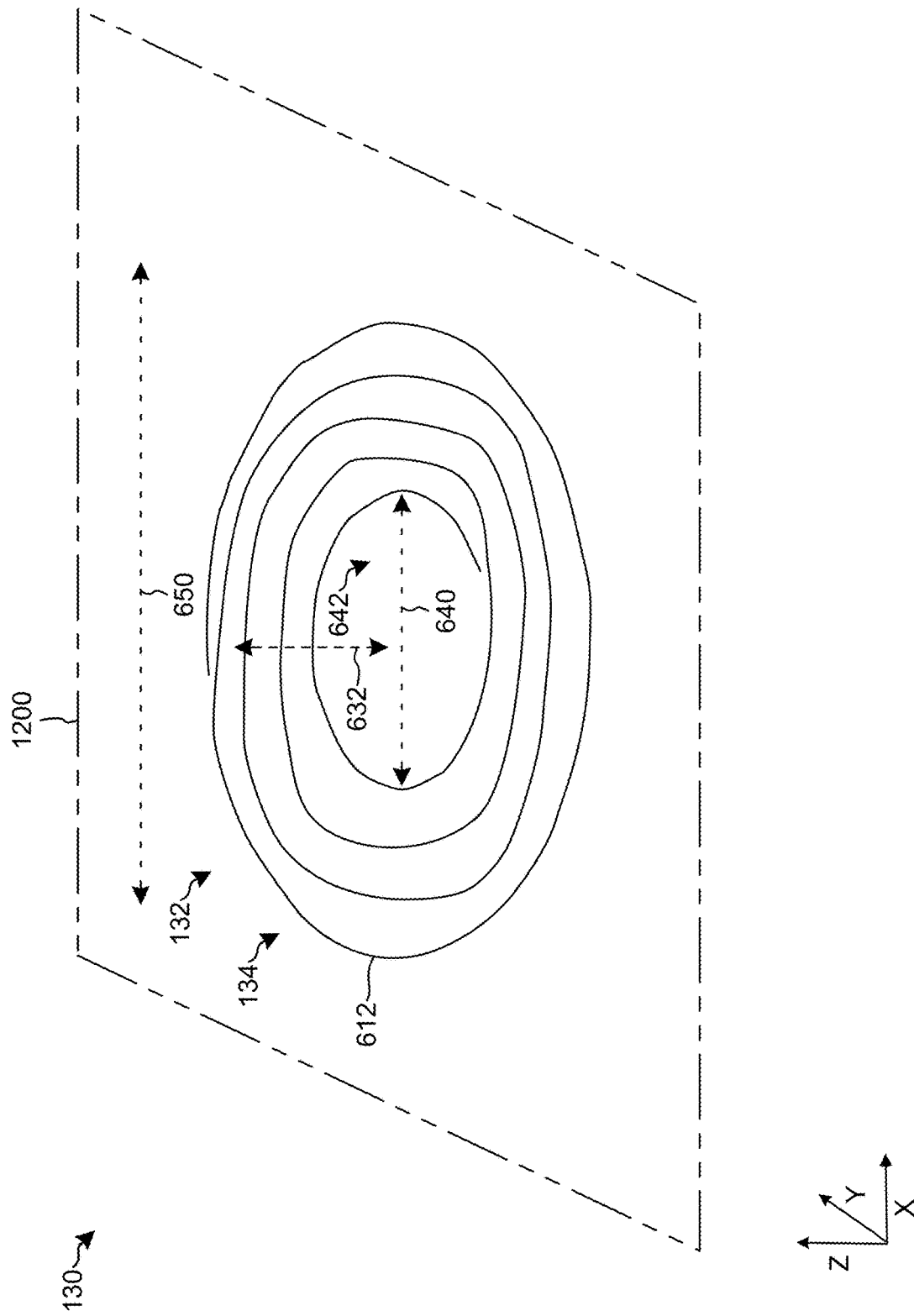
FIG. 12 is a schematic perspective view of the third electromagnet coil set according to an embodiment.

FIG. 12 is a schematic perspective view of the third electromagnet coil set 130 according to an embodiment. The third electromagnet coil set 130 includes a spiral winding 132 that includes one or more wires 612 that is/are wound in the shape of an annulus, disc, or ring 134 (in general, annulus). In an embodiment, two or more wires 612 are wound next to each other to form the annulus 134. The wire(s) 612 are wound in a counter-clockwise direction but in other embodiments the wire(s) 612 can be wound in a clockwise direction.

The annulus 134 has an inner diameter 640 and an outer diameter 650, where the inner diameter 650 defines a hollow region or inner cavity 642 that does not include the wire(s) 612. The ratio of the outer diameter 650 to the inner diameter 640 can be selected to allow an appropriate number of windings or turns of the wire(s) 612, to produce the third magnetic field gradient. In a specific embodiment, the outer diameter 650 can be about 28 cm and the inner diameter 640 can be about 10 cm. The wire(s) 612 have an insulated covering to prevent electrical shorting therebetween. The inner and outer diameters 640, 650 can be measured with respect to or parallel to the first axis (e.g., X axis) or the second axis (e.g., Y axis).

The spiral winding 132 has an axis of symmetry 632 that is parallel to the third axis (e.g., the Z axis). The spiral winding 132 has a thickness (e.g., a profile) defined by the thickness of the wire(s) 612. Thus, the spiral winding 132 has top and bottom planar surfaces (or substantially planar surfaces (e.g., at least 95% planar)) that are parallel to X-Y plane 1200. The top and bottom planar surfaces of the spiral winding 132 are defined by the respective top and bottom surfaces of wire(s) 612. The thickness of the spiral winding 132 with respect to the third axis (e.g., the Z axis) is equal to the thickness of the wire(s) 612. The wire(s) 612 can have an appropriate number of windings or turns to produce the third magnetic field gradient.

The wire(s) 612 can be configured to receive a DC current in the range of about 10 A to about 50 A, including about 20 A, about 30 A, and about 40 A, or another current. For example, the wires wire(s) 612 can be Litz 50/32 AWG wires. The wire(s) 612 can be the same as or different than wires 322, 324, 822, and/or 824.

Figure 13:
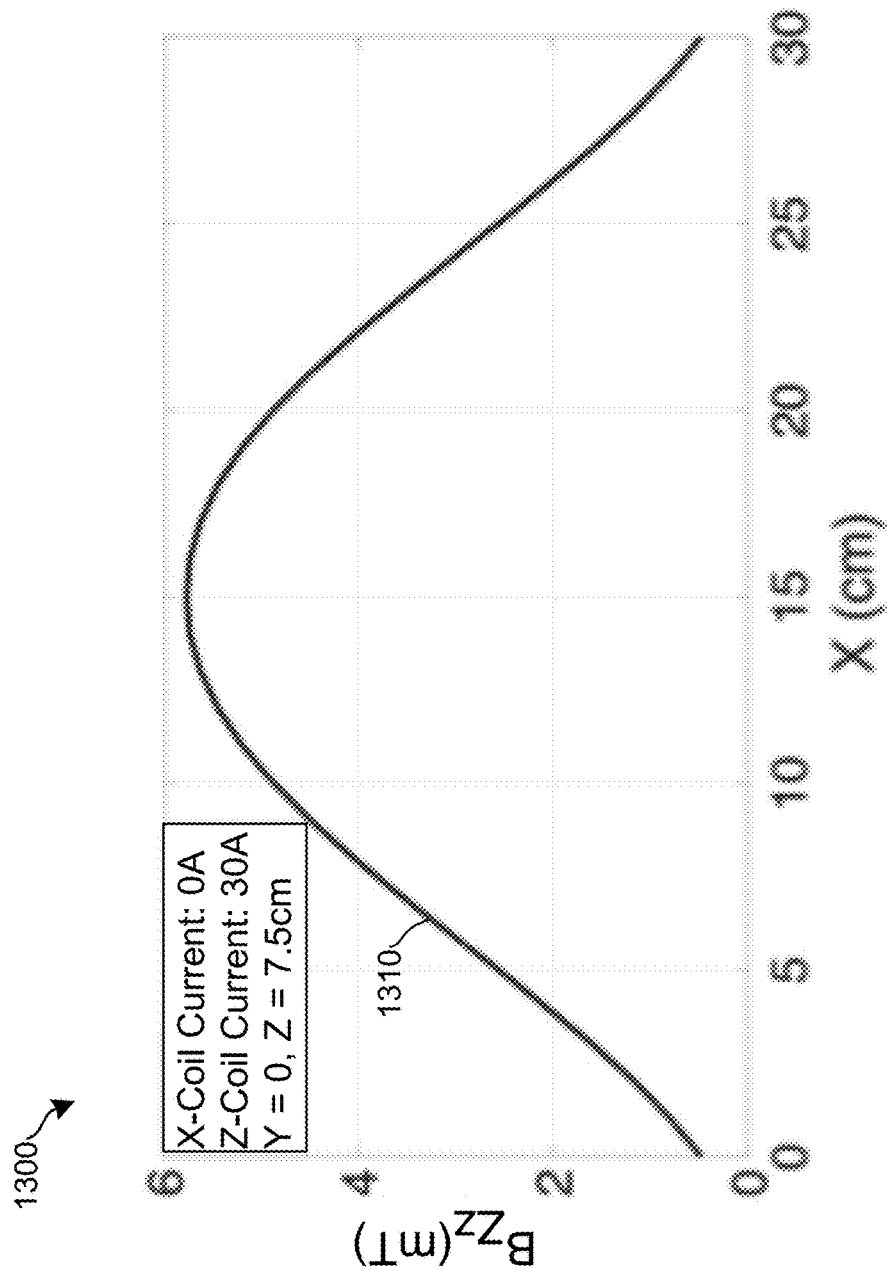
FIG. 13 is a graph that illustrates an example of the Z-component of the magnetic field ($B_{Zz}$) produced by the third electromagnet coil set.

FIG. 13 is a graph 1300 that illustrates an example of the Z-component of the magnetic field 1310 produced by the third electromagnet coil set 130. The magnetic field 1310 is positive at all X positions across the spiral winding 132. As such, the magnetic field $B_Z$ has a Z-component ($B_{Zz}$) pointing out of the plane (e.g., plane 1200), denoted by positive values. The Z-component ($B_{Zz}$) is highest at the center of the spiral winding 132 (e.g., at X=15 cm). The portion of the magnetic field 1310 on either side of the spiral winding's center varies monotonically.

Figure 14:
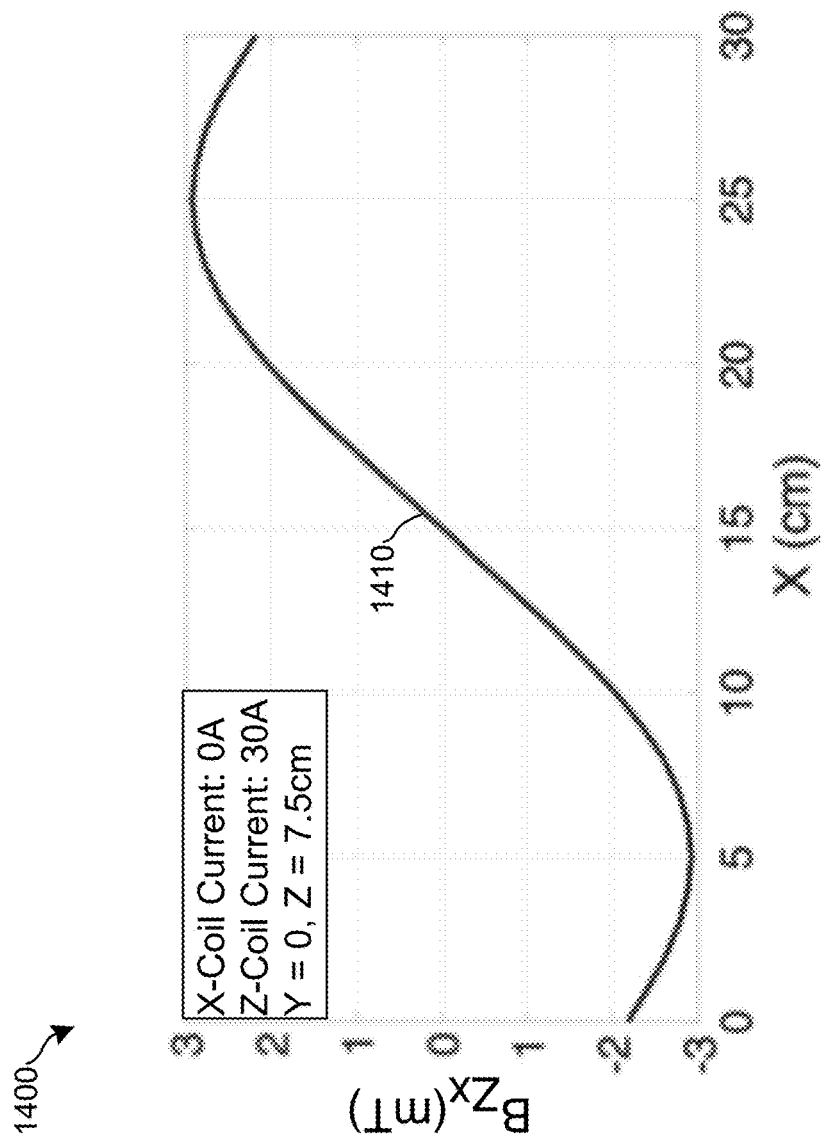
FIG. 14 is a graph that illustrates an example of the X-component of the magnetic field ($B_{Zx}$) produced by the third electromagnet coil set.

FIG. 14 is a graph 1400 that illustrates an example of the X-component of the magnetic field 1410 produced by the third electromagnet coil set 130. The left side of the spiral winding 132 (between X=0 cm and X=15 cm), produces a magnetic field $B_Z$ that has an X-component ($B_{Zx}$) pointing into the plane (e.g., plane 1200), denoted by negative values. The right side of the spiral winding 132 (between X=15 cm and X=30 cm), produces $B_{Zx}$ pointing out of the plane (e.g., plane 1200), denoted by positive values. $B_{Zx}$ is 0 at the center of the spiral winding 132 (e.g., at X=15 cm). $B_{Zx}$ monotonically increases from X=5 cm to X=25 cm.

Since spiral winding 132 is symmetrical with respect to the X and Y axes, the Y-component of the magnetic field produced by the third electromagnet coil set 130 is identical to the X-component of the magnetic field 1410 (e.g., at X=0 cm and at varying Y positions).

In each graph 1300, 1400, the respective magnetic fields 1310, 1410 were produced with a DC current of 30 A passing through the spiral winding 132. The respective magnetic fields 1310, 1410 were measured at a relative Y position of 0 cm, a relative Z position of 7.5 cm, and at varying relative X positions (i.e., where X and Y are switched in graph 1400).

Figure 15:
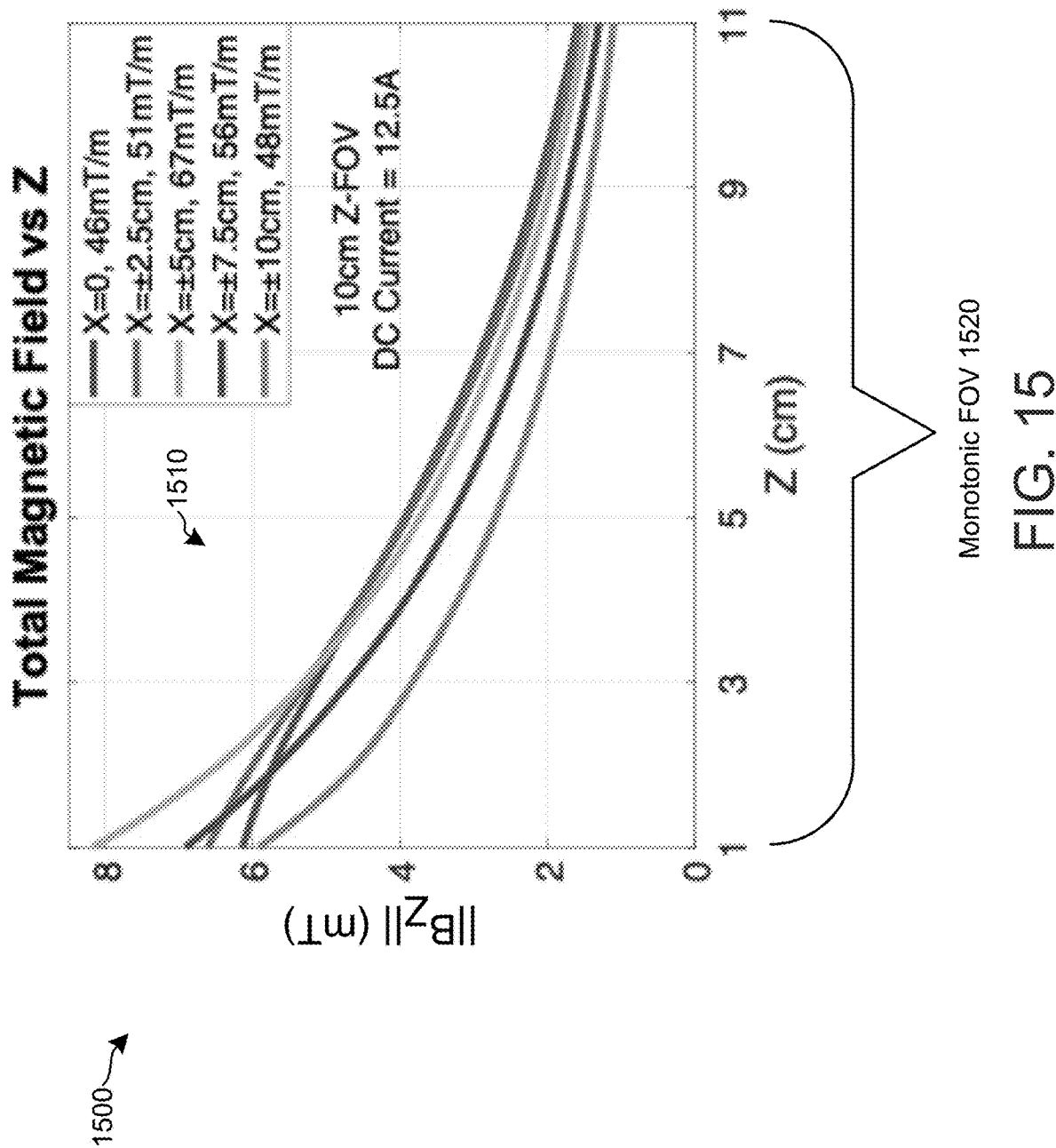
FIG. 15 is a graph that illustrates an example of the monotonically-varying magnetic total fields ($\|B_Z\|$) produced by the third electromagnet coil set.

FIG. 15 is a graph 1500 that illustrates an example of the monotonically-varying magnetic total fields 1510 ($\|B_Z\|$) produced by the third electromagnet coil set 130. Each total magnetic field 1510 plot was measured a respective relative X position as a function of Z position. Each total magnetic field 1510 plot was measured using a relative Y position of 0 cm. In addition, each total magnetic field 1510 was measured over 10 cm from Z=1 cm to Z=11 cm, where the Z distance is the height from the top surface of the third electromagnet coil set 130.

In general, the total magnetic fields 1510 decrease monotonically and with increasing height (Z position) from the third electromagnet coil set 130. In addition, the total magnetic fields 1510 are linear over most heights (Z). It is believed that the inner cavity 642 enhances the linearity of the total magnetic fields 1510, which is more exponential in the absence of the inner cavity 642. The third electromagnet coil set 130 has a monotonic Z FOV 1520 of about 10 cm in which the magnitude of the total magnetic field 1510 varies (decreases) monotonically.

Thus, the ratio of the 10 cm Z FOV 1520 to the outer diameter 650 (30 cm when producing the total magnetic field gradients 1510) of the third magnetic coil set 130 is about 1:3, though the ratio can range from 1:4 to about 2:5 in other embodiments (e.g., less than or equal and/or greater than or equal to 1:3). In addition, the ratio of the 10 cm Z FOV 1520 to the inner diameter 640 (10 cm when producing the total magnetic field gradients 1510) of the third magnetic coil set 130 is about 1:1, though the ratio can range from about 4:5 to about 6:5 in other embodiments (e.g., less than or equal and/or greater than or equal to 1:1).

The gradient strength G is 46 mT/m at X=0 cm, reaches a maximum of 67 mT/m at X=±5 cm, and comes down to 48 mT/m at X=±10 cm, thus ensuring G>30 mT/m over a length of 20 cm along the X-axis. A DC current of 12.5 A was used in the third electromagnet coil set 130 to produce the graph 1500, which results in an average magnetic gradient efficiency η of 4.3 mT/m/A.

Since the spiral winding 132 is symmetrical with respect to the X and Y axes, the total magnetic fields are the same when measured at a relative X position of 0 cm, at relative Y positions of ±2.5 cm, ±5 cm, ±7.5 cm, and ±10 cm, and from Z=1 cm to Z=11 cm (i.e., where X and Y are switched in graph 1500).

It can be seen from graphs 700, 1100, 1500, that the total magnetic field produced by the third magnetic coil set 130 has a monotonically-varying magnitude with respect to the third axis (e.g., Z axis) while the total magnetic field produced by the first and second magnetic coil sets 110, 120 do not have a monotonically-varying magnitude with respect to the first and second axes (e.g., x and Y axes), respectively.

The strictly positive and monotonic nature in either half of $B_{Zz}$ (graph 1300) makes it an appropriate candidate for offsetting the negative half of $B_{Xz}$ (graph 500) and the negative half of $B_{Yz}$ (graph 900). Additionally, $B_{Zx}$ (graph 1400) is highly linear from X=5 cm to X=25 cm, the predominant region of non-linearity in $B_{Xx}$ (graph 600), indicating that a superposition of the two would be relatively more linear than $B_{Xx}$ alone. Likewise, $B_{Zy}$ (identical graph 1400) is highly linear from Y=5 cm to Y=25 cm, the predominant region of non-linearity in $B_{Yy}$ (graph 1000), indicating that a superposition of the two would be relatively more linear than $B_{Yy}$ alone.

Figure 16:
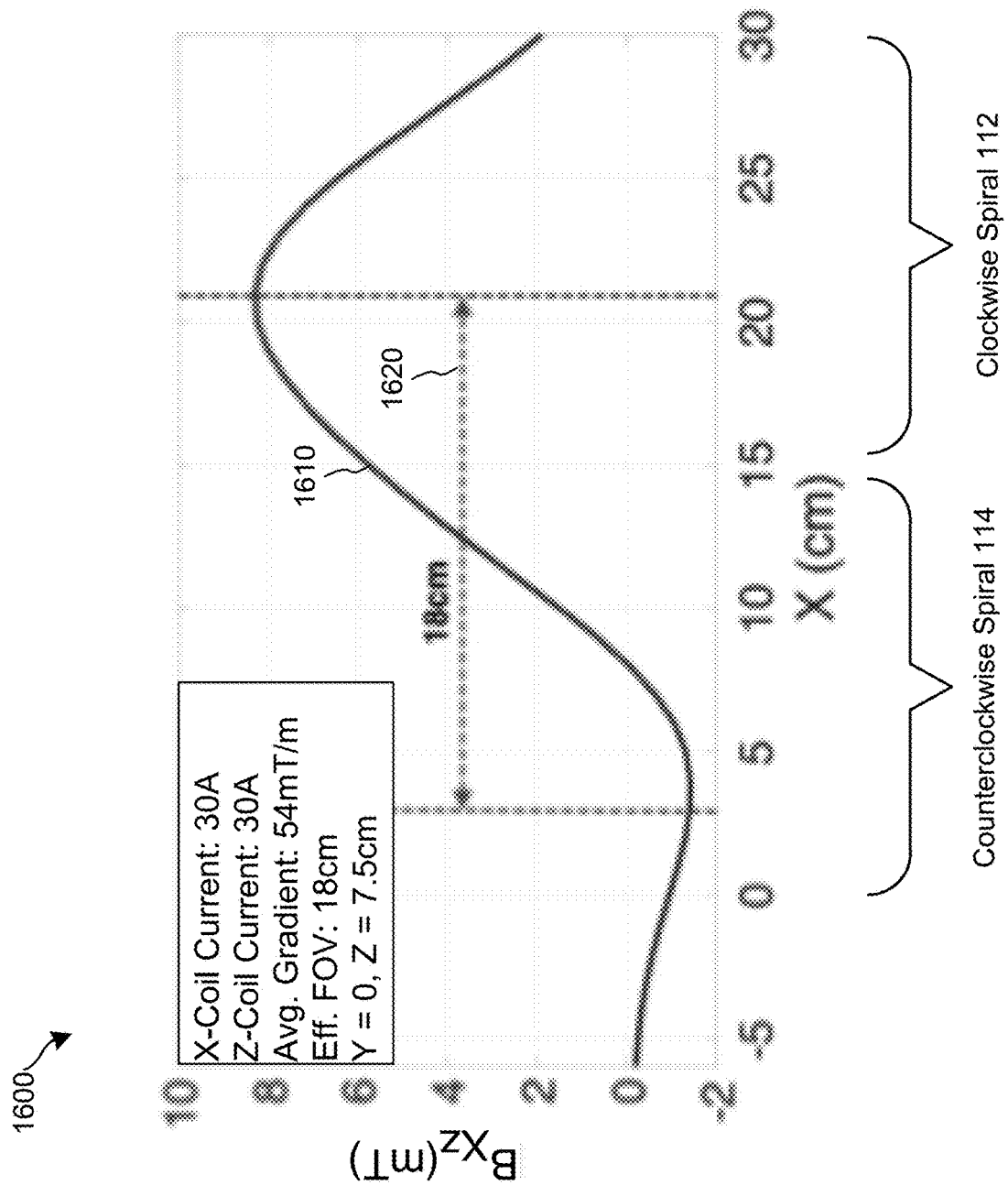
FIG. 16 is a graph that illustrates the Z-component of the combined magnetic field produced simultaneously by the first and third electromagnet coil sets.
Figure 17:
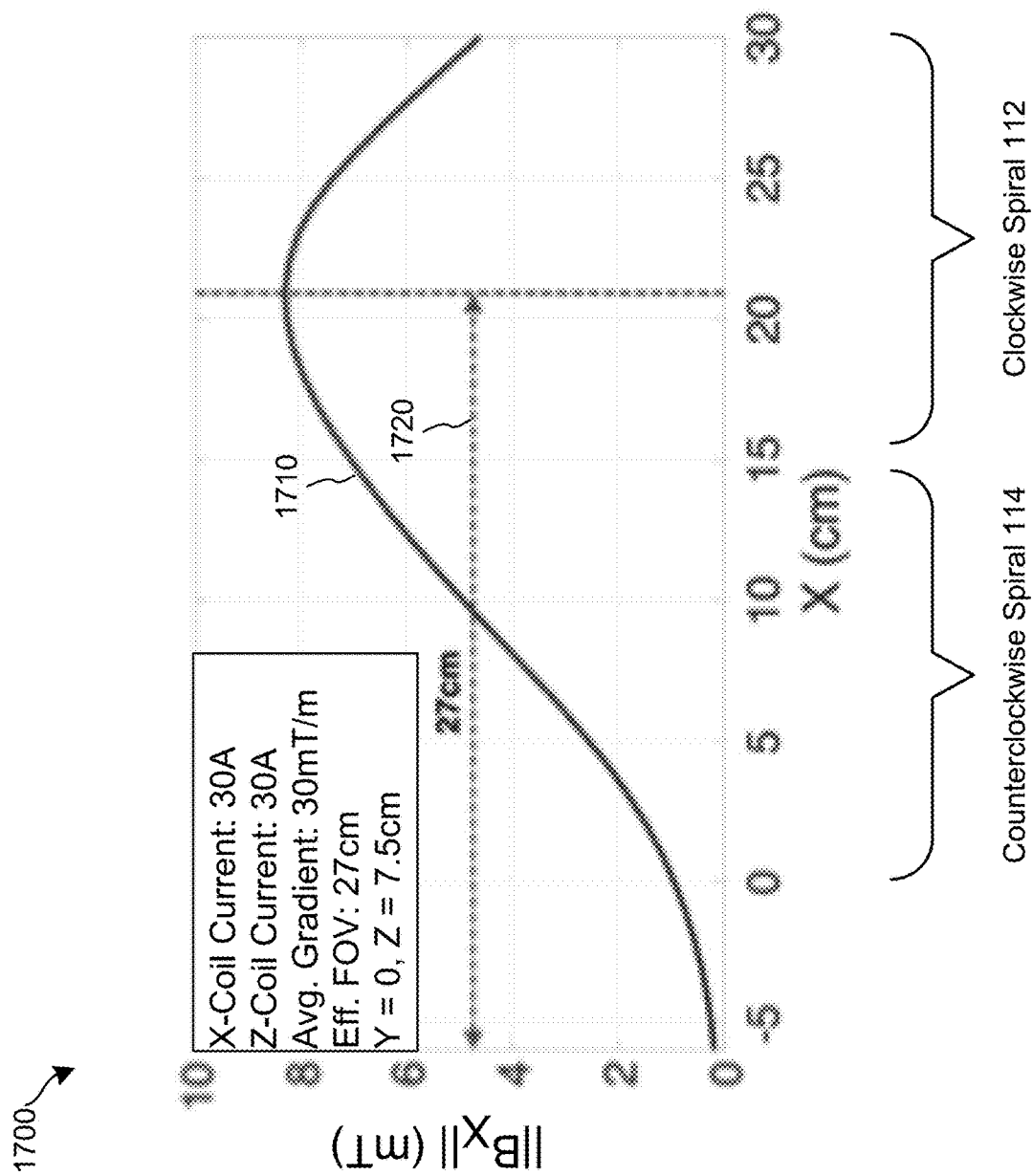
FIG. 17 is a graph that illustrates an example of the total magnetic field ($\|B_X\|$) produced simultaneously by the first and third electromagnet coil sets.

Therefore, the third electromagnet coil set 130 can be positioned below (e.g., directly below) the first electromagnet coil set 110 and both can be turned on simultaneously. The resulting magnetic field profile along the X-axis is plotted in graphs 1600 and 1700 in FIGS. 16 and 17, respectively. Graph 1600 illustrates the Z-component of the combined magnetic field 1610 produced simultaneously by the first and third electromagnet coil sets 110, 130. The combined magnetic field 1610 was measured at Y=0 cm, Z=7.5 cm, and at varying X positions. A DC current of 30 A was used in the first and third electromagnet coil sets 110, 130 to produce the combined magnetic field 1610. As can be seen, the combined magnetic field 1610 has a monotonically-varying region 1620 of 18 cm from X=3 cm to X=21 cm, which corresponds to the FOV for the combined magnetic field 1610. The average gradient of magnetic field 1610 ($B_{Xz}$) is about 54 mT/m.

Graph 1700 illustrates an example of the total magnetic field 1710 ($\|B_X\|$) produced simultaneously by the first and third electromagnet coil sets 110, 130. The total magnetic field 1710 has a large region 1720 in which the magnitude of the total magnetic field 1710 increases monotonically. The region 1720 is about 27 cm wide from X=−6 cm to X=21 cm, where a negative X value corresponds to an equivalent distance away from the outer edge of counterclockwise spiral 114. Region 1720 is the X FOV when the first and third electromagnet coil sets 110, 130 are turned on together. The 27 cm FOV (region 1720) is equal to 90% of the first electromagnet coil set 110 width (30 cm).

The average gradient of magnetic field 1710 ($\|B_X\|$) is about 30 mT/m. The combined magnetic field 1710 was measured at Y=0 cm, Z=7.5 cm, and at varying X positions. A DC current of 30 A was used in the first and third electromagnet coil sets 110, 130 to produce the total magnetic field 1710.

Graph 1800 illustrates an example of the total magnetic field 1810 ($\|B_Y\|$) produced simultaneously by the second and third electromagnet coil sets 120, 130. The total magnetic field 1810 has a large region 1820 in which the magnitude of the total magnetic field 1810 increases monotonically. The region 1820 is about 27 cm wide from Y=−6 cm to Y=21 cm, where a negative Y value corresponds to an equivalent distance away from the outer edge of counterclockwise spiral 124. Region 1820 is the Y FOV when the second and third electromagnet coil sets 120, 130 are turned on together. The 27 cm FOV (region 1720) is equal to 90% of the second electromagnet coil set 120 width (30 cm).

Figure 18:
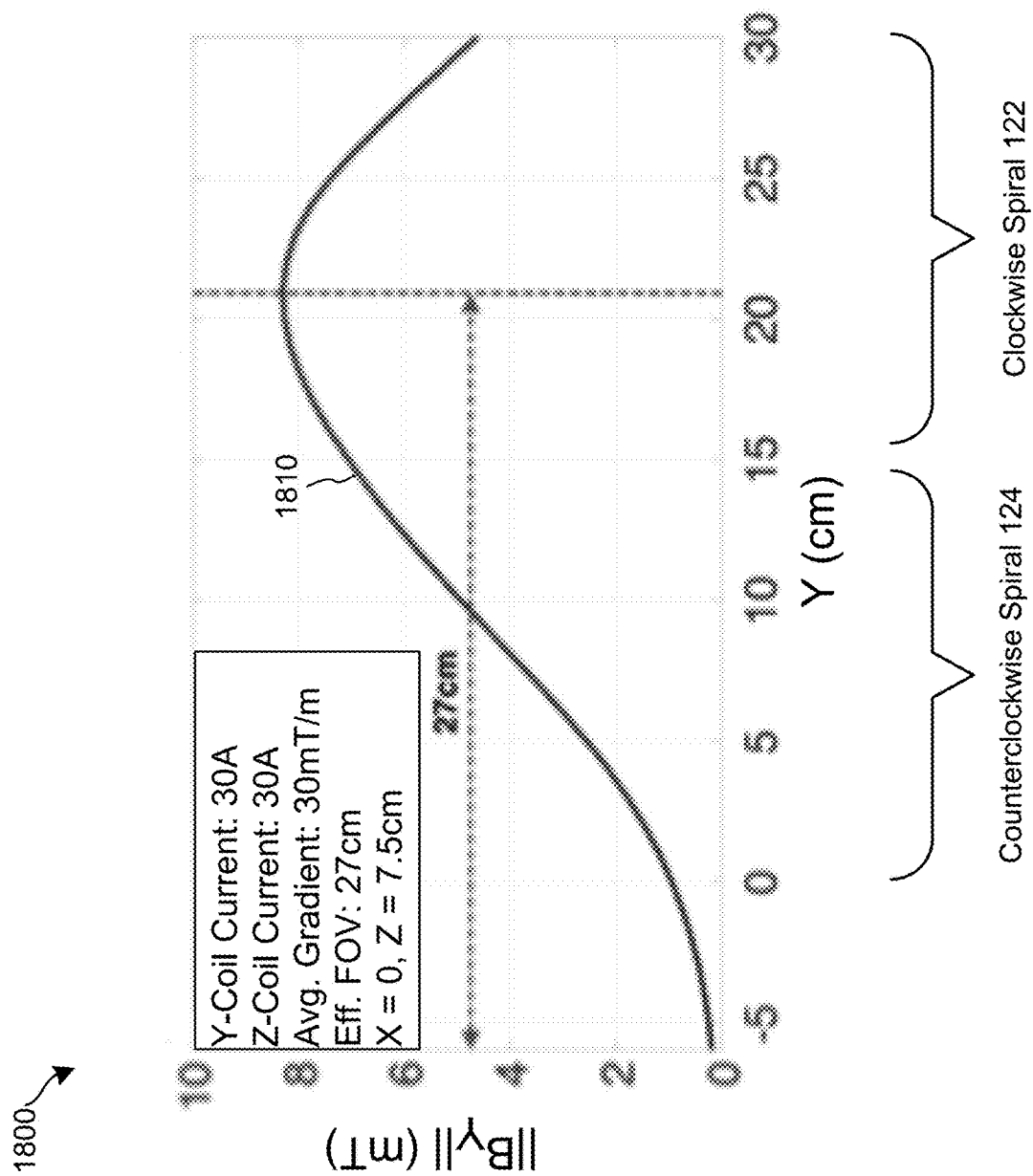
FIG. 18 is a graph that illustrates an example of the total magnetic field ($\|B_Y\|$) produced simultaneously by the second and third electromagnet coil sets.

The average gradient of magnetic field 1810 ($\|B_Y\|$) is about 30 mT/m. The combined magnetic field 1810 was measured at X=0 cm, Z=7.5 cm, and at varying Y positions. A DC current of 30 A was used in the first and third electromagnet coil sets 120, 130 to produce the total magnetic field 1810. As can be seen in FIG. 18, the total magnetic field 1710 and total magnetic field 1810 are identical or substantially identical with respect to the X and Y axes (e.g., first and second axes), respectively.

For off-center regions where Y≠0 (for total magnetic field 1710), the Y-component of the X and Z coils is also present and contributes to the total magnetic field generated 1710 by the two coils. Nonetheless, the qualitative nature of the field profile resembles graph 1700 in all the cases, as discussed below.

Figure 19:
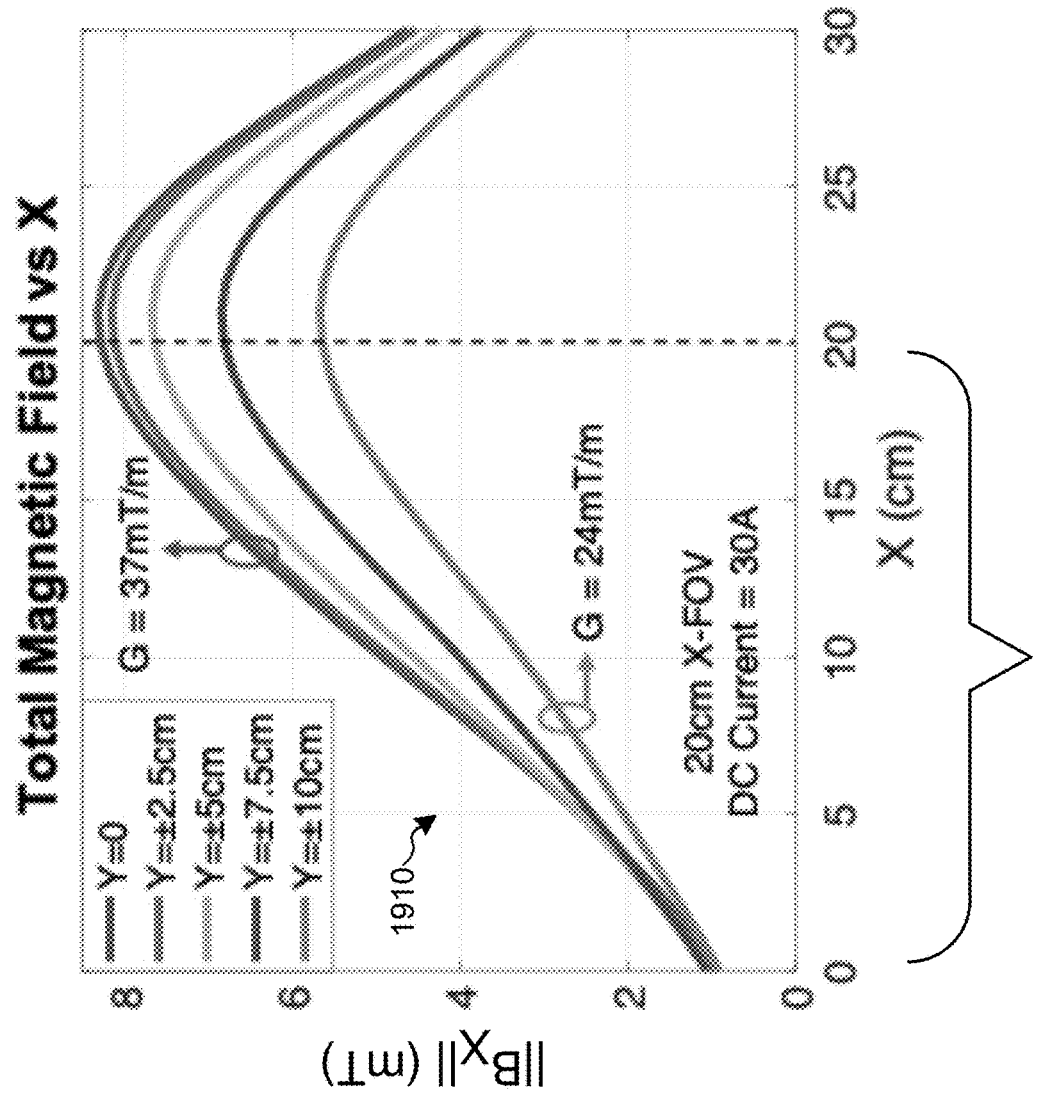
FIG. 19 is a graph that illustrates the total magnetic field ($\|B_X\|$) plotted for different Y values.

In order to evaluate the homogeneity of the total magnetic field produced simultaneously by the first and third electromagnet coil sets 110, 130, the total magnetic field 1910 ($\|B_X\|$) can be plotted for different Y values from 0 to ±10 cm at ±2.5 cm intervals, while keeping Z=7.5 cm, at various X values as shown in graph 1900 in FIG. 19. Due to the non-homogenous nature of the Z-coil's magnetic field along the X-axis as the Y-coordinate is varied, the total gradient strength reduces monotonically from 37 mT/m at Y=0 to 24 mT/m at Y=±10 cm. A DC current of 30 A was used in the first and third electromagnet coil sets 110, 130 to produce the total magnetic fields 1910. When operated simultaneously at 30A of DC power, the first and third electromagnet coil sets 110, 130 have a monotonic X FOV 1920 of about 20 cm in which the magnitude of the total magnetic field 1910 varies (increases) monotonically. This 20 cm X FOV 1920 represents a substantial portion of the total magnetic field 1910 ($\|B_X\|$) that has a monotonically-varying magnitude.

Figure 20:
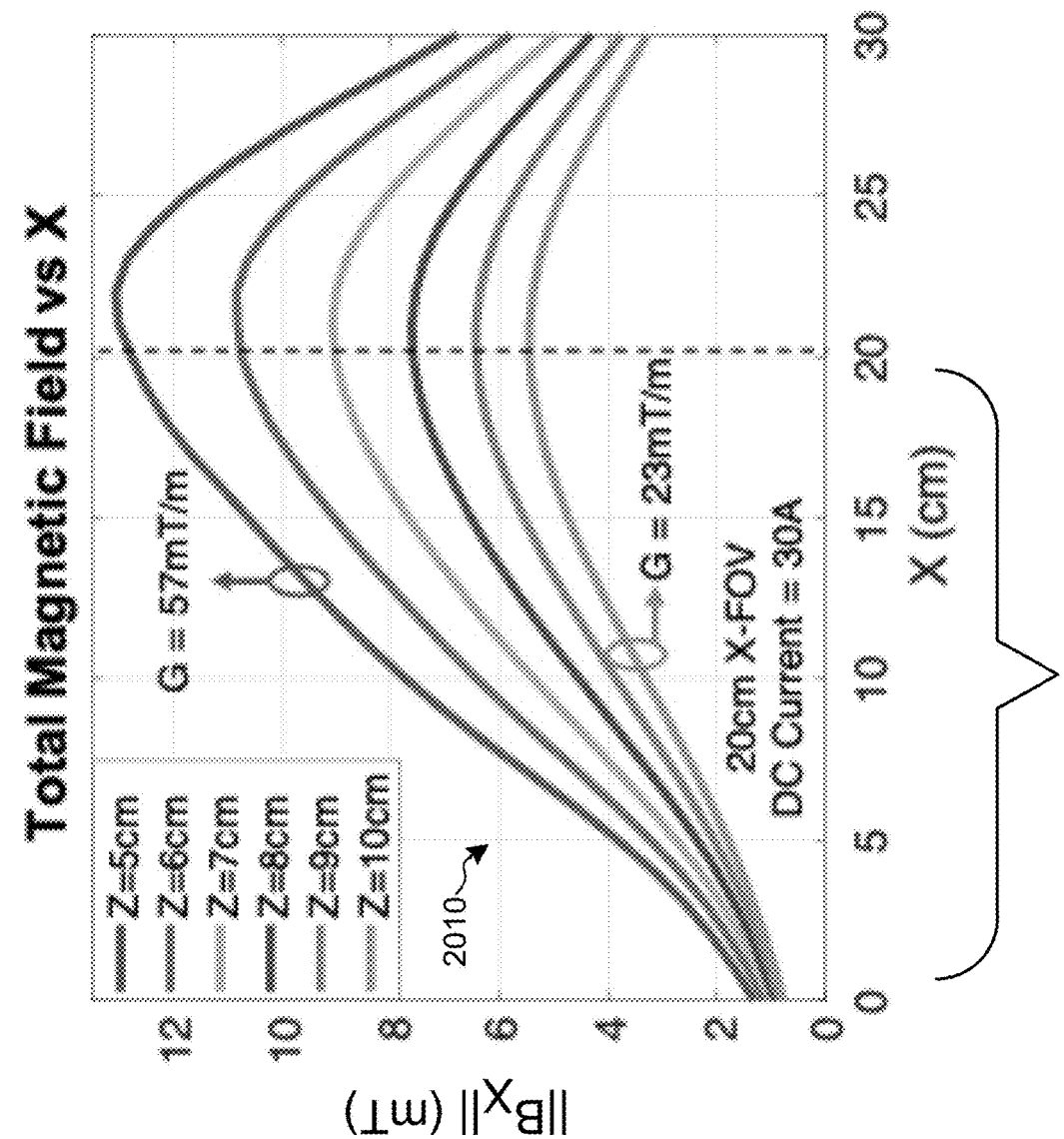
FIG. 20 is a graph that illustrates the total magnetic field ($\|B_X\|$) plotted for different Z values.

Similarly, in order to evaluate the homogeneity of the total magnetic field produced simultaneously by the first and third electromagnet coil sets 110, 130, the total magnetic field 2010 can be plotted for different Z values from ±5 cm to ±10 cm at ±1 cm intervals, while keeping Y=0 cm, at various X values as shown in graph 2000 in FIG. 20. As expected, the gradient strength decreases monotonically from 57 mT/m at Z=5 cm to 23 mT/m at Z=10 cm. A DC current of 30 A was used in the first and third electromagnet coil sets 110, 130 to produce the total magnetic fields 2010. When operated simultaneously at 30A of DC power, the first and third electromagnet coil sets 110, 130 have a monotonic X FOV 2020 of about 20 cm in which the magnitude of the total magnetic field 2010 varies (increases) monotonically.

Thus, the ratio of the 20 cm X FOV 1920, 2020 to the width 116 of the first magnetic coil set 110 (30 cm when producing the total magnetic field gradients 1910, 2010) is about 2:3, though the ratio can range from 1:2 to about 3:4 in other embodiments (e.g., less than or equal and/or greater than or equal to 2:3).

Figure 21:
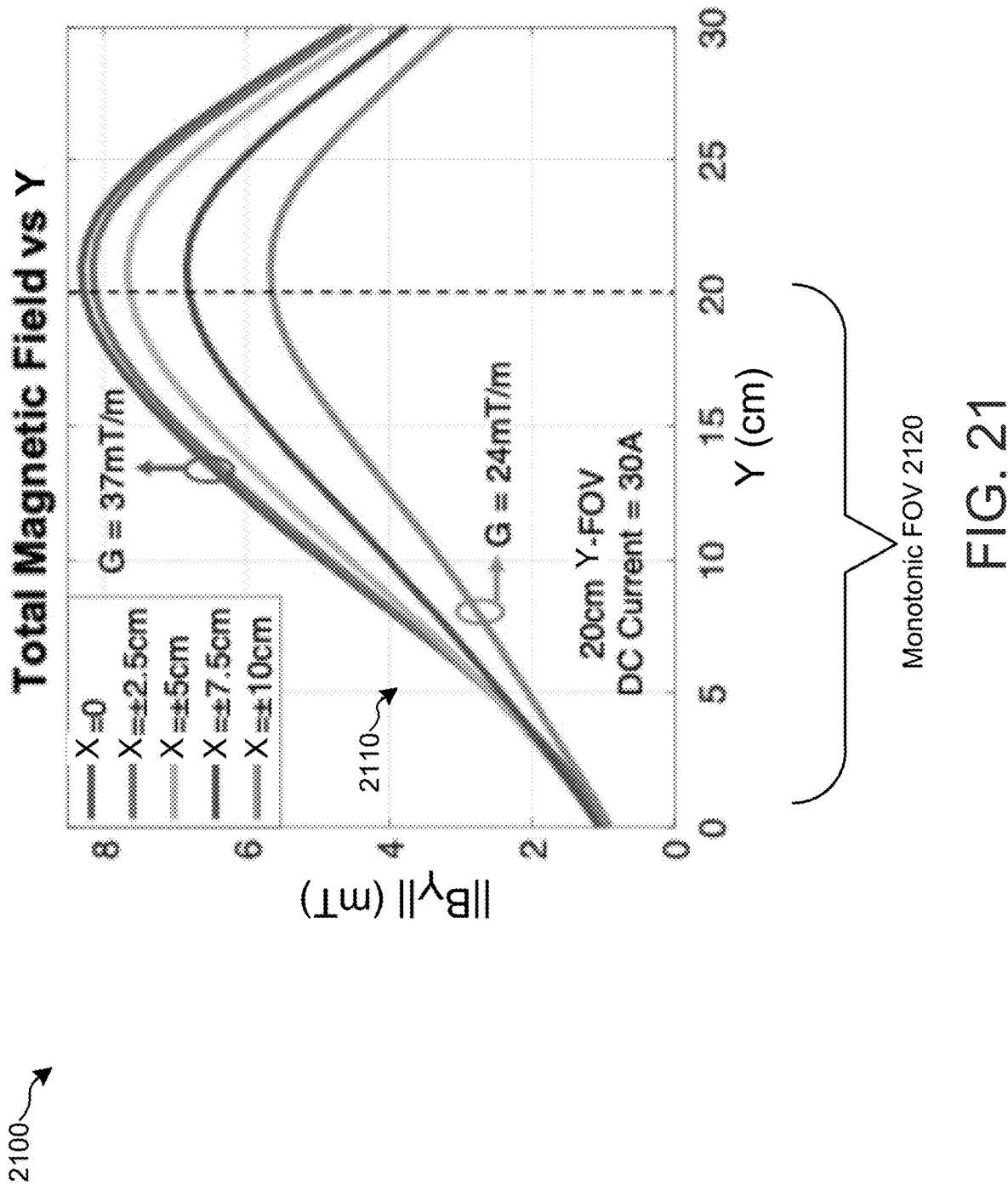
FIG. 21 is a graph that illustrates the total magnetic field ($\|B_y\|$) plotted for different x values.
Figure 22:
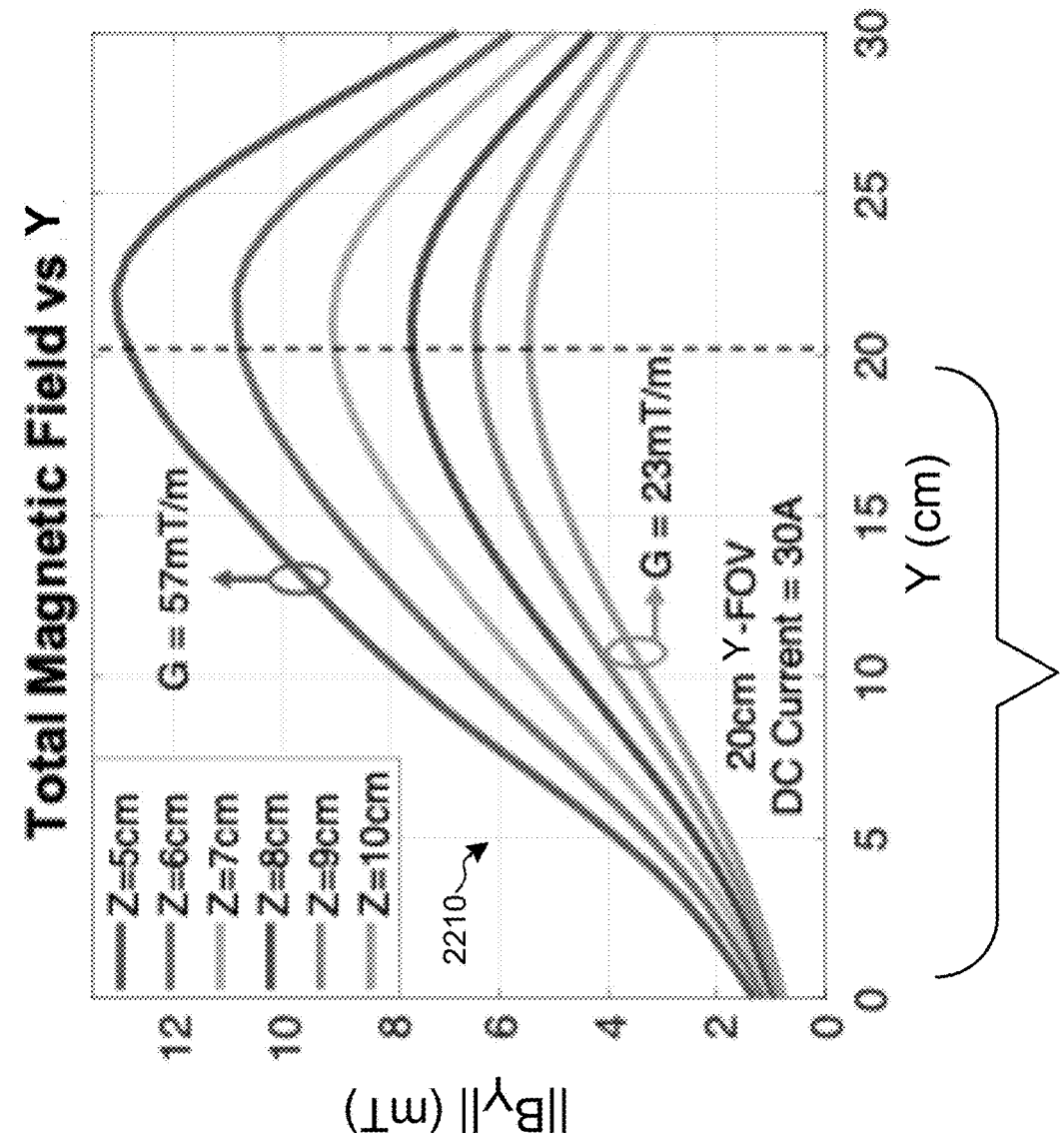
FIG. 22 is a graph that illustrates the total magnetic field ($\|B_y\|$) plotted for different Z values.

FIGS. 21 and 22 are graphs 2100, 2200 of the total magnetic field 2110, 2200 produced simultaneously by the second and third electromagnet coil sets 120, 130. In graph 2100, the total magnetic field 2110 is plotted for different X values from 0 to ±10 cm at ±2.5 cm intervals, while keeping Z=7.5 cm, at various Y values. Due to the non-homogenous nature of the Z-coil's magnetic field along the Y-axis as the X-coordinate is varied, the total gradient strength reduces monotonically from 37 mT/m at X=0 to 24 mT/m at X=±10 cm, similar to graph 1900. A DC current of 30 A was used in the second and third electromagnet coil sets 120, 130 to produce the total magnetic fields 2110. When operated simultaneously at 30A of DC power, the second and third electromagnet coil sets 120, 130 have a monotonic Y FOV 2120 of about 20 cm in which the magnitude of the total magnetic field 2110 varies (increases) monotonically.

Similarly, in order to evaluate the homogeneity of the total magnetic field produced simultaneously by the second and third electromagnet coil sets 120, 130, the total magnetic field 2210 is plotted for different Z values from ±5 cm to ±10 cm at ±1 cm intervals, while keeping X=0 cm, at various Y values as shown in graph 2200. As expected, the gradient strength decreases monotonically from 57 mT/m at Z=5 cm to 23 mT/m at Z=10 cm. A DC current of 30 A was used in the second and third electromagnet coil sets 120, 130 to produce the total magnetic fields 2210. When operated simultaneously at 30A of DC power, the second and third electromagnet coil sets 120, 130 have a monotonic Y FOV 2220 of about 20 cm in which the magnitude of the total magnetic field 2210 varies (increases) monotonically.

Thus, the ratio of the 20 cm Y FOV 2120, 2220 to the length 126 of the second magnetic coil set 110 (30 cm when producing the total magnetic field gradients 2110, 2210) is about 2:3, though the ratio can range from 1:2 to about 3:4 in other embodiments (e.g., less than or equal and/or greater than or equal to 2:3).

This implies that for a given sensor resolution, the obtained position resolution would be higher as the magnetic sensor device moves closer to the center of an FOV spanning 20 cm×20 cm×10 cm in the X, Y and Z directions respectively. In order to improve the position resolution obtained at the boundary planes of the FOV, either the DC current in coils should be increased (resulting in higher gradient), or the sensor resolution should be higher. Keeping the maximum current as 30 A, we employ the sensor in low-noise mode towards the boundary planes where the gradient strength is <30 mT/m. In the low-noise mode, the sensor has a resolution of 1 µT, requiring only 10 mT/m to achieve 100 µm of position error. However, the current consumption in low-noise mode is 2.2 mA for 850 µs, compared to 1.5 mA for 250 µs in the low-power mode (which has a resolution of 3 µT). With the extra power penalty on the sensor side, the desired position resolution can be achieved in the entire FOV. In some embodiments, the power management unit in the magnetic sensor device (e.g., in the controller chip) can be designed with high efficiency to wirelessly send comparatively higher power to the magnetic sensor device when it is operated in low-noise mode.

Each point inside the FOV corresponds to a unique set of magnetic field values obtained from the three orthogonal gradients. For applications requiring bigger FOV, the physical dimensions can be correspondingly scaled for all the coils. The DC current is another parameter for scaling the FOV vertically. With a DC current value of 30 A in both the X and Z coils, the average value of η for the X-gradient is 588 µT/m/A.

Figure 23:
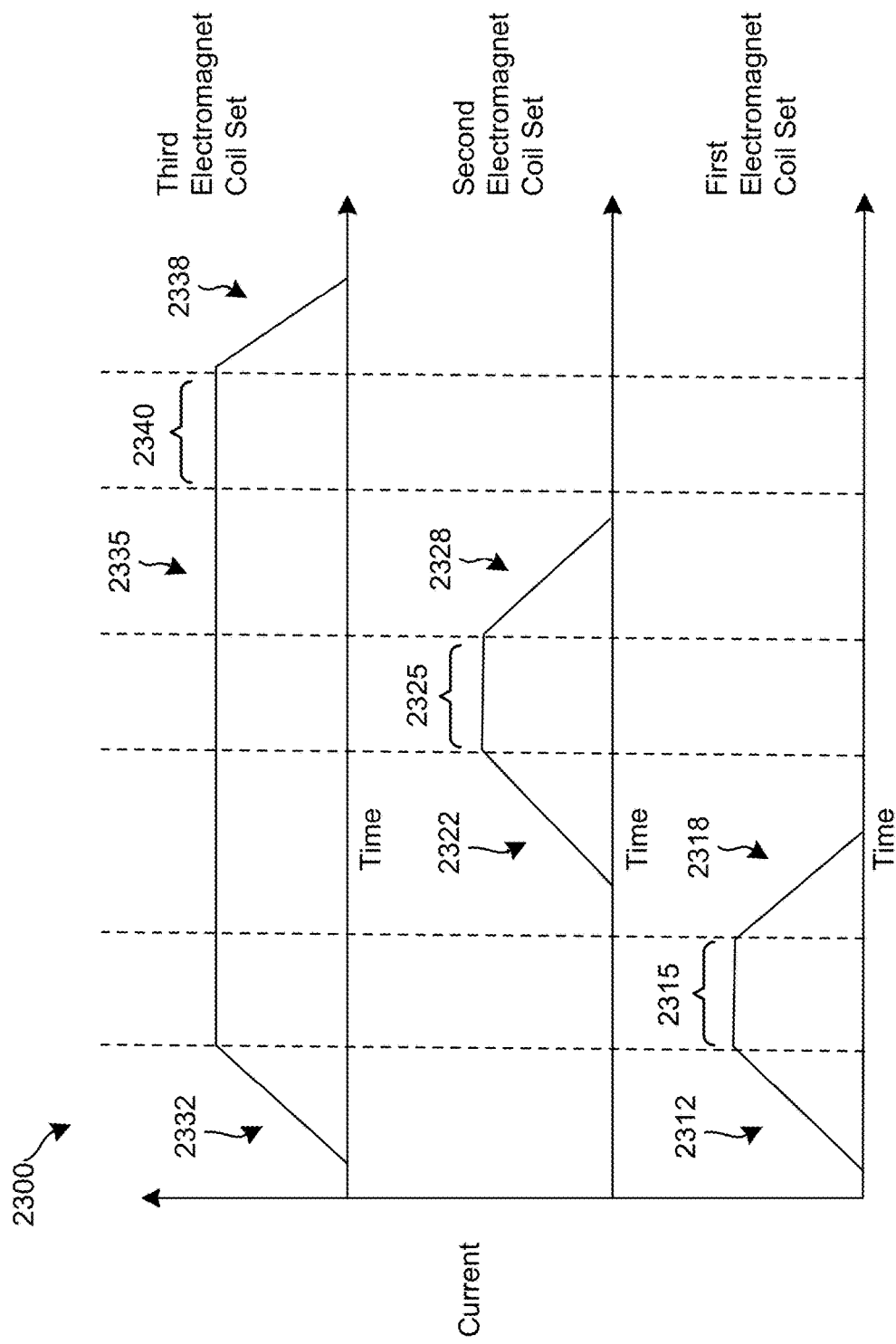
FIG. 23 is a timing diagram of electrical current through the first, second, and third electromagnet coil sets, respectively, according to an embodiment.

FIG. 23 is a timing diagram 2300 of electrical current through the first, second, and third electromagnet coil sets 110, 120, 130, respectively, according to an embodiment. Current plot 2310 illustrates electrical current through the first electromagnet coil set 110 versus time. Current plot 2320 illustrates electrical current through the second electromagnet coil 120 set versus time. Current plot 2330 illustrates electrical current through the third electromagnet coil set 130 versus time. The electrical current is selectively controlled by controller 100.

As can be seen, in current plot 2310, 2320, 2330 there is a respective ramp-up time period 2312, 2322, 2332, a respective steady-state "on" period 2315, 2325, 2335, and a respective ramp-down period 2318, 2328, 2338. The timing diagram 2300 illustrates that the first and third electromagnet coil sets 110, 130 are turned on simultaneously in ramp-up time periods 2312, 2332. In steady-state on period 2315, steady-state current flows through the first and third electromagnet coil sets 110, 130 to simultaneously produce the first and third magnetic fields. A first total magnetic field (e.g., a first localization magnetic field) produced by the first and third electromagnet coil sets 110, 130 has a monotonically-varying magnitude within the FOV in the first axis (e.g., the X axis). Steady-state on period 2315 is the measurement time period (e.g., for a magnetic sensor device) for the first total magnetic field. The first total magnetic field can be the same as total magnetic fields 1710, 1910, and/or 2010.

After steady-state on period 2315, the controller 100 simultaneously ramps down 2318 current to the first electromagnet coil set 110 to turn off the first electromagnet coil set 110 and ramps up 2322 current to the second electromagnet coil set 120 to turn on the second electromagnet coil set 120. Alternatively, the controller 100 can ramp down 2318 current to the first electromagnet coil set 110 and then ramp up 2322 current to the second electromagnet coil set 120. The controller 100 continues to flow current through the third electromagnet coil set 130 during ramp-up period 2322. In steady-state on period 2325, steady-state current flows through the second and third electromagnet coil sets 120, 130 to simultaneously produce the second and third magnetic fields. A second total magnetic field (e.g., a second localization magnetic field) produced by the second and third electromagnet coil sets 120, 130 has a monotonically-varying magnitude within the FOV in the second axis (e.g., the Y axis). Steady-state on period 2325 is the measurement time period (e.g., for a magnetic sensor device) for the second total magnetic field. The second total magnetic field can be the same as total magnetic fields 1810, 2110, and/or 2210. Time period 2325 can be 50 ms to 250 ms, including about 100 ms, about 150 ms, about 200 ms, and any time period or range of time period between any two of the foregoing time periods.

After steady-state on period 2315, the controller 100 ramps down 2328 current to the second electromagnet coil set 120 to turn off the second electromagnet coil set 120 while maintaining power to the third electromagnet coil set 130. After the second electromagnet coil set 120 is off, steady-state current flows only through the third electromagnet coil set 130 during time period 2340 to produce only the third magnetic field (e.g., a third localization magnetic field), which has a monotonically-varying magnitude within the FOV in the third axis (e.g., the Z axis). Time period 2340 is the measurement time period (e.g., for a magnetic sensor device) for the third magnetic field. The third magnetic field can be the same as monotonically-varying magnetic total fields 1510. Time period 2340 can be 50 ms to 250 ms, including about 100 ms, about 150 ms, about 200 ms, and any time period or range of time period between any two of the foregoing time periods.

Steady-state measurement time periods 2315, 2325, and 2340 can be about 10 ms to about 25 ms, including about 15 ms, about 20 ms, and any time period or range of time period between any two of the foregoing time periods. Ramp-up time periods 2312, 2322, 2332, and ramp-down time periods 2318, 2328, 2338 can be about 50 ms to about 150 ms, including about 75 ms, about 100 ms, about 125 ms, and any time period or range of time period between any two of the foregoing time periods. The length of the ramp-up time periods 2312, 2322, 2332 and ramp-down time periods 2318, 2328, 2338 can be affected by the DC current supplies in controller 100.

For a given magnetic field resolution that the magnetic sensor device can measure ($\Delta B$), the gradient strength (G) of the magnetic field gradient is determined by the required localization resolution ($\Delta X$), as given by the relation $\Delta X = \Delta B/G$. In one embodiment, $\Delta B$ is 15 µT and in order to get 500 µm resolution for $\Delta X$, the required G is 30 mT/m. When 25 or more samples of the magnetic field are measured and averaged, the measurement error of the ingestible magnetic sensor can lower from AB of 15 µT to 3 µT, which can improve the spatial resolution from 500 µm to 100 µm for a given magnetic field gradient strength of 30 mT/m.

Figure 24:
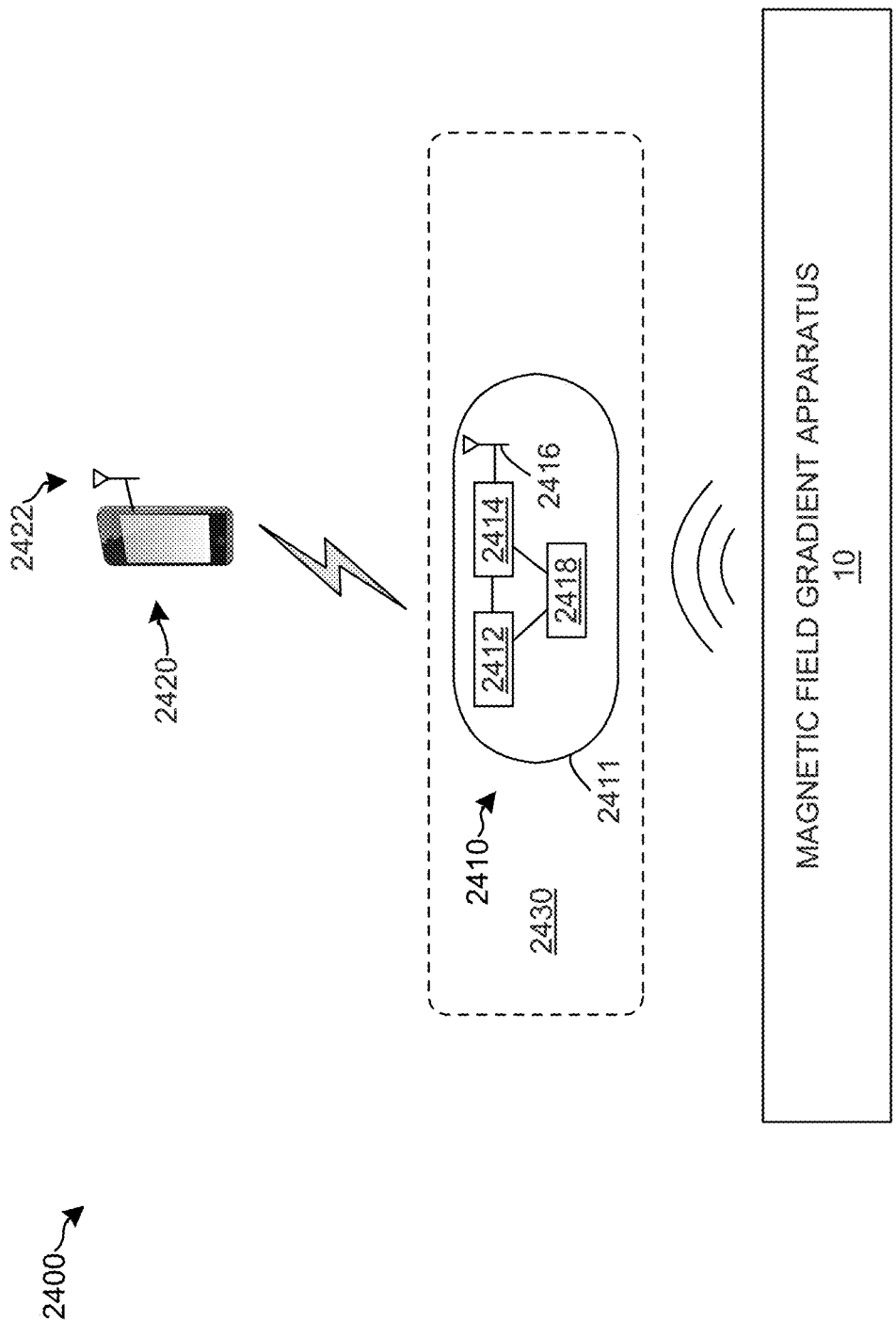
FIG. 24 is a block diagram of a system for locating a relative position of a magnetic sensor device according to an embodiment.

FIG. 24 is a block diagram of a system 2400 for locating a relative position of a magnetic sensor device according to an embodiment. The system 2400 includes the magnetic field gradient apparatus 10 (e.g., as described herein), a magnetic sensor device 2410, and a receiver 2420.

The magnetic sensor device 2410 includes a capsule or housing 2411 and a circuit that includes a three-dimensional magnetic sensor 2412, a device controller 2414, an antenna 2416, and a power source 2418. The capsule or housing 2411 can be an ingestible capsule that can comprise polydimethylsiloxane (PDMS) or another biosafe material. Alternatively, the capsule or housing 2411 can include a biocompatible housing so that the magnetic sensor device 2310 can be placed on or near an anatomical feature 2430 of a subject such as a mammal (e.g., a human). In another embodiment, the capsule or housing 2411 does not include a biocompatible housing or an ingestible capsule. In any case, the capsule or housing 2411 preferably does not attenuate or affect external magnetic fields, such as those produced by apparatus 10.

The three-dimensional magnetic sensor 2412 measures the magnetic field at the position of the ingestible magnetic sensor 2412 and outputs the magnetic field measurements to the device controller 2414. The magnetic field measurements include a measurement of each of the X, Y, and Z field values, which can each be provided as a 16-bit data vector. The three-dimensional magnetic sensor 2412 can measure the magnetic field based on control signals received from the device controller 1414, which can be sent over a protocol such as 12C. In some embodiments, 25 or more measurements of each magnetic field gradient can be taken. The control signals can include a timing sequence for the three-dimensional magnetic sensor 2412 to perform the magnetic field measurements. The timing sequence can correspond to the predetermined time sequence of the localization magnetic field gradients. In addition, the control signals can include configuration settings for power, noise, and/or frequency of measurement (e.g., 1 to 5 magnetic field measurements per minute) of the three-dimensional magnetic sensor 2412. In an example embodiment, the three-dimensional magnetic sensor 2412 can comprise an AK09970N Tri-axis Magnetic Sensor IC with Digital Output available from Asahi Kasei Microdevices Corporation, though other three-dimensional magnetic sensors can be used. It is understood that certain examples provided herein are only provided for the purpose of illustration and explanation, and the examples are not limiting of the invention. Those skilled in the art will appreciate substitution of equivalent, similar or other examples without departing from the scope of the disclosure or invention.

The device controller 2414 includes a microprocessor, local memory (e.g., cache and RAM), and a transceiver that can support one or more wireless protocols such as Bluetooth (e.g., Bluetooth low-energy (LE)), near-field communication (NFC), and/or another wireless protocol. The device controller 2414 can store the magnetic field measurements in its local memory (e.g., cache or RAM) and then encode the magnetic field measurements in one or more magnetic sensor output signals. The magnetic sensor output signal(s) is/are broadcast by the antenna 2416 using a wireless protocol (e.g., Bluetooth LE) and sent to the receiver 2420 (e.g., which receives the output signal(s) using receiver antenna 2422). An antenna-matching circuit can be included between the device controller 2414 and the antenna 2416 to improve and/or maximize power transmission to the antenna 2416 for radiation. In an example embodiment, the device controller 2414 can comprise an NRF52832 Bluetooth 5.2 System-on-a-Chip (SoC) available from Nordic Semiconductor, though other microprocessors or SoCs can be used. In addition, the antenna 2416 can comprise a 2450AT18B100 2.4 GHz Mini Antenna available from Johanson Technology, Inc.

The power source 2418 provides power for the three-dimensional magnetic sensor 2412 and the device controller 2414. The power source 2418 can include a battery such as one or more coin-cell rechargeable batteries (e.g., 3V, 11 mAh) such as the MS920SE available from Seiko Instruments, Inc. In another embodiment, the power source 2418 can comprise an inductor that can wirelessly receive energy via inductive coupling. In another embodiment, the power source 2418 can derive power biochemically. The power source 2418 can receive and/or derive power from other external sources and/or from internal sources.

The receiver 2420 includes a microprocessor and an antenna that can receive the magnetic sensor output signals from the magnetic sensor device 2410 using a wireless protocol (e.g., Bluetooth LE). For example, the receiver 2420 can comprise a smartphone, a laptop computer, a desktop computer, a tablet, or another computer. The receiver 2420 can then determine the three-dimensional spatial coordinates, relative to the apparatus 10, of the magnetic sensor device 2410 using the magnetic field measurements encoded in the magnetic sensor output signals. The relative three-dimensional spatial coordinates of the magnetic sensor device 2410 can optionally be displayed on an internal display on the receiver 2420 and/or on an external display coupled to the receiver 2420. The relative three-dimensional spatial coordinates can be determined using a look-up table, a mathematical model, or other relationship stored in the receiver 2420. For example, the look-up table can be created by making a series of measurements of the localization magnetic field gradients produced by the apparatus 10 at a series of known spatial coordinates proximal to the apparatus 10, such as every 100 µm, every 500 µm, or other distance in each dimension. The Earth's ambient magnetic field can be subtracted from the measured magnetic field measurements in the look-up table.

In addition, the receiver 2420 can send control signals and/or commands to the device controller 2414. The control signals and/or commands (in general, control signals) from the receiver 2420 can trigger magnetic field measurements, such as by causing the device controller 2414 to send control signals to the three-dimensional magnetic sensor 2412. The control signals from the receiver 2420 can also include a timing sequence for the three-dimensional magnetic sensor 2412 to perform the magnetic field measurements. Alternatively, the timing sequence can be created by having the receiver 2420 send control signals that trigger magnetic field measurements according to a predetermined timing sequence. The control signals from the receiver 2420 can also cause the device controller 2414 to send the magnetic sensor output signals to the receiver 2420. In addition, the receiver 2420 can send control signals to configure the device controller 2414 and/or the three-dimensional magnetic sensor 2412. For example, the receiver 2420 can configure the wireless communication settings (e.g., wireless protocol, encryption, etc.) of the device controller 2414. In addition, the receiver 2420 can configure the power, noise, and/or frequency of measurement (e.g., 1 to 5 magnetic field measurements per minute) settings of the three-dimensional magnetic sensor 2412.

In operation, the magnetic sensor device 2410 can be ingested into or placed in an internal volume 1440 of a mammal (e.g., a human patient). For example, the magnetic sensor 2410 can be ingested into the gastrointestinal (GI) tract of a mammal (e.g., a human patient or other mammal). The apparatus 10 is then placed such that its FOV is within the mammal's GI tract. For example, the apparatus 10 can be placed on or in a platform or bed (on which the mammal lies down), the back of a chair (in which the mammal sits). Alternatively, the apparatus 10 can be disposed in a wearable device, for example that can be wrapped around the subject's (e.g., mammal's) stomach. The receiver 2420 communicates wirelessly with the device controller 2414 in the magnetic sensor device 2410 to trigger a magnetic field measurement and/or to receive the raw field data. A user interface on the receiver 2420 can display the three-dimensional position of the ingestible magnetic sensor 2410 with respect to the position of the apparatus 10 (e.g., of the electromagnet coils 110, 120, 130).

The receiver 2420 can receive and/or display the relative position of the magnetic sensor device 2410 in real time (or substantially real time due to transmission times, etc.) or in non-real time (e.g., at a later time). For example, the magnetic sensor device 2410 can temporarily store multiple magnetic field measurements and send them as a group to the receiver 2420. Additionally or alternatively, the receiver 2420 can receive the magnetic field measurements from the magnetic sensor device 2410 for display at a later time on the display of the receiver 2420 or on another device, such as a computer.

Since the DC current for the localization magnetic field gradient can be quite high (e.g., up to 50 A), heating of the electromagnet coils 110, 120, 130 can be problematic if they are kept ON for a long time. To circumvent that, the electromagnet coils 110, 120, 130 can be switched in a highly time-multiplexed fashion such that they are ON only when a measurement needs to be made and OFF at all other times. For instance, performing one measurement every 5 minutes can produce about 13 W of heat on average. A thermally-insulating material (e.g., a thermally-insulating sheet) can be placed between the electromagnet coil 110, 120, 130 surface and patient's back to avoid any undesirable heating effect.

Two example embodiments of the apparatus 10 have are listed in Table 1. One embodiment is designed for orthopedic surgery and the other embodiment is designed for GI tract monitoring, those the embodiments can be used for other applications. As can be seen from Table 1, the number of turns for each electromagnet coil 110, 120, 130 are different, depending on the application of use and the desired FOV. The DC current required in the electromagnets is also based on the application and the desired magnetic field gradient in the FOV. For the DC currents given in Table 1, a magnetic field gradient of 30 mT/m can be achieved. This gradient is much stronger towards the surface and center of the electromagnet coils 110, 120, 130 and reduces to 30 mT/m at the boundaries of FOV. The strength of the gradient determines the spatial localization resolution available using system 2400.

TABLE 1

| Specification | Orthopedic Surgery Application | GI Tract Monitoring Application |
| --- | --- | --- |
| Z Coil (third electromagnet coil 130) | Inner Diameter (ID): 10 cm Outer Diameter (OD): 30 cm, 36 turns per layer (e.g., 36 turns per upper spiral winding and 36 turns per lower spiral winding) | ID: 25 cm, OD: 60 cm, 83 turns per layer (e.g., 83 turns per upper spiral winding and 83 turns per lower spiral winding) |
| X and Y Coils (first and second electromagnet coils 110, 120) | 30 cm × 30 cm, 28 turns per layer half (e.g., 28 turns per clockwise spiral and 28 turns per counterclockwise spiral) | 60 cm × 60 cm, 68 turns per layer half (e.g., 68 turns per clockwise spiral and 68 turns per counterclockwise spiral) |
| Dimension (Stacked Coils) | 30 cm × 30 cm | 60 cm × 60 cm |
| Thickness (Stacked Coils) | 2 cm | 2 cm |
| DC current in coils | 10A-30A | 10A-30A |
| Field of View (FOV) (X × Y × Z dimensions) | 20 cm × 20 cm × 10 cm | 40 cm × 40 cm × 20 cm |
| Wire type | Litz 50/32 AWG | Litz 50/32 AWG |
| Magnetic Field Gradient | 10 mT/m-30 mT/m | 5 mT/m-30 mT/m |

Figure 25:
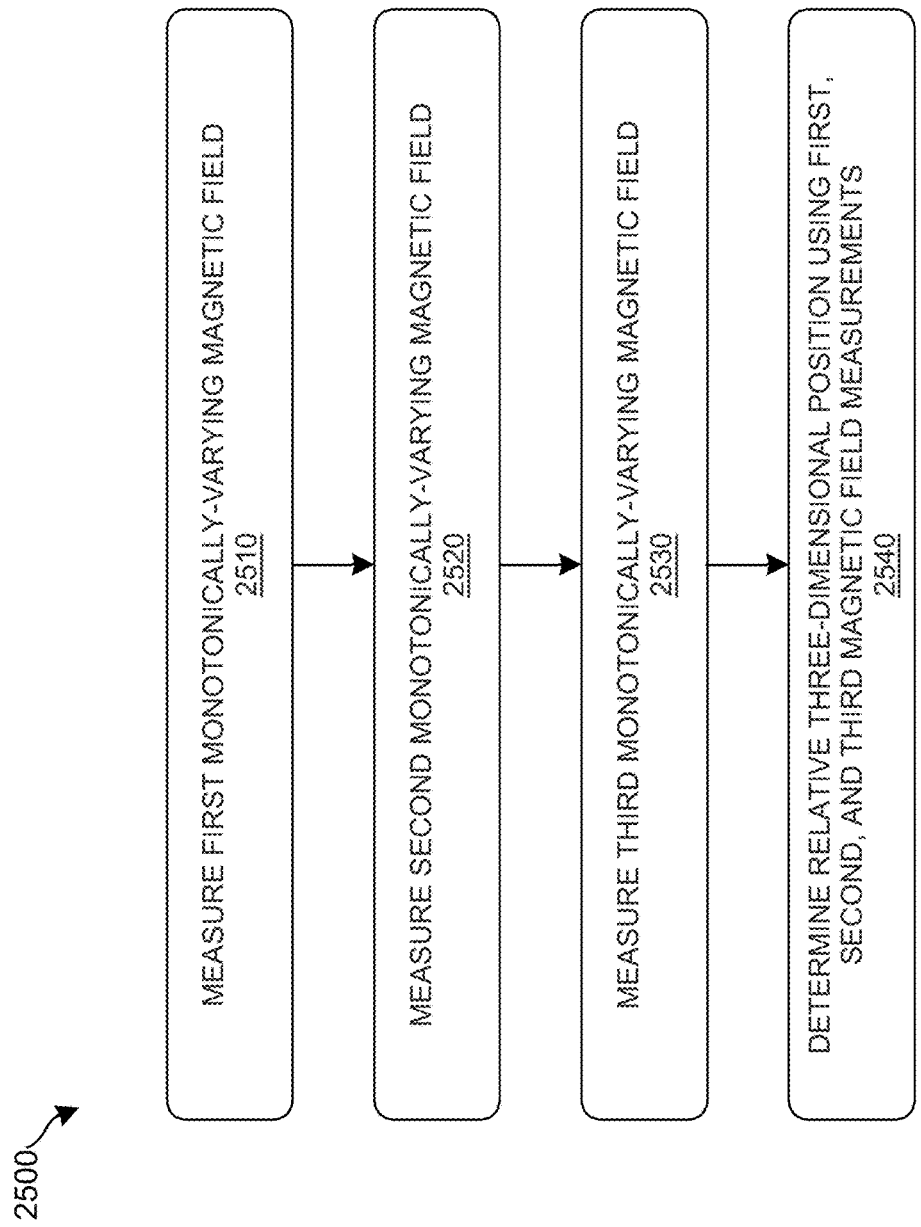
FIG. 25 is a flow chart of a method for determining the relative three-dimensional position of a magnetic sensor device according to an embodiment.

FIG. 25 is a flow chart of a method 2500 for determining the relative three-dimensional position of a magnetic sensor device according to an embodiment. The method 2500 can be performed using system 2400. In step 2510, the magnetic sensor device 2410 measures a first magnetic field with respect to a first axis (e.g., the X axis) that has a monotonically-varying magnitude within the FOV of apparatus 10. The first magnetic field corresponds to the first magnetic field gradient produced simultaneously by the first and third electromagnet coil sets 110, 130.

In step 2520, the magnetic sensor device 2410 measures a second magnetic field with respect to a second axis (e.g., the Y axis) that has a monotonically-varying magnitude within the FOV of apparatus 10. The second magnetic field corresponds to the first second field gradient produced simultaneously by the second and third electromagnet coil sets 120, 130.

In step 2530, the magnetic sensor device 2410 measures a third magnetic field with respect to a third axis (e.g., the Z axis) that has a monotonically-varying magnitude within the FOV of apparatus 10. The third magnetic field corresponds to the third second field gradient produced only by the third electromagnet coil set 130. Steps 2510, 2520, and 2530 occur sequentially but not necessarily in the order illustrated in method 2500.

In step 2540, the receiver 2420 can receive the first, second, and third magnetic field measurements and determine the relative three-dimensional position of the magnetic sensor device 2410 using the first, second, and third magnetic field measurements. The receiver 2420 can determine the relative three-dimensional position of the magnetic sensor device 2410 using a look-up table, a mathematical model, or other relationship stored. The receiver 2420 can output, display, and/or store the relative three-dimensional position of the magnetic sensor device 2410 determined in step 2540.

In an alternative embodiment, the magnetic sensor device 2410 can determine its relative three-dimensional position using the first, second, and third magnetic field measurements in the same manner as the receiver 2420.

Figure 26:
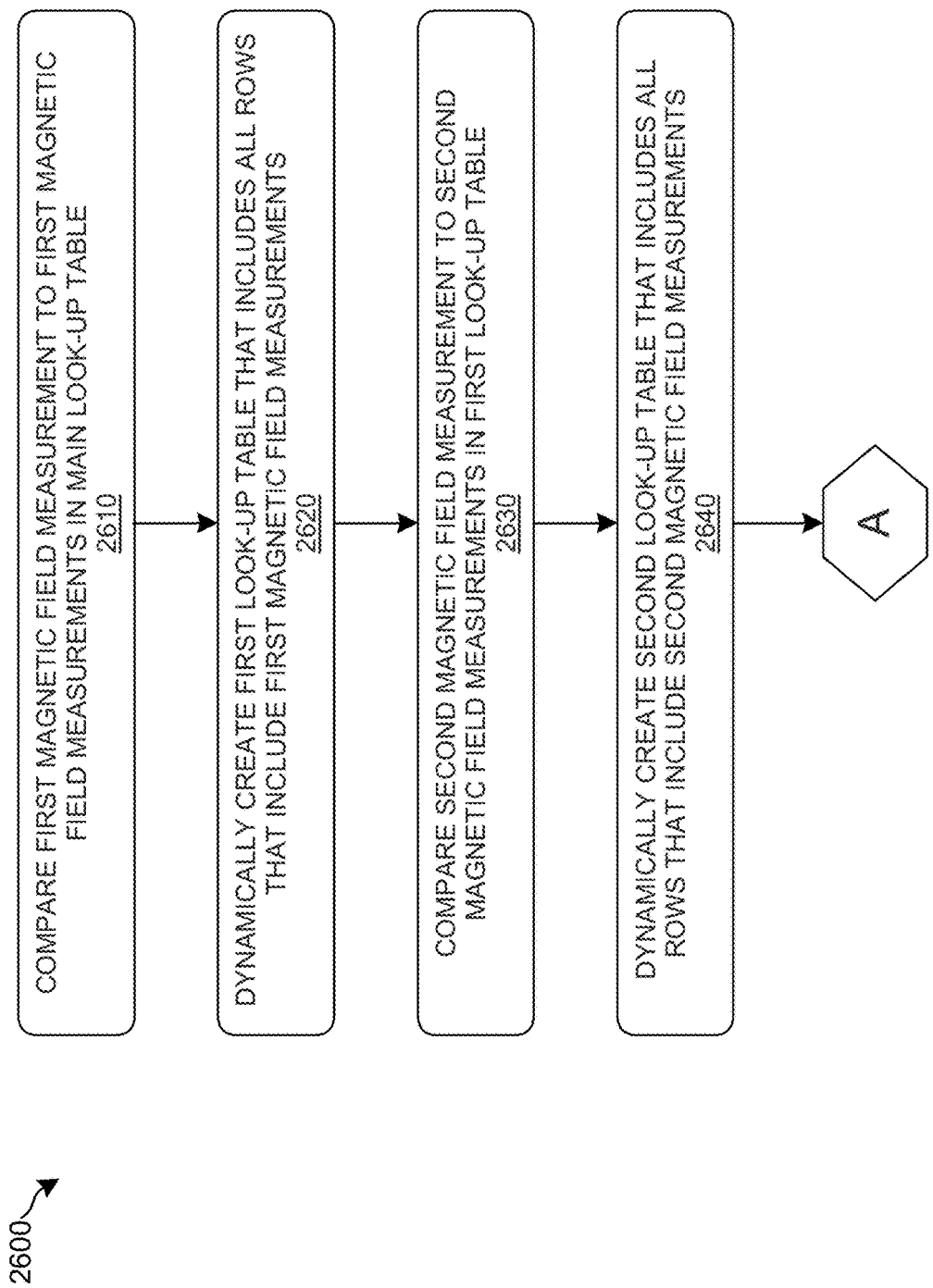
FIG. 26 is a flow chart of a method for determining the relative three-dimensional position of the magnetic sensor device according to an embodiment.
Figure 26:
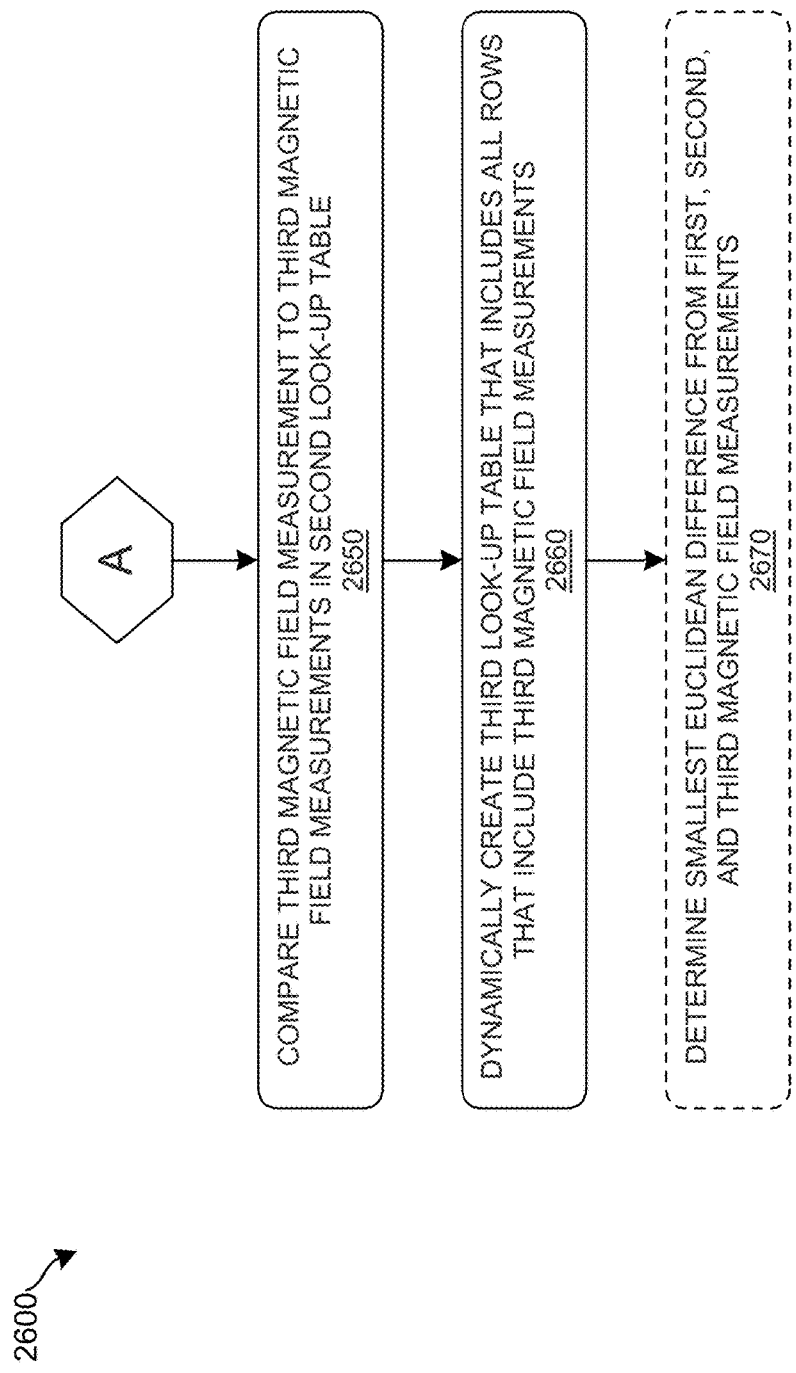

FIG. 26 is a flow chart of a method 2600 for determining the relative three-dimensional position of the magnetic sensor device 2410 according to an embodiment. Step 2540 be performed according to method 2600 in an embodiment.

In step 2610, the receiver 2420 compares the first magnetic field measurement $B_{xi}$ from the magnetic sensor device 2410 to the first magnetic field measurement values stored in a main look-up table. The main look-up table can be created by making a series of measurements of the magnetic field gradients produced by the apparatus 10 at a series of known spatial coordinates proximal to the apparatus 10, such as every 100 µm, every 500 µm, or other distance in each dimension. The Earth's ambient magnetic field can be subtracted from the measured magnetic field measurements in the main look-up table. An error ±ΔB can be included in the first magnetic field measurement $B_{xi}$, in which case the receiver 2420 compares the first magnetic field measurement range $B_{xi}$±ΔB to the first magnetic field measurement values stored in the main look-up table. The error ΔB can be about 50 µT to about 150 µT including about 75 µT, about 100 µT, about 125 µT, and any value or range between any two of the foregoing values. An example of this step is illustrated in main look-up table 2710 in FIG. 27.

Figure 27:
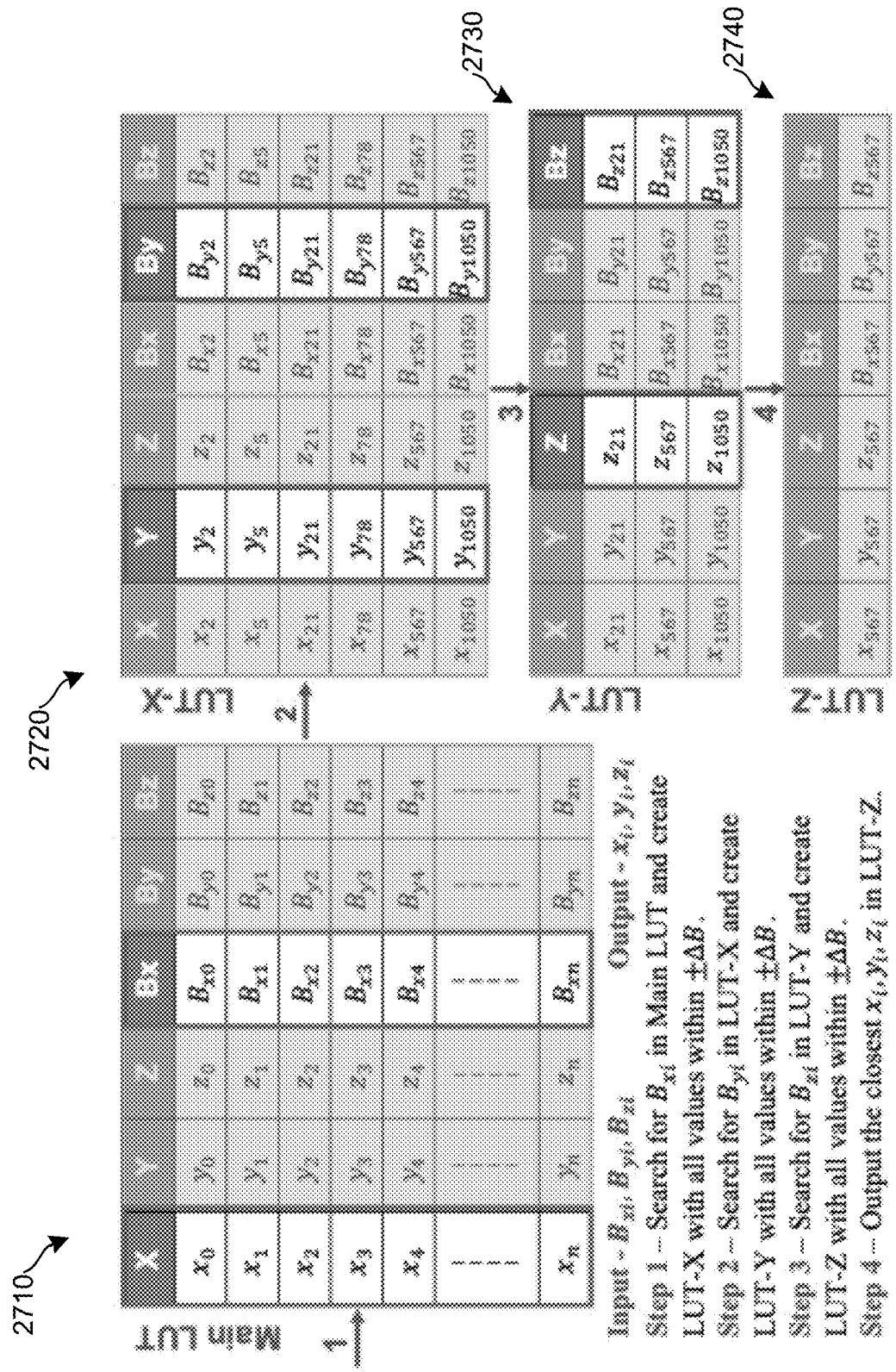
FIG. 27 illustrates an example of look-up tables that can be used to determine the relative three-dimensional position of the magnetic sensor device according to an embodiment.

In step 2620, the receiver 2420 dynamically creates a first look-up table that includes all rows from the main look-up table that include the first magnetic field measurement $B_{xi}$ or the first magnetic field measurement range $B_{xi}$±ΔB. The first look-up table is thus a subset of the main look-up table. An example of the first look-up table 2720 is illustrated in FIG. 27.

In step 2630, the receiver 2420 compares the second magnetic field measurement $B_{yi}$ from the magnetic sensor device 2410 to the second magnetic field measurement values stored in the first look-up table. An error ±ΔB can be included in the second magnetic field measurement $B_{yi}$, in which case the receiver 2420 compares the second magnetic field measurement range $B_{yi}$±ΔB to the second magnetic field measurement values stored in the first look-up table.

In step 2640, the receiver 2420 dynamically creates a second look-up table that includes all rows from the first look-up table that include the second magnetic field measurement $B_{yi}$ or the second magnetic field measurement range $B_{yi}$±ΔB. The second look-up table is thus a subset of the first look-up table. An example of the second look-up table 2730 is illustrated in FIG. 27. The values in the second look-up table 2730 correspond to the intersection of the $B_{xi}$ and $B_{yi}$ planes which results in an array of points spread across various planes parallel to the coil surface (e.g., surface of apparatus 10).

In step 2650 (via placeholder A), the receiver 2450 compares the third magnetic field measurement $B_{zi}$ from the magnetic sensor device 2410 to the third magnetic field measurement values stored in the second look-up table. An error ±ΔB can be included in the third magnetic field measurement $B_{zi}$, in which case the receiver 2420 compares the third magnetic field measurement range $B_{zi}$±ΔB to the third magnetic field measurement values stored in the second look-up table.

In step 2660, the receiver 2420 dynamically creates a third look-up table that includes all rows from the second look-up table that include the third magnetic field measurement $B_{zi}$ or the second magnetic field measurement range $B_{zi}$±ΔB. The third look-up table is thus a subset of the second look-up table. An example of the third look-up table 2740 is illustrated in FIG. 27. The values in the second look-up table 2730 correspond to the intersection of the $B_{xi}$, $B_{yi}$, and $B_{zi}$ planes.

The third look-up table created in step 2660 can include a single row or multiple rows. A single row corresponds to the relative three-dimensional coordinates or position of the magnetic sensor device 2410. When the output of step 2650 includes multiple rows in the second look-up table, then in optional step 2670 the receiver determines the relative three-dimensional coordinates having the smallest Euclidean difference or distance from $B_{xi}$, $B_{yi}$, $B_{zi}$. In the third look-up table 2740, the output coordinates correspond to the $567^{th}$ entry in the main look-up table 2710 (i.e., $x_{567}$, $y_{567}$, $z_{567}$, $B_{x567}$, $B_{y567}$, and $B_{z567}$).

Figure 28:
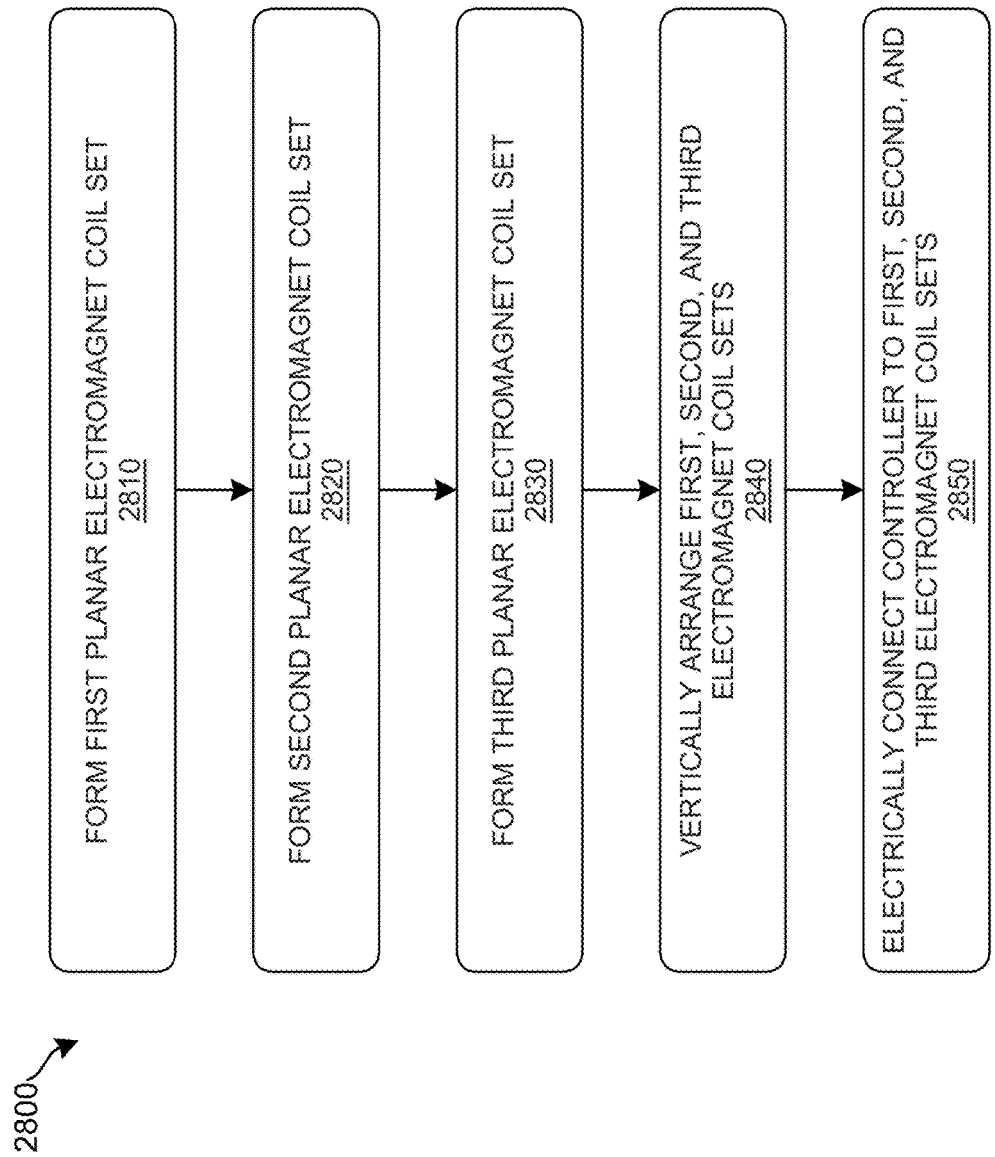
FIG. 28 is a flowchart of a method for manufacturing an apparatus (for producing monotonically-varying magnetic field gradients according to an embodiment.

FIG. 28 is a flowchart of a method 2800 for manufacturing an apparatus (e.g., apparatus 10) for producing monotonically-varying magnetic field gradients according to an embodiment.

In step 2810, a first electromagnet coil set is formed. The first electromagnet coil set (e.g., first electromagnet coil set 110) is configured to produce a first magnetic field gradient with respect to a first axis (e.g., the X axis). In some embodiments, step 1110 includes (a) forming a first clockwise spiral winding with a first wire (e.g., wire 322) and (b) forming a first counterclockwise spiral winding with a second wire (e.g., wire 324). The first clockwise spiral winding and the first counterclockwise spiral winding each have an axis of symmetry that is parallel to the first axis. The first clockwise spiral winding can be placed adjacent or next to the first counterclockwise spiral winding. For example, the first and second wires 322, 324 can physically touch each other or there can be a small gap therebetween. The axis of symmetry of the first clockwise spiral winding can be aligned with the axis of symmetry of the first counterclockwise spiral winding, which can provide a uniform or substantially uniform magnetic field gradient with respect to the first axis.

In some embodiments, forming the first electromagnet coil set includes elongating the first clockwise and counterclockwise spiral windings in a direction parallel to the second axis (e.g., parallel to the Y axis). For example, the first clockwise and counterclockwise spiral windings can comprise ovals, racetracks (e.g., stadium shapes), rectangles, rounded rectangles, or another elongated shape.

The first electromagnet coil set is generally disposed in a plane defined by the first and second axes (e.g., the X and Y axes). For example, the wires that form the first clockwise spiral winding and the first counterclockwise spiral winding have a thickness or height that determines the thickness or height of the first electromagnet coil set. The top and bottom surfaces of the first electromagnet coil set are planar and parallel to the X-Y plane.

In step 2820, a second electromagnet coil set is formed. The second electromagnet coil set (e.g., second electromagnet coil set 120) is configured to produce a second magnetic field gradient with respect to a second axis (e.g., the Y axis) that is orthogonal to the first axis (e.g., the X axis). In some embodiments, step 2820 includes (a) forming a second clockwise spiral winding with a third wire (e.g., wire 822) and (b) forming a second counterclockwise spiral winding with a fourth wire (e.g., wire 824). The second clockwise spiral winding and the second counterclockwise spiral winding each have an axis of symmetry that is parallel to the second axis. The second clockwise spiral winding can be placed adjacent or next to the second counterclockwise spiral winding. For example, the third and fourth wires 822, 824 can physically touch each other or there can be a small gap therebetween. The axis of symmetry of the second clockwise spiral winding can be aligned with the axis of symmetry of the second counterclockwise spiral winding, which can provide a uniform or substantially uniform magnetic field gradient with respect to the second axis.

In some embodiments, forming the second electromagnet coil set includes elongating the second clockwise and counterclockwise spiral windings in a direction parallel to the first axis (e.g., parallel to the X axis). For example, the second clockwise and counterclockwise spiral windings can comprise ovals, racetracks (e.g., stadium shapes), rectangles, rounded rectangles, or another elongated shape.

The second electromagnet coil set is generally disposed in a plane defined by the first and second axes (e.g., the X and Y axes). For example, the wires that form the second clockwise spiral winding and the second counterclockwise spiral winding have a thickness or height that determines the thickness or height of the second electromagnet coil set. The top and bottom surfaces of the second electromagnet coil set are planar and parallel to the X-Y plane.

In step 2830, a third electromagnet coil set is formed. The third electromagnet coil set (e.g., third electromagnet coil set 130) is configured to produce a third magnetic field gradient with respect to a third axis (e.g., the Z axis) that is orthogonal to the first and second axes (e.g., X and Y axes). In some embodiments, step 2830 includes forming a spiral winding with a fifth wire (e.g., wire 612). The spiral winding can be planar within the plane defined by the first and second axes (e.g., X and Y axes). The spiral winding can be in the form of an annulus, ring, or disc in which an internal cavity does not include the spiral winding. The spiral winding can be symmetrical with respect to the first, second, and third axes.

The third electromagnet coil set is generally disposed in a plane defined by the first and second axes (e.g., the X and Y axes). For example, the wire that forms the spiral winding has a thickness or height that determines the thickness or height of the third electromagnet coil set. The top and bottom surfaces of the third electromagnet coil set are planar and parallel to the X-Y plane.

In step 2840, the first, second, and third electromagnet coil sets are vertically arranged and/or aligned with respect to the third axis (e.g., the Z axis). In some embodiments, the first, second, and third electromagnet coil sets can be stacked directly on top of each other.

In step 2850, a controller (e.g., controller 100) is electrically connected to the first, second, and third electromagnet coil sets. The controller is configured to selectively provide power to the first, second, and/or third electromagnet coil sets to produce a localization magnetic field gradient with respect to each axis that has a monotonically-varying magnitude (e.g., a FOV) over at least a portion thereof. For example, the controller can be configured to provide power simultaneously (a) only to the first and third electromagnet coil sets, (b) only to the second and third electromagnet coil sets, and (c) only to the third electromagnet coil set. The power can be provided sequentially to (a), (b), and (c) in a predetermined sequence and/or in a predetermined time sequence that can encode the magnetic field gradients. The power can be provided to (a), (b), and (c) in any order.

The controller can be configured and/or programmed to have a first setting to produce a first localization magnetic field gradient with respect to the first axis where at least a portion of the first localization magnetic field gradient has a monotonically-varying magnitude (e.g., a first FOV with respect to the first axis) along the first axis. In the first setting, the controller provides power simultaneously only to the first and third electromagnet coil sets. The controller can further be configured and/or programmed to have a second setting to produce a second localization magnetic field gradient with respect to the second axis where at least a portion of the second localization magnetic field gradient has a monotonically-varying magnitude (e.g., a second FOV with respect to the second axis) along the second axis. In the second setting, the controller provides power simultaneously only to the second and third electromagnet coil sets. The controller can further be configured and/or programmed to have a third setting to produce a third localization magnetic field gradient with respect to the third axis where at least a portion of the third localization magnetic field gradient has a monotonically-varying magnitude (e.g., a third FOV with respect to the third axis) along the third axis. In the third setting, the controller provides power simultaneously only to the third electromagnet coil set. The controller can be configured to selective provide power according to the first, second, and third settings sequentially and/or in a predetermined time sequence, both of which can encode the first, second, and third localization magnetic field gradients.

In some embodiments, the controller or a receiver can store data that represents a series of measured magnetic field measurements at known positions relative to the electromagnet coil sets for each magnetic field gradient, for example as discussed herein. The data can be stored in a database, a lookup table, or in another form. Alternatively, the controller can store a mathematical model of the data that can be used to determine the relative position of a magnetic sensor for a given magnetic field measurement of a magnetic sensor device. In another embodiment, a computer or receiver for the magnetic sensor device can store the data and/or the mathematical model. The computer or receiver can be in communication with the controller. Additional details on localizing a magnetic sensor device using magnetic field gradients are disclosed in (a) U.S. Pat. No. 9,915,641, titled "Sensing and Actuation Of Biological Function Using Addressable Transmitters Operated As Magnetic Spins," issued on Mar. 13, 2018, (b) U.S. Pat. No. 10,466,227, titled "Sensing and Actuation Of Biological Function Using Addressable Transmitters Operated As Magnetic Spins," issued on Nov. 5, 2019, (c) U.S. Patent Application Publication No. 2019/0388105, titled "Surgical Alignment By Magnetic Field Gradient Localization," published on Dec. 26, 2019, (d) U.S. patent application Ser. No. 17/097,421, titled "In-Vitro Monitoring Of An Internal Volume Of A Mammal Using Magnetic Field Gradients," filed on Nov. 13, 2020, which claims priority to U.S. Provisional Application No. 62/934,763, titled "Real-Time GI Tract Monitoring with High Precision in 3D Using ATOMS Microchips," filed on Nov. 13, 2019, and to Provisional Application No. 62/934,767, titled "Magnetic Gradient Coil Design For Micro-Device Localization," filed on Nov. 13, 2019, and (e) U.S. Provisional Application No. 63/075,980, titled "Precision Surgery Using Smart Surgical Tags," filed on Sep. 9, 2020, each of which is hereby incorporated by reference.

Figure 29:
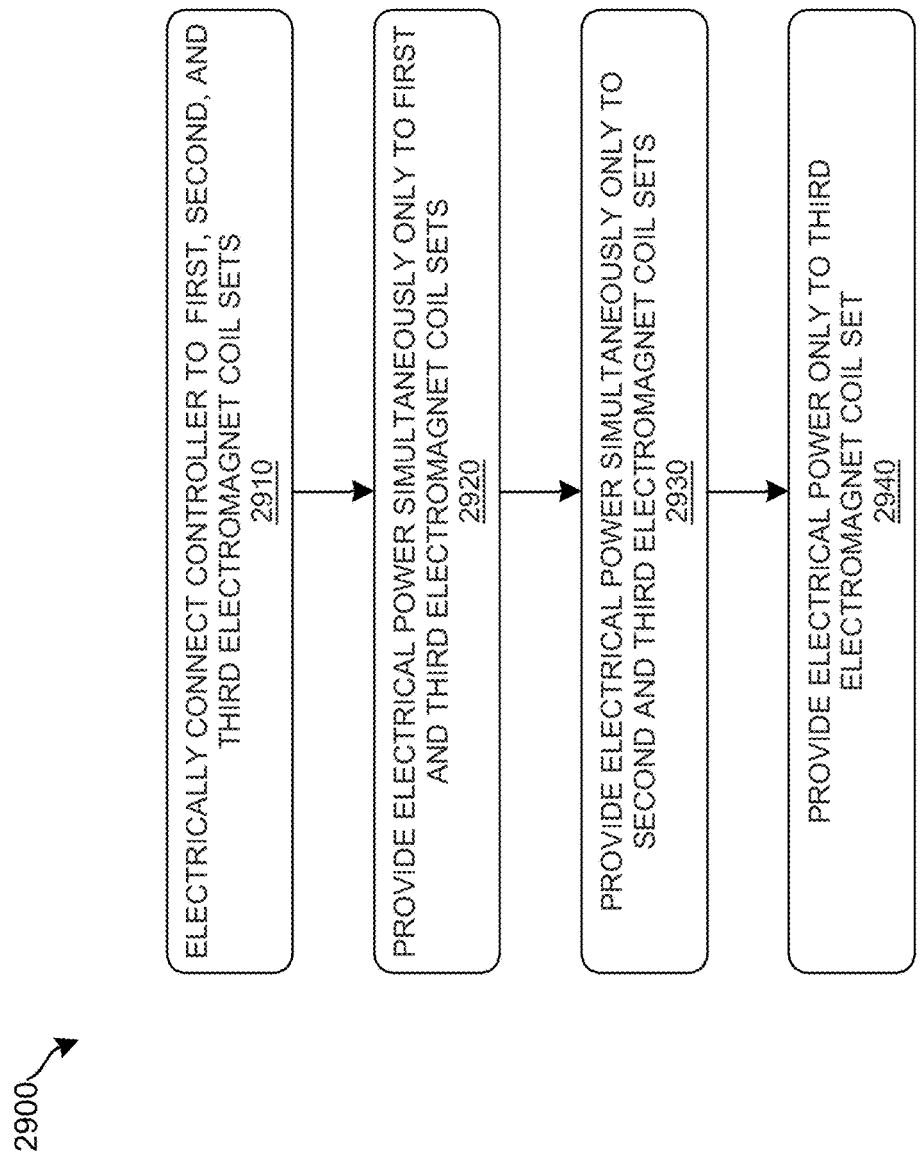
FIG. 29 is a flow chart of a method for producing magnetic field gradients according to an embodiment.

FIG. 29 is a flow chart 2900 of a method for producing magnetic field gradients according to an embodiment. In step 2910, a controller (e.g., controller 100) is electrically connected to (a) a first electromagnet coil set configured to produce a first magnetic field, (b) a second electromagnet coil set configured to produce a second magnetic field, and (c) a third electromagnet coil set configured to produce a third magnetic field. The first, second, and third electromagnet coil sets can be same as the first, second, and third electromagnet coil sets 110, 120, 130, respectively.

In step 2920, the controller provides electrical power simultaneously to only (a) the first electromagnet coil set and (c) the third electromagnet coil set. The controller does not provide power to (b) the second electromagnet coil set during step 2920. Providing electrical power simultaneously to only (a) the first electromagnet coil set and (c) the third electromagnet coil set produces a first combined magnetic field gradient with respect to the first axis. The first combined magnetic field gradient includes the first magnetic field produced by the first electromagnet coil set and the third magnetic field produced by the third electromagnet coil set. The third magnetic field can function as an offset to the first magnetic field such that the first combined magnetic field gradient has a monotonically-varying magnitude with respect to the first axis along at least a portion thereof (e.g., FOV), such as along a portion of the first electromagnet coil set.

In step 2930, the controller provides electrical power simultaneously to only (b) the second electromagnet coil set and (c) the third electromagnet coil set. The controller does not provide power to (a) the first electromagnet coil set during step 2930. Providing electrical power simultaneously to only ((b) the second electromagnet coil set and (c) the third electromagnet coil set produces a second combined magnetic field gradient with respect to the second axis. The second combined magnetic field gradient includes the second magnetic field produced by the second electromagnet coil set and the third magnetic field produced by the third electromagnet coil set. The third magnetic field can function as an offset to the second magnetic field such that the second combined magnetic field gradient has a monotonically-varying magnitude with respect to the second axis along at least a portion thereof (e.g., FOV), such as along a portion of the second electromagnet coil set.

In step 2940, the controller provides electrical power only to (c) the third electromagnet coil set. Providing electrical power to only (c) the third electromagnet coil set produces the third magnetic field gradient which has a monotonically-varying magnitude along with respect to the third axis at least a portion thereof (e.g., FOV).

In an embodiment, steps 2920, 2930, and 2940 can be repeated according to a predetermined time sequence. The predetermined time sequence can encode the magnetic field gradients based on the time and/or sequence. Steps 2920, 2930, and 2940 do not need to be performed in the order illustrated in method 2900. However, steps 2920, 2930, and 2940 are preferably performed in the same order in each predetermined time sequence to encode the magnetic field gradients. In an alternative embodiment, steps 2920, 2930, and 2940 can be performed in a different or random sequence order in each loop through method 2900 to encrypt the magnetic field gradients.

Figure 30:
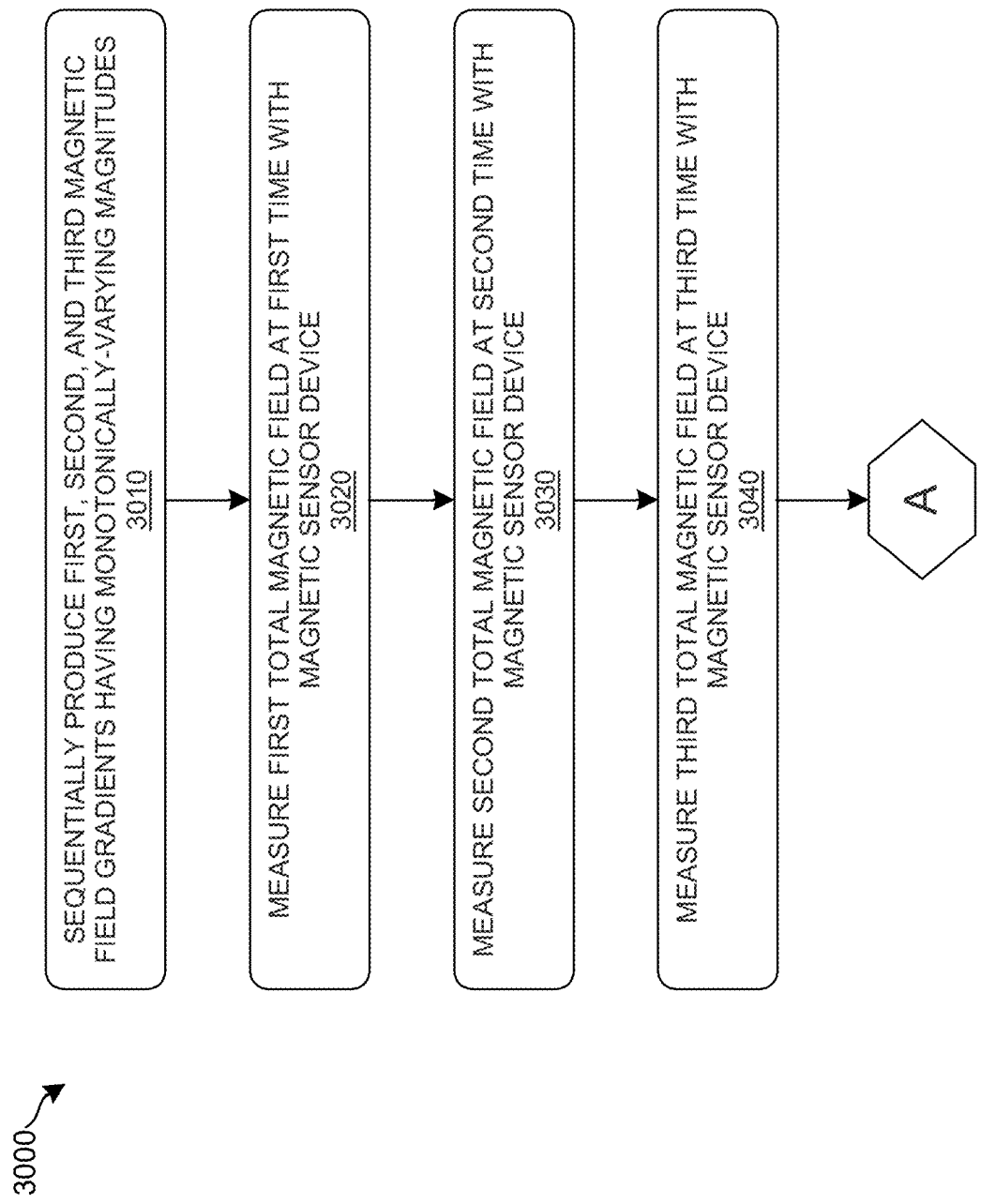
FIG. 30 is a flow chart of a method for determining a relative position of an object using magnetic field gradients according to an embodiment.

FIG. 30 is a flow chart of a method 3000 for determining a relative position of an object using magnetic field gradients according to an embodiment. In step 3010, a three-dimensional magnetic field generator (e.g., apparatus 10) sequentially produces (a) a first magnetic field gradient along a first axis, the first magnetic field gradient having a monotonically-varying magnitude along a portion of the first axis, (b) a second magnetic field gradient along a second axis that is orthogonal to the first axis, the second magnetic field gradient having a monotonically-varying magnitude along a portion of the second axis, and (c) a third magnetic field gradient along a third axis that is orthogonal to the first and second axes, the third magnetic field gradient having a monotonically-varying magnitude along a portion of the third axis. The first magnetic field gradient is produced at a first time or time period. The second magnetic field gradient is produced at a second time or time period that is different than the first time or time period, The third magnetic field gradient is produced at a third time or time period that is different than the first and second times or time periods.

In step 3020, a three-dimensional magnetic sensor (e.g., three-dimensional magnetic sensor 2412) in a magnetic sensor device (e.g., magnetic sensor device 2410) is used to measure a first total magnetic field (e.g., a first localization magnetic field), at the three-dimensional position of the magnetic sensor device, at the first time or time period. The first total magnetic field corresponds to the first magnetic field gradient produced in step 3010.

In step 3030, the three-dimensional magnetic sensor (e.g., three-dimensional magnetic sensor 2412) in magnetic sensor device (e.g., magnetic sensor device 2410) is used to measure a second total magnetic field (e.g., a second localization magnetic field), at the three-dimensional position of the magnetic sensor device, at the second time or time period. The second total magnetic field corresponds to the second magnetic field gradient produced in step 3010.

In step 3040, the three-dimensional magnetic sensor (e.g., three-dimensional magnetic sensor 2412) in magnetic sensor device (e.g., magnetic sensor device 2410) is used to measure a third total magnetic field (e.g., a third localization magnetic field), at the three-dimensional position of the magnetic sensor device, at the third time or time period. The third total magnetic field corresponds to the third magnetic field gradient produced in step 3010.

In step 3050, the magnetic sensor device broadcasts the measurement of the first, second, and third total magnetic fields with a device antenna (e.g., antenna 2416). The measurements can be encoded in an output signal for example by a processor in the magnetic sensor device.

In step 3060, the measurement of the first, second, and third total magnetic fields is received by a microprocessor-based receiver that includes a receiver antenna.

In step 3070, the receiver uses the measurement of the first, second, and third total magnetic fields to determine the three-dimensional position of the magnetic sensor device. For example, the receiver can use a look-up table according to method 2600. Alternatively, the receiver can use a mathematical model, machine learning or other method to determine the three-dimensional position of the magnetic sensor device using the measurement of the first, second, and third total magnetic fields. The receiver can then display, output, and/or store the three-dimensional position of the magnetic sensor device determine in step 3070.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An apparatus for producing magnetic field gradients comprising:
    a first planar electromagnet coil set configured to produce a first magnetic field gradient with respect to a first axis;
    a second planar electromagnet coil set configured to produce a second magnetic field gradient with respect to a second axis that is orthogonal to the first axis;
    a third planar electromagnet coil set configured to produce a third magnetic field gradient with respect to a third axis that is orthogonal to the first and second axes, the first, second, and third planar electromagnet coil sets vertically arranged with respect to the third axis; and
    a controller configured to selectively provide power to the first planar electromagnet coil set, the second planar electromagnet coil set, and/or the third planar electromagnet coil set to sequentially produce a localization magnetic field gradient with respect to each of the first, second, and third axes, at least a portion of each localization magnetic field gradient having a monotonically-varying magnetic field magnitude along a respective axis,
    wherein the controller is configured to provide power simultaneously to only the first and third planar electromagnet coil sets to thereby produce a first localization magnetic field gradient with respect to the first axis.

2. The apparatus of claim 1, wherein the first planar electromagnet coil set, the second planar electromagnet coil set, and the third planar electromagnet coil set are stacked.

3. The apparatus of claim 1, wherein the first planar electromagnet coil set includes a clockwise spiral winding and a counterclockwise spiral winding that are disposed adjacent to each other.

4. The apparatus of claim 3, wherein the clockwise spiral winding and the counterclockwise spiral winding are each formed by a respective wire.

5. The apparatus of claim 3, wherein:
the clockwise spiral winding and the counterclockwise spiral winding are each elongated in a direction parallel to the second axis,
the clockwise spiral winding and the counterclockwise spiral winding each have an axis of symmetry that is parallel to the first axis, and
the axis of symmetry of the clockwise spiral winding is aligned with the axis of symmetry of the counterclockwise spiral winding.

6. The apparatus of claim 5, wherein:
the first planar electromagnet coil set has a width that is parallel to the first axis, and
a ratio of (a) the at least a portion of the localization magnetic field gradient that has the monotonically-varying magnetic field magnitude along the first axis to (b) the width of the first planar electromagnet coil set is within a range of about 1:2 to about 3:4.

7. The apparatus of claim 6, wherein the ratio is about 2:3.

8. The apparatus of claim 3, wherein:
the clockwise spiral winding is a first clockwise spiral winding,
the counterclockwise spiral winding is a first counterclockwise spiral winding, and
the second planar electromagnet coil set includes a second clockwise spiral winding and a second counterclockwise spiral winding that are disposed adjacent to each other.

9. The apparatus of claim 8 wherein the first clockwise spiral winding, the second clockwise spiral winding, the first counterclockwise spiral winding, and the second counterclockwise spiral winding are each formed by a respective wire.

10. The apparatus of claim 8, wherein:
the first clockwise spiral winding and the first counterclockwise spiral winding are each elongated in a direction parallel to the second axis,
the first clockwise spiral winding and the first counterclockwise spiral winding each have an axis of symmetry that is parallel to the first axis,
the axis of symmetry of the first clockwise spiral winding is aligned with the axis of symmetry of the first counterclockwise spiral winding,
the second clockwise spiral winding and the second counterclockwise spiral winding are each elongated in a direction parallel to the first axis,
the second clockwise spiral winding and the second counterclockwise spiral winding each have an axis of symmetry that is parallel to the second axis, and
the axis of symmetry of the second clockwise spiral winding is aligned with the axis of symmetry of the second counterclockwise spiral winding.

11. The apparatus of claim 10, wherein:
the first planar electromagnet coil set has a width that is parallel to the first axis,
the second planar electromagnet coil set has a length that is parallel to the second axis,
a ratio of (a) the at least a portion of the localization magnetic field gradient that has the monotonically-varying magnetic field magnitude along the first axis to (b) the width of the first planar electromagnet coil set is greater than or equal to about 1:2, and
a ratio of (c) the at least a portion of the localization magnetic field gradient that has the monotonically-varying magnetic field magnitude along the second axis to (d) the length of the second planar electromagnet coil set is less than or equal to about 1:2.

12. The apparatus of claim 11, wherein:
the ratio (a) the at least a portion of the localization magnetic field gradient that has the monotonically-varying magnetic field magnitude along the first axis to (b) the width of the first planar electromagnet coil set is within a range of about 1:2 to about 3:4, and
the ratio of (c) the at least a portion of the localization magnetic field gradient that has the monotonically-varying magnetic field magnitude along the second axis to (d) the length of the second planar electromagnet coil set is within a range of about 1:2 to about 3:4.

13. The apparatus of claim 11, wherein the third planar electromagnet coil set includes a spiral winding having a form of an annulus.

14. The apparatus of claim 13, wherein:
the annulus has an outer diameter measured parallel to the first axis, and
a ratio of (e) the at least a portion of the localization magnetic field gradient that has the monotonically-varying magnetic field magnitude along the third axis to (f) the outer diameter of the annulus is within a range of about 1:4 to about 2:5.

15. The apparatus of claim 14, wherein the ratio of (e) the at least a portion of the localization magnetic field gradient that has the monotonically-varying magnetic field magnitude along the third axis to (f) the outer diameter of the annulus is about 1:3.

16. The apparatus of claim 1, wherein the first localization magnetic field gradient comprises a total magnetic field produced by the first and third planar electromagnet coil sets.

17. The apparatus of claim 16, wherein the controller is configured to provide power simultaneously to only the second and third planar electromagnet coil sets to thereby produce a second localization magnetic field gradient with respect to the second axis.

18. The apparatus of claim 16, wherein the second localization magnetic field gradient comprises a total magnetic field produced by the second and third planar electromagnet coil sets.

19. The apparatus of claim 17, wherein the controller is configured to provide power to only the third planar electromagnet coil set to thereby produce a third localization magnetic field gradient with respect to the third axis.

20. The apparatus of claim 17, wherein the controller is configured to selectively provide the power according to a predetermined time sequence to encode each localization magnetic field gradient.

21. A method for manufacturing comprising:
forming a first planar electromagnet coil set configured to produce a first magnetic field gradient with respect to a first axis;
forming a second planar electromagnet coil set configured to produce a second magnetic field gradient with respect to a second axis that is orthogonal to the first axis;
forming a third planar electromagnet coil set configured to produce a third magnetic field gradient with respect to a third axis that is orthogonal to the first and second axes;

vertically arranging the first, second, and third planar electromagnet coil sets along the third axis;

electrically connecting a controller to the first planar electromagnet coil set, the second planar electromagnet coil set, and the third planar electromagnet coil set, the controller configured to selectively provide power to the first planar electromagnet coil set, the second planar electromagnet coil set, and/or the third planar electromagnet coil set to produce a localization magnetic field gradient with respect to each of the first, second, and third axes, at least a portion of each localization magnetic field gradient having a monotonically-varying magnetic field magnitude along a respective axis; and configuring the controller with a first setting that provides power to only the first planar electromagnet coil set and the third planar electromagnet coil set to produce a first localization magnetic field gradient with respect to the first axis, at least a portion of the first localization magnetic field gradient having a monotonically-varying magnetic field magnitude along the first axis.

22. The method of claim 21, wherein forming the first planar electromagnet coil set comprises:

forming a first clockwise spiral winding with a first wire, the first clockwise spiral winding having an axis of symmetry that is parallel to the first axis;

forming a first counterclockwise spiral winding with a second wire, the first counterclockwise spiral winding having an axis of symmetry that is parallel to the first axis;

placing the first clockwise spiral winding adjacent to the first counterclockwise spiral winding; and aligning the axis of symmetry of the first clockwise spiral winding with the axis of symmetry of the first counterclockwise spiral winding.

23. The method of claim 22, wherein forming the second planar electromagnet coil set comprises:

forming a second clockwise spiral winding with a third wire, the second clockwise spiral winding having an axis of symmetry that is parallel to a second axis that is orthogonal to the first axis;

forming a second counterclockwise spiral winding with a fourth wire, the second counterclockwise spiral winding having an axis of symmetry that is parallel to the second axis;

placing the second clockwise spiral winding adjacent to the second counterclockwise spiral winding; and aligning the axis of symmetry of the second clockwise spiral winding with the axis of symmetry of the second counterclockwise spiral winding.

24. The method of claim 23, wherein forming the third planar electromagnet coil set comprises forming a spiral winding with a fifth wire in a shape of an annulus, the spiral winding having an axis of symmetry that is parallel to a third axis that is orthogonal to the first and second axes.

25. The method of claim 24, further comprising elongating the first clockwise spiral winding and the first counterclockwise spiral winding in a direction parallel to the second axis.

26. The method of claim 25, further comprising elongating the second clockwise spiral winding and the second counterclockwise spiral winding in a direction parallel to the first axis.

27. The method of claim 21, further comprising vertically stacking the first planar electromagnet coil set, the second planar electromagnet coil set, and the third planar electromagnet coil set.

28. The method of claim 21, further comprising configuring the controller with a second setting that provides power to only the second planar electromagnet coil set and the third planar electromagnet coil set to produce a second localization magnetic field gradient with respect to the second axis, at least a portion of the second localization magnetic field gradient having a monotonically-varying magnetic field magnitude along the second axis.

29. The method of claim 28, further comprising configuring the controller with a third setting that provides power to only the third planar electromagnet coil set to produce a third localization magnetic field gradient with respect to the third axis, at least a portion of the third localization magnetic field gradient having a monotonically-varying magnetic field magnitude along the third axis.

30. The method of claim 29, further comprising configuring the controller to provide power according to the first, second, and third settings in a predetermined time sequence to encode the respective first, second, and third localization magnetic field gradients.

31. A method of producing magnetic field gradients, comprising:

electrically connecting a controller to (a) a first planar electromagnet coil set configured to produce a first magnetic field gradient with respect to a first axis, (b) a second planar electromagnet coil set configured to produce a second magnetic field gradient with respect to a second axis, and (c) a third planar electromagnet coil set configured to produce a third magnetic field gradient with respect to a third axis, wherein the first, second, and third axes are orthogonal to one another, wherein the first, second, and third planar electromagnet coil sets are vertically arranged with respect to the third axis;

with the controller, providing electrical power simultaneously only to (a) and (c) at a first time;

with the controller, providing electrical power simultaneously only to (b) and (c) at a second time that is different than the first time; and with the controller, providing electrical power only to (c) at a third time that is different than the first and second times.

32. The method of claim 31, wherein providing electrical power simultaneously only to (a) and (c) comprises producing a first combined magnetic field gradient with respect to the first axis, at least a portion of the first combined magnetic field gradient having a monotonically-varying magnetic field magnitude along the first axis.

33. The method of claim 32, wherein:

the first planar electromagnet coil set has a width that is parallel to the first axis, and a ratio of (a) the at least a portion of the first combined magnetic field gradient that has the monotonically-varying magnetic field magnitude along the first axis to (b) the width of the first electromagnet coil set is within a range of about 1:2 to about 3:4.

34. The method of claim 32, wherein providing electrical power simultaneously only to (b) and (c) comprises producing a second combined magnetic field gradient with respect to the second axis, the second combined magnetic field gradient having a monotonically-varying magnitude over at least a portion of the second electromagnet coil set.

35. The method of claim 34, wherein:

the second planar electromagnet coil set has a length that is parallel to the second axis, and a ratio of (a) the at least a portion of the second combined magnetic field gradient that has the monotonically-varying magnetic field magnitude along the first axis to (b) the length of the second electromagnet coil set is within a range of about 1:2 to about 3:4.

36. The method of claim 31, wherein providing electrical power only to (c) comprises producing the third magnetic field gradient, at least a portion of the third magnetic field gradient having a monotonically-varying magnetic field magnitude along the third axis.

37. The method of claim 36, wherein:
the third planar electromagnet coil set includes a spiral winding having a form of an annulus,
the annulus has an outer diameter measured parallel to the first axis, and
a ratio of (e) the at least a portion of the third magnetic field gradient that has the monotonically-varying magnetic field magnitude along the third axis to (f) the outer diameter of the annulus is within a range of about 1:4 to about 2:5.

38. The method of claim 31, further comprising repeating the following steps according to a predetermined time sequence:
providing electrical power simultaneously only to (a) and (c) at the first time,
providing electrical power simultaneously only to (b) and (c) at the second time, and
providing electrical power only to (c) at the third time.

39. A system comprising:
a three-dimensional magnetic field generator comprising:
  a first electromagnet coil set configured to produce a first magnetic field gradient along a first axis;
  a second electromagnet coil set configured to produce a second magnetic field gradient along a second axis that is orthogonal to the first axis;
  a third electromagnet coil set configured to produce a third magnetic field gradient along a third axis that is orthogonal to the first and second axes; and
  a controller configured to selectively provide power to the first electromagnet coil set, the second electromagnet coil set, and/or the third electromagnet coil set to sequentially produce a localization magnetic field gradient with respect to each of the first, second, and third axes, at least a portion of each localization magnetic field gradient having a monotonically-varying magnetic field magnitude along a respective axis,
  wherein the controller is configured to provide power simultaneously to only the first and third planar electromagnet coil sets to thereby produce a first localization magnetic field gradient with respect to the first axis;
a magnetic sensor device comprising:
  a three-dimensional magnetic sensor that outputs a measurement of each localization magnetic field gradient;
  a controller electrically coupled to the three-dimensional magnetic sensor, the controller generating a magnetic sensor output signal that encodes the measurement of each localization magnetic field gradient;
  a device antenna electrically coupled to the controller, the device antenna broadcasting the magnetic sensor output signal; and
  a power source electrically coupled to the three-dimensional magnetic sensor and the controller; and
a receiver comprising:
  a microprocessor;
  a receiver antenna that receives the magnetic sensor output signal from the device antenna; and
  non-volatile memory accessible to the microprocessor, the non-volatile memory including computer-readable instructions that, when executed by the processor, cause the microprocessor to determine a three-dimensional position of the magnetic sensor device using the measurement of each localization magnetic field gradient.

40. The system of claim 39, wherein the non-volatile memory includes a look-up table that includes a plurality of measurements of each localization magnetic field gradient at known three-dimensional positions.

41. A method for determining a relative position of an object using magnetic field gradients, comprising:
with a three-dimensional magnetic field generator, sequentially producing:
  a first localization magnetic field gradient along a first axis, at least a portion of the first localization magnetic field gradient having a monotonically-varying magnetic field magnitude along the first axis, the first localization magnetic field gradient produced at a first time,
  a second localization magnetic field gradient along a second axis that is orthogonal to the first axis, at least a portion of the second localization magnetic field gradient having a monotonically-varying magnetic field magnitude along the second axis, the second localization magnetic field gradient produced at a second time that is different than the first time, and
  a third localization magnetic field gradient along a third axis that is orthogonal to the first and second axes, at least a portion of the third localization magnetic field gradient having a monotonically-varying magnetic field magnitude along the third axis, the third localization magnetic field gradient produced at a third time that is different than the first and second times,
wherein the three-dimensional magnetic field generator comprises:
  a first planar electromagnet coil set configured to produce a first magnetic field gradient with respect to the first axis;
  a second planar electromagnet coil set configured to produce a second magnetic field gradient with respect to the second axis;
  a third planar electromagnet coil set configured to produce a third magnetic field gradient with respect to the third axis, the first, second, and third planar electromagnet coil sets vertically arranged with respect to the third axis; and
  a controller configured to selectively provide power to the first planar electromagnet coil set, the second planar electromagnet coil set, and/or the third planar electromagnet coil set to sequentially produce the first, second, and third localization magnetic field gradients
  wherein the controller is configured to provide power simultaneously to only the first and third planar electromagnet coil sets to thereby produce the first localization magnetic field gradient with respect to the first axis;
with a magnetic sensor device comprising a three-dimensional magnetic sensor and a device antenna,
  measuring a first total magnetic field, at a three-dimensional position of the magnetic sensor device, at the first time;

measuring a second total magnetic field, at the three-dimensional position of the magnetic sensor device, at the second time;
measuring a third total magnetic field, at the three-dimensional position of the magnetic sensor device, at the third time; and
broadcasting a measurement of the first, second, and third total magnetic fields with the device antenna; and with a receiver comprising a microprocessor and a receiver antenna,
receiving the measurement of the first, second, and third total magnetic fields with the receiver antenna; and
determining the three-dimensional position of the magnetic sensor device using the measurement of the first, second, and third total magnetic fields.

* * * * *